United States Patent
Chen et al.

(10) Patent No.: US 12,157,726 B2
(45) Date of Patent: *Dec. 3, 2024

(54) P-PHENYLENEDIAMINE DERIVATIVE AS POTASSIUM CHANNEL REGULATOR AND PREPARATION METHOD AND MEDICAL APPLICATION THEREOF

(71) Applicant: Shanghai Zhimeng Biopharma, Inc., Shanghai (CN)

(72) Inventors: Huanming Chen, Shanghai (CN); Bo Liang, Shanghai (CN)

(73) Assignee: SHANGHAI ZHIMENG BIOPHARMA INC.

( * ) Notice: Subject to any disclaimer, the term of this patent is extended or adjusted under 35 U.S.C. 154(b) by 5 days.

This patent is subject to a terminal disclaimer.

(21) Appl. No.: 17/715,935

(22) Filed: Apr. 7, 2022

(65) Prior Publication Data

US 2022/0227721 A1 Jul. 21, 2022

Related U.S. Application Data

(63) Continuation of application No. 17/057,457, filed as application No. PCT/CN2019/088012 on May 22, 2019, now Pat. No. 11,365,181.

(30) Foreign Application Priority Data

May 22, 2018 (CN) .......................... 201810493023.9

(51) Int. Cl.
| | | |
|---|---|---|
| *A61K 31/165* | (2006.01) | |
| *A61P 9/10* | (2006.01) | |
| *A61P 25/00* | (2006.01) | |
| *A61P 25/06* | (2006.01) | |
| *A61P 25/08* | (2006.01) | |
| *A61P 25/22* | (2006.01) | |
| *A61P 25/28* | (2006.01) | |
| *A61P 25/32* | (2006.01) | |
| *A61P 25/34* | (2006.01) | |
| *A61P 27/16* | (2006.01) | |
| *A61P 29/00* | (2006.01) | |
| *C07D 267/14* | (2006.01) | |
| *C07D 495/04* | (2006.01) | |

(52) U.S. Cl.
CPC ......... *C07D 267/14* (2013.01); *C07D 495/04* (2013.01)

(58) Field of Classification Search
CPC ........ A61K 31/165; A61P 25/00; A61P 25/08; A61P 29/00; A61P 25/06; A61P 25/28; A61P 25/22; A61P 9/10; A61P 25/34; A61P 25/32; A61P 27/16

See application file for complete search history.

(56) References Cited

U.S. PATENT DOCUMENTS

| 8,993,593 B2 | 3/2015 | Vernier et al. |
|---|---|---|
| 2021/0163429 A1 | 6/2021 | Chen et al. |

FOREIGN PATENT DOCUMENTS

| JP | 2010535244 A | 11/2010 |
|---|---|---|
| WO | 2006029623 A1 | 3/2006 |
| WO | 2008/024398 A2 | 2/2008 |
| WO | 2008066900 A1 | 6/2008 |
| WO | 2008157404 A2 | 12/2008 |
| WO | 2009015667 A1 | 2/2009 |
| WO | 2014/048165 A1 | 4/2014 |
| WO | 2021113757 A1 | 6/2021 |

OTHER PUBLICATIONS

Meanwell, Synopsis of Some Recent Tactical Application of Bioisosteres in Drug Design, 54 J. Med. Chem. 2529-2591 (2011).
Int'l Search Report issued Aug. 23, 2019 in Int'l Application No. PCT/CN2019/088012.
Yang et al, "Design, synthesis and evaluation of novel N-phenylbutanamide derivatives as KCNQ openers for the treatment of epilepsy," Bioorganic & Medicinal Chemistry Letters, vol. 28, pp. 3004-3008 (2018).
Chemical structure of PubChem CID # 123454460, PubChem, U.S. National Library of Medicine, Create date Jan. 24, 2017, at https://pubchem.ncbi.nlm.nih.gov/compound/123454460.
Chemical structure of PubChem CID # 123554081, PubChem, U.S. National Library of Medicine, Create date Jan. 25, 2017, at https://pubchem.ncbi.nlm.nih.gov/compound/123554081.
Notice of Allowance sent Mar. 22, 2022 in U.S. Appl. No. 17/057,457.
Office Action sent Nov. 22, 2021 in U.S. Appl. No. 17/057,457.
Bierbower et al., "Augmentation of M-Type (KCNQ) Potassium Channels as a Novel Strategy to Reduce Stroke-Induced Brain Injury," The Journal of Neuroscience, vol. 35, No. 5, pp. 2101-2111 (2015).
Blackburn-Munro et al., "The anticonvulsant retigabine attenuates nociceptive behaviours in rat models of persistent and neuropathic pain," European Journal of Pharmacology, vol. 460, pp. 109-116 (2003).
Borgini et al., "Chemical Modulation of Kv7 Potassium Channels," RSC Medicinal Chemistry, 61 pages (2020).

(Continued)

*Primary Examiner* — Bruck Kifle
(74) *Attorney, Agent, or Firm* — Panitch Schwarze Belisario & Nadel LLP

(57) ABSTRACT p-phenylenediamine derivatives as potassium channel regulators and preparation methods and medical application thereof. A compound represented by general formula A or a pharmaceutically acceptable salt thereof. A preparation method of the compound and a use of the same as a potassium channel opener.

11 Claims, No Drawings

(56) References Cited

OTHER PUBLICATIONS

Gunthorpe et al., "The mechanism of action of retigabine (ezogabine), a first-in-class K+ channel opener for the treatment of epilepsy," Epilepsia, vol. 53, No. 3, pp. 412-424 (2012).
Schrøder et al., "KCNQ4 channel activation by BMS-204352 and retigabine," Neuropharmacology, vol. 40, pp. 888-898 (2001).
Search results for Retigabine from <https://clinicaltrials.gov/>; search conducted Jan. 5, 2024, 4 pages.
Wainger et al., "Effect of Ezogabine on Cortical and Spinal Motor Neuron Excitability in Amyotrophic Lateral Sclerosis A Randomized Clinical Trial," JAMA Neurology, Original Investigation, pp. E1-E11 (2020).

P-PHENYLENEDIAMINE DERIVATIVE AS POTASSIUM CHANNEL REGULATOR AND PREPARATION METHOD AND MEDICAL APPLICATION THEREOF

CROSS-REFERENCE TO RELATED APPLICATIONS

This application is a Continuation of U.S. patent application Ser. No. 17/057,457, filed Nov. 20, 2020, which is a Section 371 U.S. National Stage of International Application No. PCT/CN2019/088012, filed May 22, 2019, which was published in the Chinese language on Nov. 28, 2019 under International Publication No. WO 2019/223732 A1, which claims priority under 35 U.S.C. § 119(b) to Chinese Application No. 201810493023.9, filed on May 22, 2018, the disclosures of which are incorporated herein by reference in their entireties.

TECHNICAL FIELD

The present invention belongs to the field of biomedicine. Specifically, the present invention relates to p-diaminobenzene derivatives, their preparation methods and their applications in medicine. Such compounds regulate potassium ion channels and are useful for the treatment and prevention of diseases and conditions affected by the activity of potassium ion channels.

BACKGROUND ART

KCNQs, later renamed as Kv 7 channels, are members of the voltage-dependent, non-inactivating potassium channel family. There are 5 genes in the known KCNQ family. They are named as KCNQ 1-5 according to the order of discovery, all of them are coded for potassium channel subunits. KCNQs (KCNQ 1-5) gene-encoded prosthetic groups regulate the expression, biophysical and pharmacological properties of KCNQ channels. KCNQ 1-4 gene mutations can reduce potassium ion current. KCNQs not only participate in regulation of many important physiological functions of the body, but also play an important role in the occurrence of certain diseases. Among them, 4 gene mutations are associated with different genetic diseases. KCNQ 1 is expressed in the heart and inner ear, and its gene mutations cause L-QT syndrome and congenital deafness (Jervell and Lange-Nielsen syndrome). In addition, diabetes may also be related to this gene. Four of five members of KCNQs family (KCNQ 2-5) are expressed in the nervous system. Among them, KCNQ 2 and KCNQ 3 are widely expressed in the neocortex and hippocampus. Their genetic mutations can cause benign familial neonatal convulsions (BFNC). KCNQ 2 gene mutations are related to peripheral nerve hyperexcitability. The heteromultimeric ion channel composed of KCNQ 2 and KCNQ 3 is a molecular basis of M type potassium current in the nervous system. Further, M type potassium current is closely related to maintain the stability of membrane potential and the excitability of cell. KCNQ 5 is widely expressed in the central and peripheral nervous system, and is also involved in the formation of M-type channels. Research indicates that KCNQ 4 is limited to inner ear hair cells and auditory nerves, and its genetic mutations can cause neurological deafness. KCNQs not only are important determinants of the excitability of the myocardium and nerve cell membranes, but also are widely expressed in other smooth muscles. KCNQ 4 and KCNQ 5 are expressed throughout the gastrointestinal tract and are the main regulator of smooth muscle activity in the digestive tract. KCNQs are also selectively distributed on arterio-venous vascular muscle cells ("Chin J Nery Ment Dis, 2011, 37, 124-126).

Retigabine is a drug for the treatment of epilepsy. It has been approved for marketing in the United Kingdom, Germany and Denmark. Researches have confirmed that the effect of retigabine is related to voltage-gated potassium ion channels (KCNQs), wherein its main mechanism are acting on the KCNQ2/3 channel and modulating the M type potassium current.

It has been reported that KCNQ2 and KCNQ3 are up-regulated in neuropathic pain models (Wickenden etc, Sccoety for Neuroscience Abstracts, 2002, 454, 7), and it has been hypothesized that potassium ion channel modulators are effective in both neuropathic pain and epilepsy (Schroder etc, Neuropharmacology, 2001, 40, 888-898).

Researches have shown that retigabine is beneficial in animal models of neuropathic pain (Blackbum-Munro, European Journal of Pharmacology, 2003, 460, 109-116), which indicates that potassium ion channel openers may be used to treat painful conditions including neuropathic pain.

Therefore, it is very necessary to develop new and effective potassium ion channel openers.

SUMMARY OF THE INVENTION

The purpose of the present invention is to provide a new type of p-diaminobenzene derivatives that can be used as potassium ion channel openers.

The purpose of the present invention is to provide a method for preparing the above compound.

The purpose of the present invention is also to provide the application of the above compounds as potassium ion channel openers for the treatment of pain, stroke, epilepsy and other diseases.

The present invention also provides a method for preventing or treating diseases related to potassium ion channels, which comprises administering the compound or the pharmaceutical composition of the present invention to a subject in need thereof.

In the first aspect of the invention, it provides a compound represented by formula A or a pharmaceutically acceptable salt thereof:

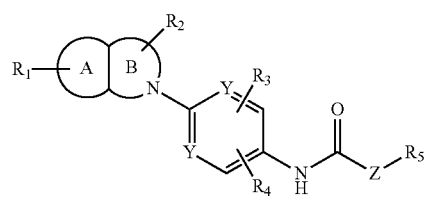

Formula A wherein:
when ring B is

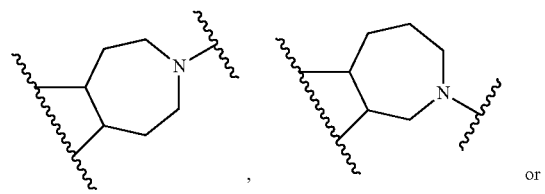

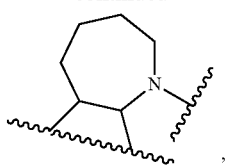

ring A is a saturated or unsaturated heterocyclic containing 1 to 2 heteroatoms selected from N, S and O;

when ring B is

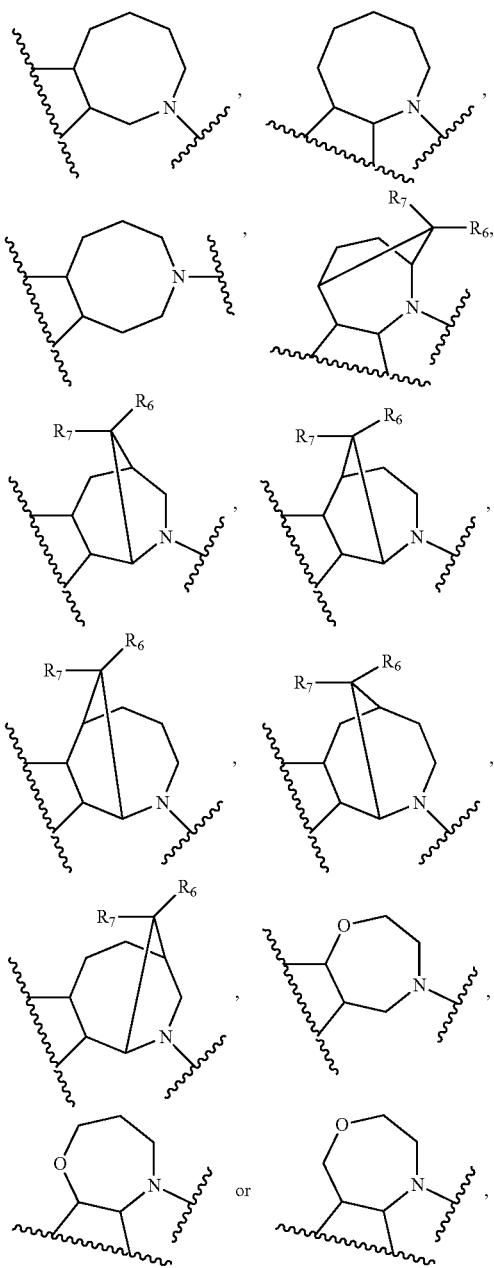

ring A is a benzene ring or a saturated or unsaturated heterocyclic containing 1 to 2 heteroatoms selected from N, S or O; wherein, $R_6$ and $R_7$ are independently hydrogen, halogen, $C_{1-6}$ alkyl, $C_{1-6}$ alkoxy, halogenated $C_{1-6}$ alkyl, $C_{1-6}$ alkylamino, halogenated $C_{1-6}$ alkoxy or $C_{3-6}$ cycloalkyl;

$R_1$ is a substituent on ring A;
$R_2$ is a substituent on ring B;
$R_3$ and $R_4$ are substituents on six-membered ring;
$R_1$, $R_2$, $R_3$ and $R_4$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkylamino;
Y is N or CH;
Z is O or $(CH_2)_n$, n is an integer from 1 to 6;
$R_5$ is $C_{1-6}$ alkyl, $C_{3-6}$ cycloalkyl, $C_{3-6}$ cycloalkenyl, $C_{2-6}$ alkenyl or $C_{2-6}$ alkynyl, wherein the $C_{1-6}$ alkyl, $C_{3-6}$ cycloalkyl, $C_{3-6}$ cycloalkenyl, $C_{2-6}$ alkenyl or $C_{2-6}$ alkynyl are optionally substituted with one or more substituents selected from halogen, nitro, cyano, amine or hydroxyl.

In another preferred embodiment, when ring B is

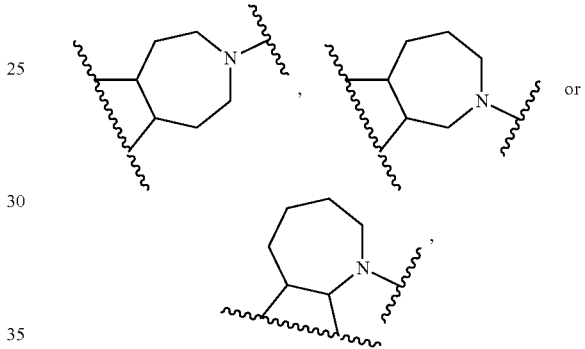

ring A is a saturated or unsaturated heterocyclic containing 1 to 2 heteroatoms selected from N, S or O;

when ring B is

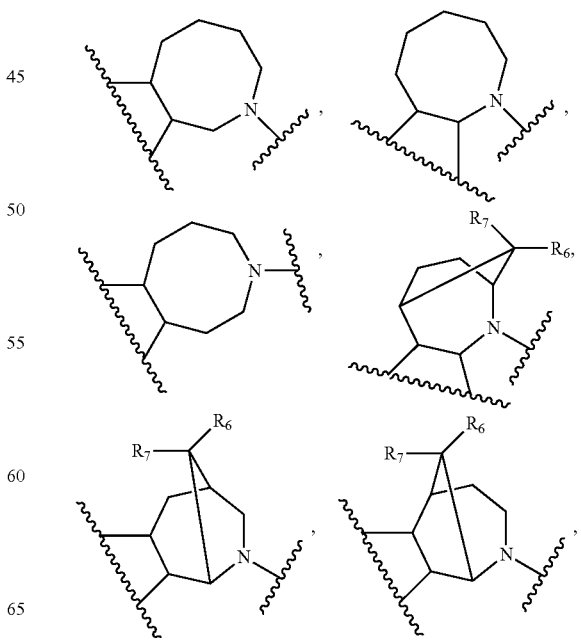

-continued

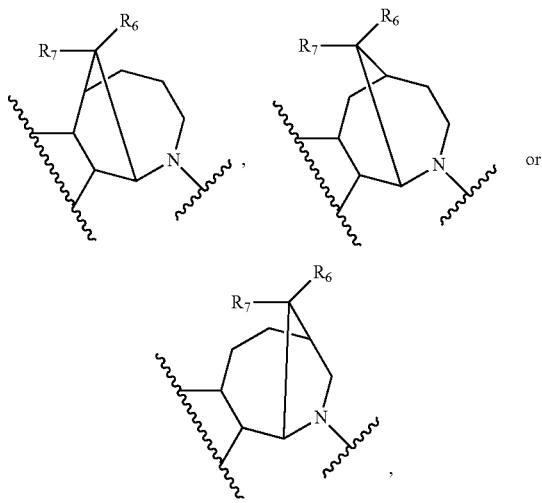

ring A is a benzene ring or a saturated or unsaturated heterocyclic containing 1 to 2 heteroatoms selected from N, S or O; wherein, $R_6$ and $R_7$ are independently hydrogen, halogen, $C_{1-6}$ alkyl, $C_{1-6}$ alkoxy, halogenated $C_{1-6}$ alkyl, $C_{1-6}$ alkylamino, halogenated $C_{1-6}$ alkoxy, $C_{3-6}$ cycloalkyl;

$R_1$ is a substituent on ring A;

$R_2$ is a substituent on ring B;

$R_3$ and $R_4$ are substituents on six-membered ring;

$R_1$, $R_2$, $R_3$ and $R_4$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkaneamino;

Y is N or CH;

Z is O or $(CH_2)_n$, n is an integer from 1 to 6;

$R_5$ is $C_{1-6}$ alkyl, $C_{3-6}$ cycloalkyl, $C_{3-6}$ cycloalkenyl, $C_{2-6}$ alkenyl or $C_{2-6}$ alkynyl, wherein the $C_{1-6}$ alkyl, $C_{3-6}$ cycloalkyl, $C_{3-6}$ cycloalkenyl, $C_{2-6}$ alkenyl or $C_{2-6}$ alkynyl are optionally substituted with one or more substituents selected from halogen, nitro, cyano, amine or hydroxyl.

In another preferred embodiment, when ring B is

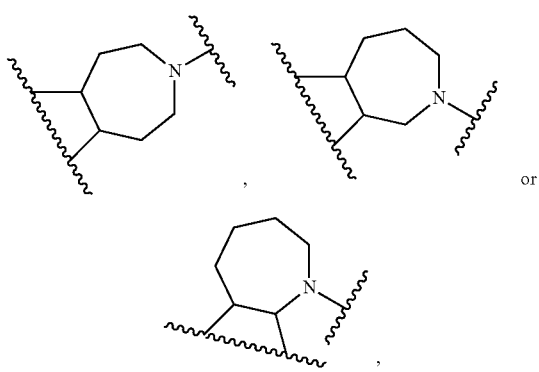

ring A is a saturated or unsaturated heterocyclic containing 1 to 2 heteroatoms selected from N, S or O;

when ring B is

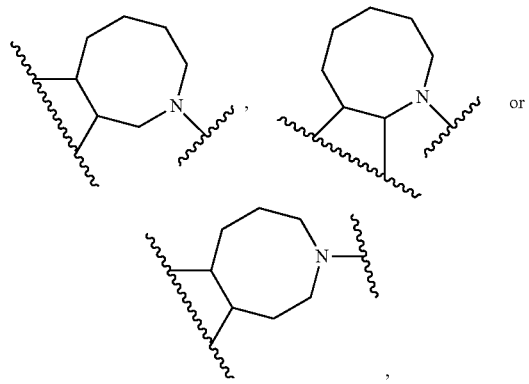

ring A is a benzene ring or a saturated or unsaturated heterocyclic containing 1 to 2 heteroatoms selected from N, S or O;

$R_1$ is a substituent on ring A;

$R_2$ is a substituent on ring B;

$R_3$ and $R_4$ are substituents on six-membered ring;

$R_1$, $R_2$, $R_3$ and $R_4$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkaneamino;

Y is N or CH;

Z is O or $(CH_2)_n$, n is an integer from 1 to 6;

$R_5$ is $C_{1-6}$ alkyl, $C_{3-6}$ cycloalkyl, $C_{3-6}$ cycloalkenyl, $C_{2-6}$ alkenyl or $C_{2-6}$ alkynyl, wherein the $C_{1-6}$ alkyl, $C_{3-6}$ cycloalkyl, $C_{3-6}$ cycloalkenyl, $C_{2-6}$ alkenyl or $C_{2-6}$ alkynyl are optionally substituted with one or more substituents selected from halogen, nitro, cyano, amine or hydroxyl.

In another preferred embodiment, when ring B is

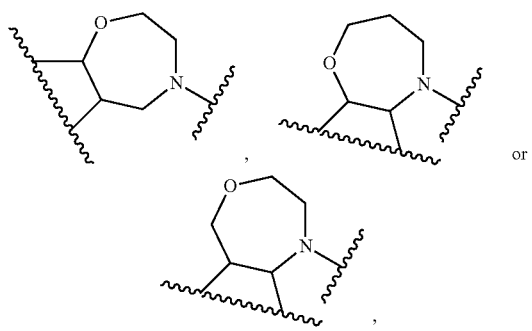

ring A is a benzene ring or a saturated or unsaturated heterocyclic containing 1 to 2 heteroatoms selected from N, S or O;

$R_1$ is a substituent on ring A;

$R_2$ is a substituent on ring B;

$R_3$ and $R_4$ are substituents on six-membered ring;

$R_1$, $R_2$, $R_3$ and $R_4$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkylamino;

Y is N or CH;

Z is O or $(CH_2)_n$, n is an integer from 1 to 6;

$R_5$ is $C_{1-6}$ alkyl, $C_{3-6}$ cycloalkyl, $C_{3-6}$ cycloalkenyl, $C_{2-6}$ alkenyl or $C_{2-6}$ alkynyl, wherein the $C_{1-6}$ alkyl, $C_{3-6}$ cycloalkyl, $C_{3-6}$ cycloalkenyl, $C_{2-6}$ alkenyl or $C_{2-6}$ alkynyl are optionally substituted with one or more substituents selected from halogen, nitro, cyano, amine or hydroxyl.

In another preferred embodiment, when ring B is

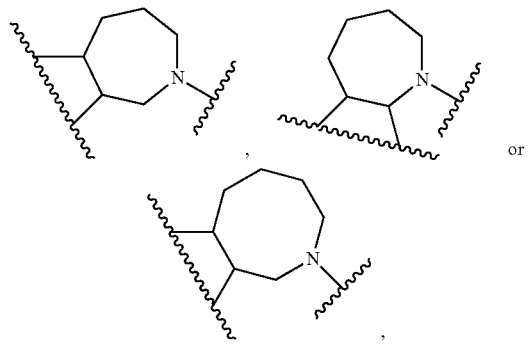

, or ring A is a thiophene ring;

$R_1$ is a substituent on ring A;

$R_2$ is a substituent on ring B;

$R_3$ and $R_4$ are substituents on six-membered ring;

$R_1$, $R_2$, $R_3$ and $R_4$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkaneamino;

Y is CH;

Z is $CH_2$;

$R_5$ is $C_{1-6}$ alkyl.

In another preferred embodiment, when ring B is

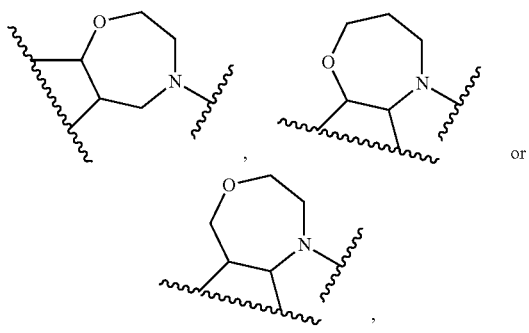

, or ring A is a benzene ring;

$R_1$ is a substituent on ring A;

$R_2$ is a substituent on ring B;

$R_3$ and $R_4$ are substituents on six-membered ring;

$R_1$, $R_2$, $R_3$ and $R_4$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkaneamino;

Y is CH;

Z is $CH_2$;

$R_5$ is $C_{1-6}$ alkyl.

In another preferred embodiment, when ring B is

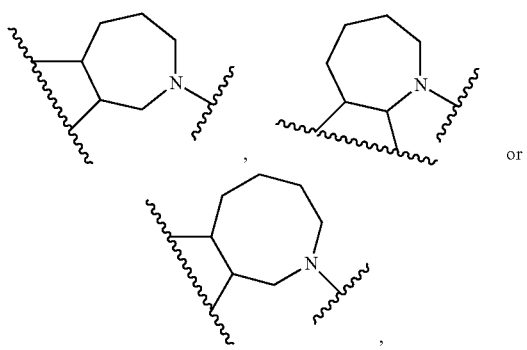

, or ring A is a thiophene ring;

$R_1$ is a substituent on ring A;

$R_2$ is a substituent on ring B;

$R_3$ and $R_4$ are substituents on six-membered ring;

$R_1$ is hydrogen, halogen, $C_{1-6}$ alkyl, $C_{1-6}$ alkoxy, halogenated $C_{1-6}$ alkyl, halogenated $C_{1-6}$ alkoxy, $C_{3-6}$ cycloalkyl or $C_{1-6}$ alkylamino;

$R_2$ is hydrogen;

$R_3$ and $R_4$ are each independently $C_{1-6}$ alkyl;

Y is CH;

Z is $CH_2$;

$R_5$ is $C_{1-6}$ alkyl.

In another preferred embodiment, when ring B is

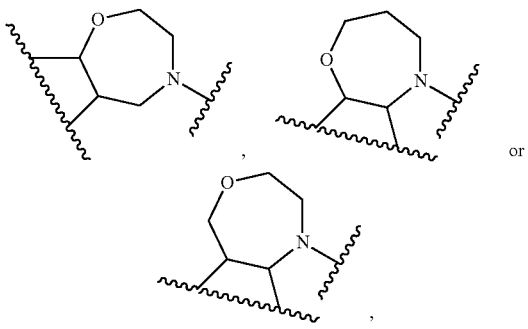

, or ring A is a benzene ring;

$R_1$ is a substituent on ring A;

$R_2$ is a substituent on ring B;

$R_3$ and $R_4$ are substituents on six-membered ring;

$R_1$ is hydrogen, halogen, $C_{1-6}$ alkyl, $C_{1-6}$ alkoxy, halogenated $C_{1-6}$ alkyl, halogenated $C_{1-6}$ alkoxy, $C_{3-6}$ cycloalkyl or $C_{1-6}$ alkylamino;

$R_2$ is hydrogen;

$R_3$ and $R_4$ are each independently $C_{1-6}$ alkyl;

Y is CH;

Z is $CH_2$;

$R_5$ is $C_{1-6}$ alkyl.

In another preferred embodiment, when ring B is

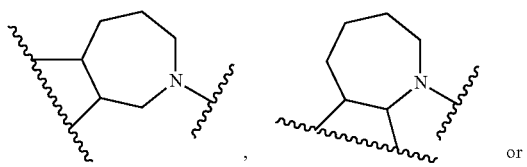

, or

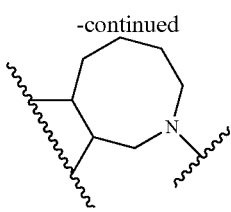

ring A is a thiophene ring;
R₁ is a substituent on ring A;
R₂ is a substituent on ring B;
R₃ and R₄ are substituents on six-membered ring;
R₁ is hydrogen, halogen or $C_{1-6}$ alkyl;
R₂ is hydrogen;
R₃ and R₄ are each independently $C_{1-6}$ alkyl;
Y is CH;
Z is $CH_2$;
R₅ is $C_{1-6}$ alkyl.
In another preferred embodiment, when ring B is

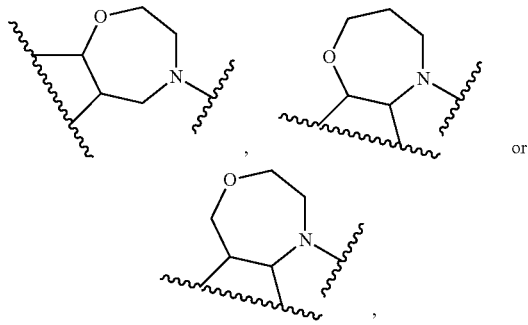

ring A is a benzene ring;
R₁ is a substituent on ring A;
R₂ is a substituent on ring B;
R₃ and R₄ are substituents on six-membered ring;
R₁ is hydrogen, halogen or $C_{1-6}$ alkyl;
R₂ is hydrogen;
R₃ and R₄ are each independently $C_{1-6}$ alkyl;
Y is CH;
Z is $CH_2$;
R₅ is $C_{1-6}$ alkyl.
In another preferred embodiment, R₁ is hydrogen, halogen or $C_{1-6}$ alkyl.
In another preferred embodiment, R₂ is hydrogen.
In another preferred embodiment, R₃ is $C_{1-6}$ alkyl, preferably methyl.
In another preferred embodiment, R₄ is $C_{1-6}$ alkyl, preferably methyl.
In another preferred embodiment, R₃ and R₄ are substituents at positions other than Y on six-membered ring.
In another preferred embodiment, Y is CH.
In another preferred embodiment, Z is $CH_2$.
In another preferred embodiment, R₅ is $C_{1-6}$ alkyl, preferably isobutyl.
In another preferred embodiment, the saturated or unsaturated heterocyclic containing 1 to 2 heteroatoms selected from N, S or O is selected from the group consisting of pyridine, pyrazine, pyridazine, pyrimidine, thiophene, furan, pyrrole, thiazole and oxazole.
In another preferred embodiment, the saturated or unsaturated heterocyclic containing 1 to 2 heteroatoms selected from N, S or O is a thiophene ring.

In another preferred embodiment, the compound is selected from the group consisting of:

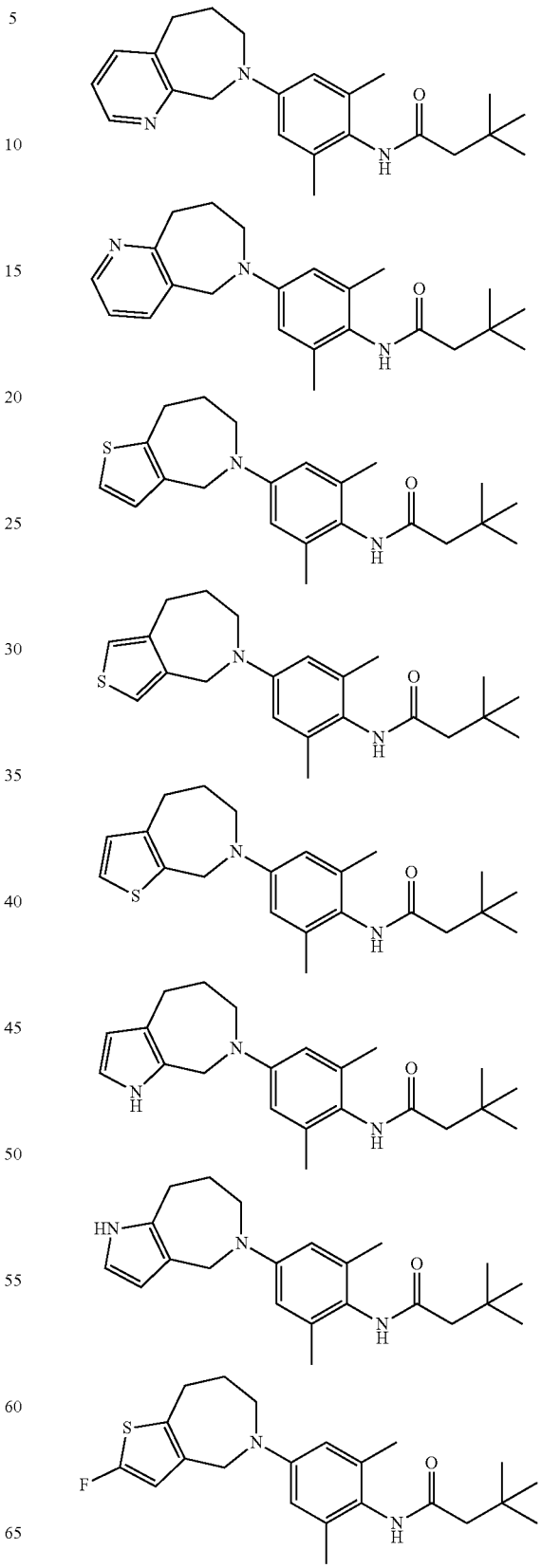

-continued
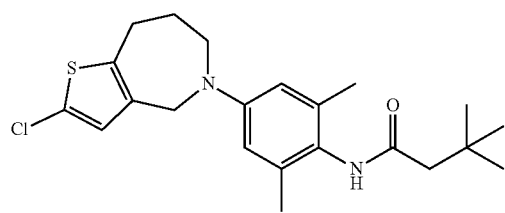
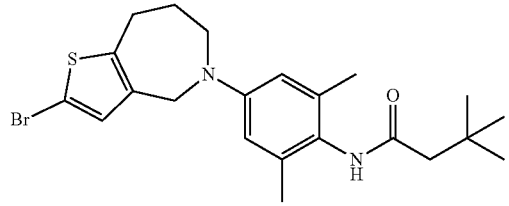
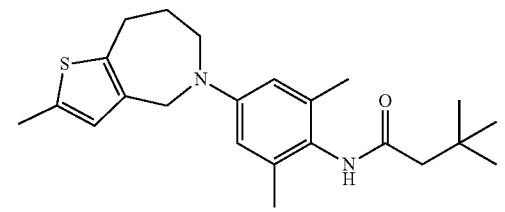
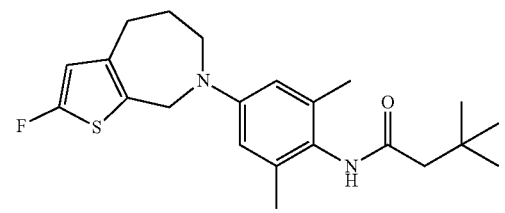
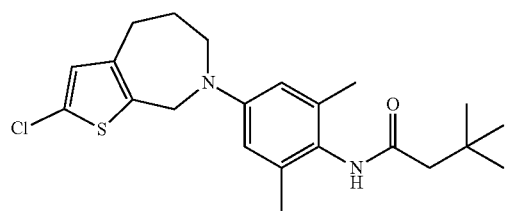
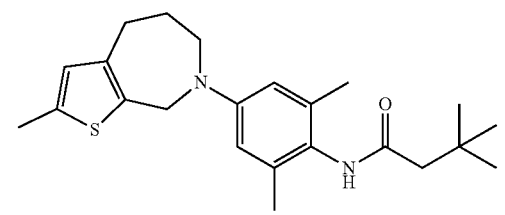
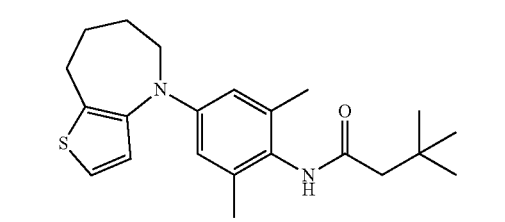
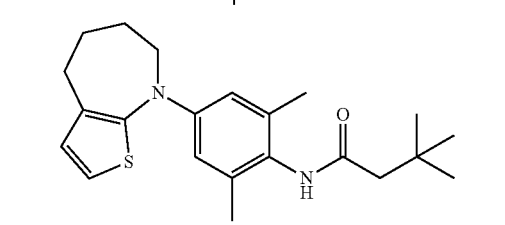
-continued
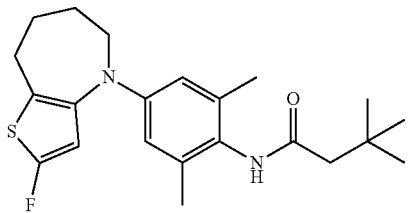
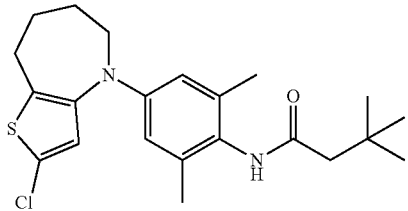
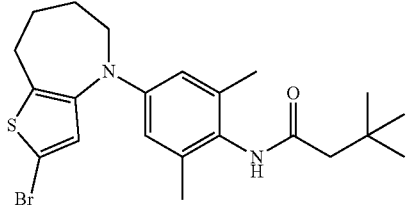
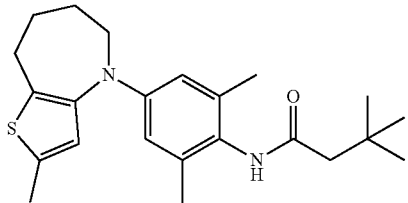
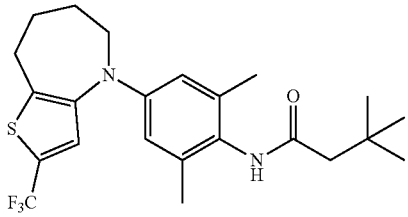
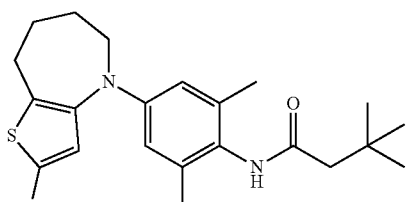
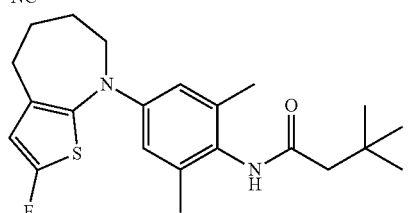
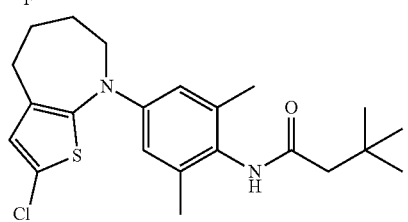

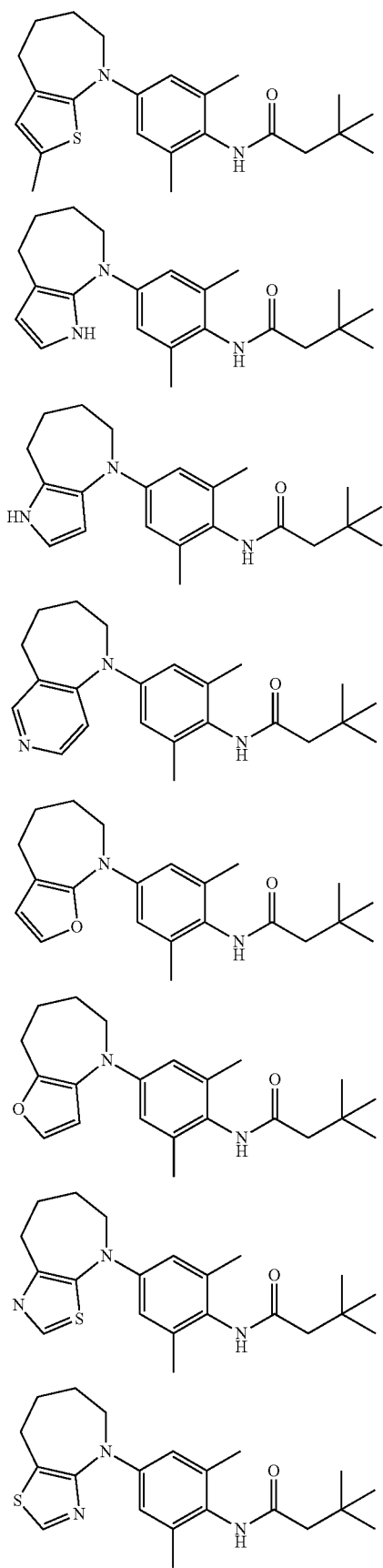
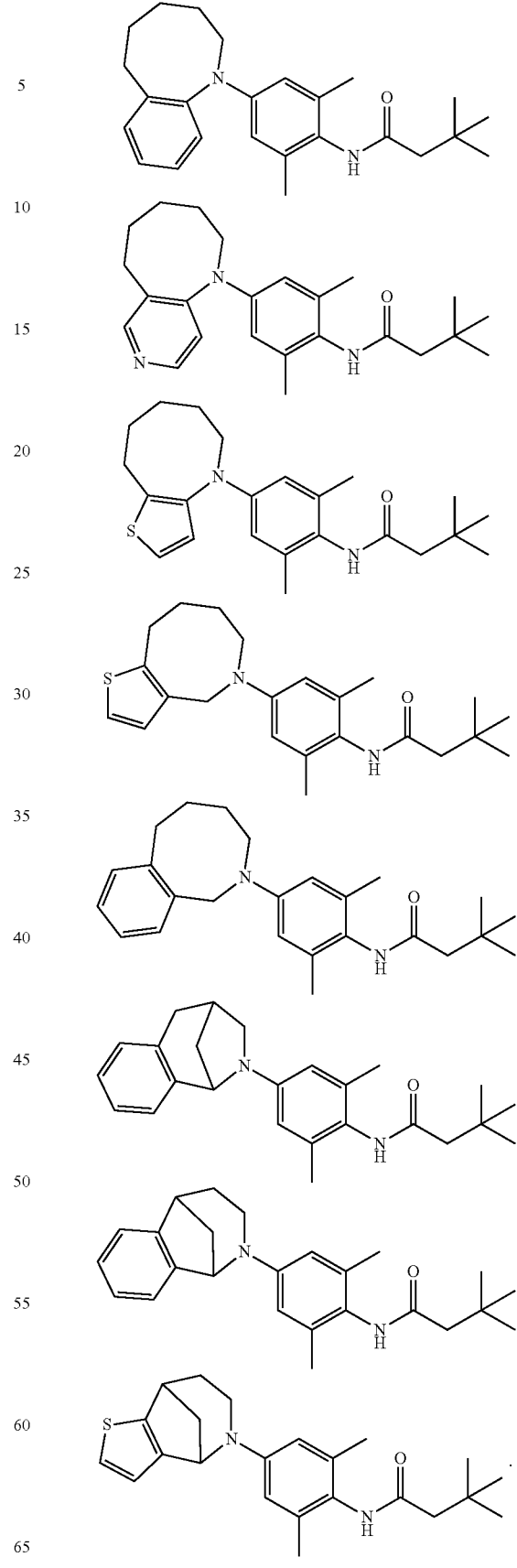

In another preferred embodiment, the compound is selected from the group consisting of:
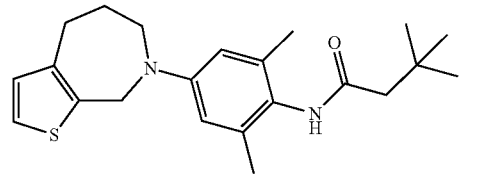
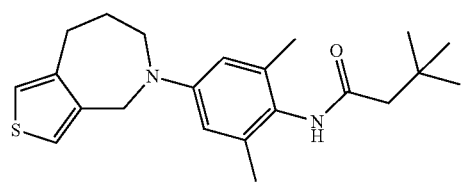
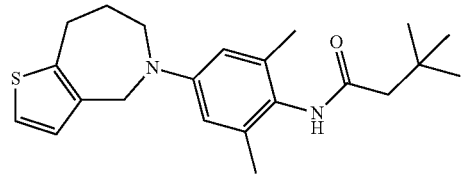
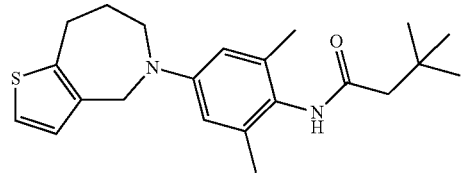
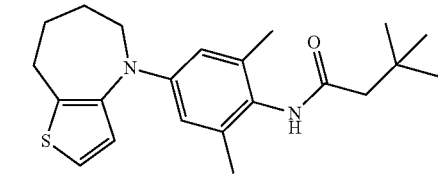
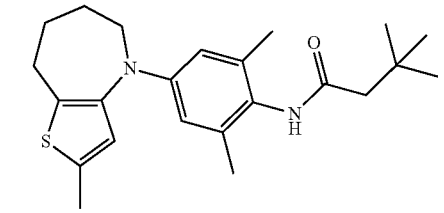
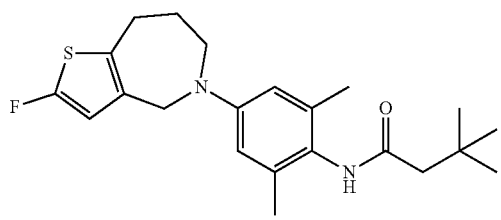
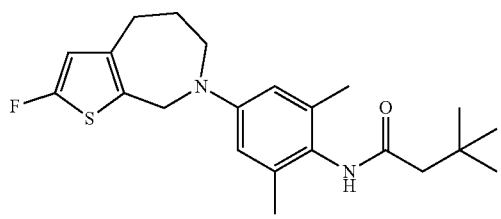
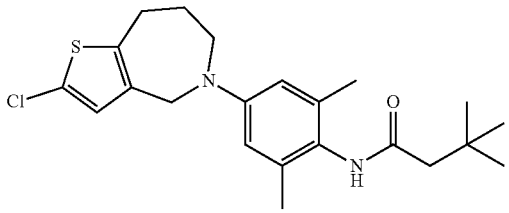
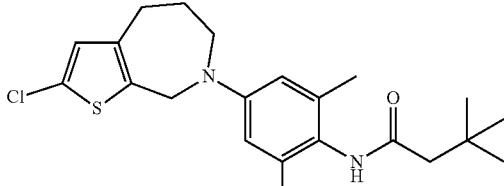
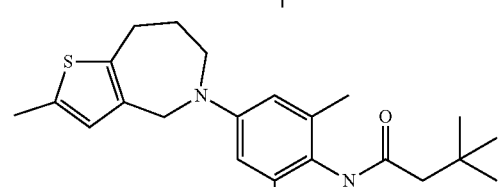
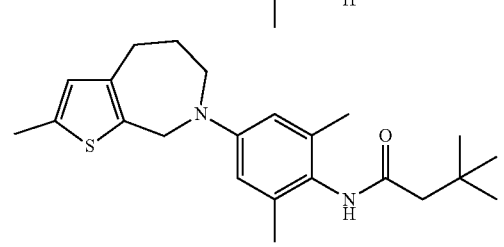
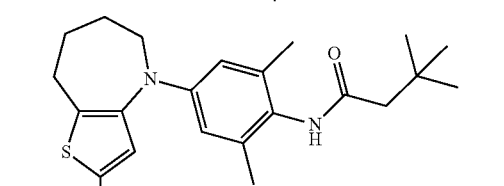
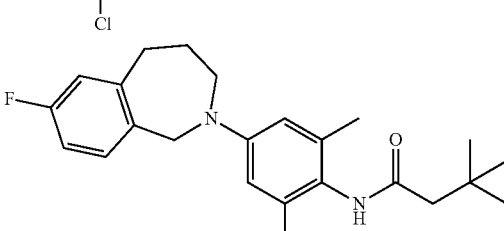
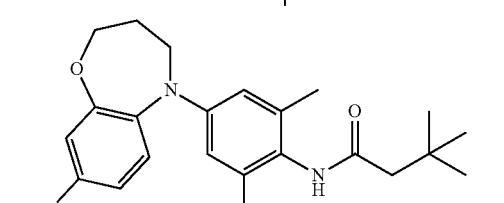
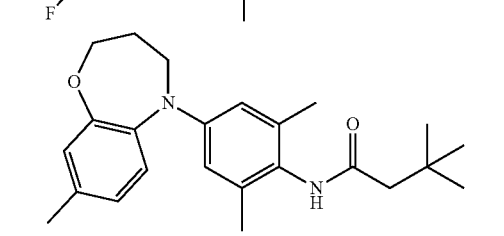

-continued

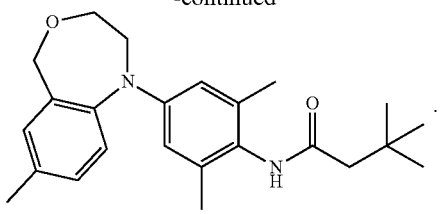

In the second aspect of the invention, it provides a pharmaceutical composition comprising one or more pharmaceutically acceptable carriers or diluents and the compound according to the first aspect of the present invention or a pharmaceutically acceptable salt thereof.

In the third aspect of the present invention, it provides a use of the compound according to the first aspect of the present invention or a pharmaceutically acceptable salt thereof or the pharmaceutical composition according to the second aspect of the present invention for the preparation of a medicament regulating (for example, up-regulating or down-regulating) ion current in potassium channels in mammal.

In the third aspect of the present invention, it provides a use of the compound according to the first aspect of the present invention or a pharmaceutically acceptable salt thereof or the pharmaceutical composition according to the second aspect of the present invention for the preparation of a medicament for the prevention, treatment or inhibition of disorder or condition in response to abnormal (e.g., increased or decreased) ion flow in potassium channel.

In another preferred embodiment, the disease or condition is selected from the group consisting of a disease or condition of the central nervous system, pain, stroke, neurodegenerative condition, and neuronal hyperexcitability.

In another preferred embodiment, the disorder or condition of the central nervous system is an seizure symptoms; and/or
  the pain is selected from the group consisting of inflammatory pain, neuropathic pain, migraine pain conditions, allodynia, hyperalgesic pain, phantom pain, and cancer-related pain; and/or
  the neurodegenerative disorder is selected from the group consisting of Alzheimer's disease, Huntington's disease, multiple sclerosis, amyotrophic lateral sclerosis, AIDS-induced encephalopathy and Creutzfeld-Jakob disease, Parkinson's disease, trauma-induced neurodegeneration, other infection-related encephalopathy induced by rubella virus, herpes virus, borrelia and unknown pathogen; and/or
  the neuronal hyperexcitability is a state in drug withdrawal or poisoning.

In another preferred embodiment, the seizure symptoms include convulsions, epilepsy and status epilepticus.

In another preferred embodiment, the neuropathic pain is neuropathic pain related to diabetic neuropathy or neuropathic pain related to migraine.

The present invention provides a method for preparing the compound represented by formula A or a pharmaceutically acceptable salt thereof, but is not limited to the following methods:

Route 1:

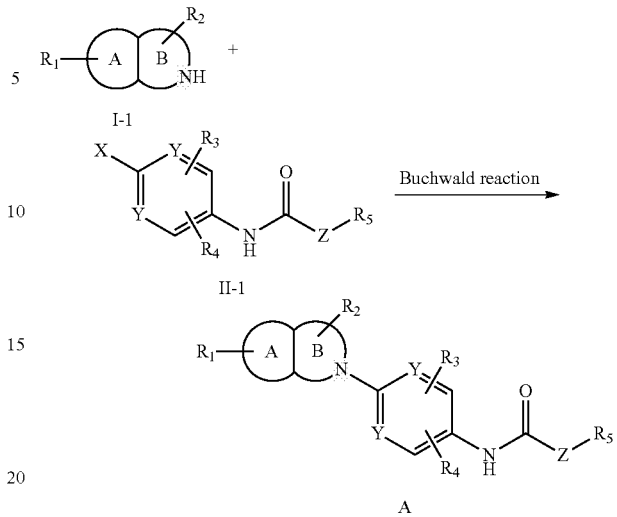

Compound I-1 and compound II-1 undergo Buchwald reaction to obtain compound A;

In Route 1, X is Cl, Br, I, OTf or $B(OH)_2$; A, B, $R_1$, $R_2$, $R_3$, $R_4$, $R_5$, Y, and Z are defined as in formula A.

Route 2:

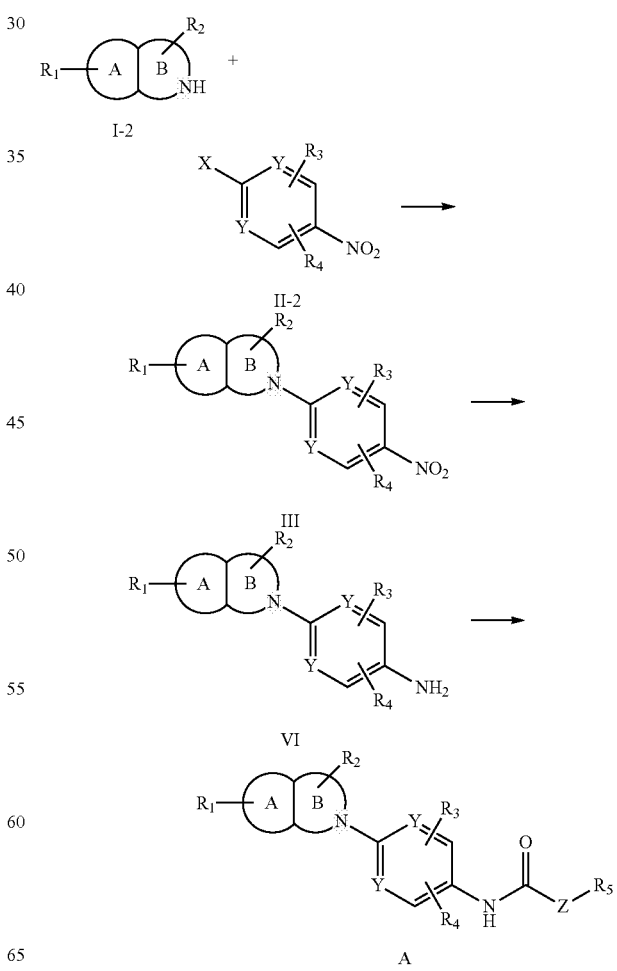

Compound I-2 and compound II-2 undergo a nucleophilic substitution reaction to obtain compound III;

Compound III undergoes nitro reduction reaction to obtain compound VI;

Compound VI is further acylated to obtain compound A;

In Route 2, X is F or Cl; A, B, $R_1$, $R_2$, $R_3$, $R_4$, $R_5$, Y, and Z are as defined in formula A.

It should be understood that within the scope of the present invention, the above-mentioned technical features of the present invention and the technical features specifically described in the following (e.g. Examples) can be combined with each other to form a new or preferred technical solutions. which will not redundantly be described one by one herein.

DETAILED DESCRIPTION OF THE INVENTION

Through extensive and intensive research, the inventors have unexpectedly discovered for the first time a class of p-diaminobenzene compounds with novel structures as potassium ion channel openers. The compounds of the present invention have excellent KCNQ2/3 opening activity and can be used for the treatment of pain, epilepsy, stroke and other diseases. Based on above discovery, the present invention has been completed.

Terms

Unless otherwise specified, the "or" mentioned in this article has the same meaning as "and/or" (refers to "or" and "and").

Unless otherwise specified, in all compounds of the present invention, each chiral carbon atom (chiral center) may optionally be in the R configuration or the S configuration, or a mixture of R configuration and S configuration.

As used herein, when alone or as part of other substituents, the term "alkyl" refers to a straight chain containing only carbon atoms (i.e., unbranched) or a branched saturated hydrocarbon group, or groups combined by straight chain with branches. When the alkyl group has a limited number of carbon atoms in front of it (such as $C_{1-6}$ alkyl), it means that the alkyl group contains 1-6 carbon atoms, including for example methyl, ethyl, propyl, isopropyl, butyl, isobutyl, sec-butyl, tert-butyl, or similar groups.

As used herein, when alone or as part of other substituents, the term "$C_{1-6}$ alkoxy" refers to $C_{1-6}$ alkyl-O—, including for example methoxy, ethoxy, propoxy, isopropoxy, butoxy, isobutoxy, sec-butoxy, tert-butoxy, or similar groups.

As used herein, when alone or as part of other substituents, the term "$C_{3-6}$ cycloalkyl" refers to a cyclic alkyl group having 3-6 carbon atoms, including for example cyclopropyl, cyclobutyl, cyclopentyl, cyclohexyl, or similar groups.

As used herein, when alone or as part of other substituents, the term "$C_{3-6}$ cycloalkenyl" refers to a cyclic alkenyl group having 3-6 carbon atoms, which may have one or two alkenyl groups, including for example cyclobutenyl, cyclopentenyl, cyclohexenyl, or similar groups.

As used herein, when alone or as part of other substituents, the term "$C_{2-6}$ alkenyl" refers to a straight or branched chain alkenyl group having 3-6 carbon atoms, which may have one or more alkenyl groups, including for example vinyl, propenyl, butenyl, or similar groups.

As used herein, when alone or as part of other substituents, the term "$C_{2-6}$ alkynyl" refers to a branched or unbranched alkynyl group having 2-6 carbon atoms, which may have one or more alkynyl group, including for example ethynyl, propynyl, butynyl, or similar groups.

As used herein, "halogen" is fluorine, chlorine, bromine or iodine.

As used herein, "halogenated" means fluoro, chloro, bromo or iodo.

Active Ingredient

The compound of the present invention refers to the compound represented by the general formula A or its stereoisomer or optical isomer, or its pharmaceutically acceptable salt.

The "pharmaceutically acceptable salt" refers to the salt formed by the compound of the present invention and pharmaceutically acceptable inorganic acid and organic acid, wherein the preferred inorganic acid includes (but not limited to): hydrochloric acid, hydrobromic acid, phosphoric acid, nitric acid, sulfuric acid, trifluoroacetic acid (TFA); preferred organic acids include (but not limited to): formic acid, acetic acid, propionic acid, succinic acid, naphthalene sulfonic acid (1,5), asiatic acid, oxalic acid, tartaric acid, lactic acid, salicylic acid, benzoic acid, valeric acid, diethyl acetic acid, malonic acid, succinic acid, fumaric acid, pimelic acid, adipic acid, maleic acid, malic acid, sulfamic acid, phenylpropionic acid, gluconic acid, ascorbic acid, niacin, isonicotinic acid, methanesulfonic acid, p-toluenesulfonic acid, citric acid, and amino acids.

The "stereoisomer" or "optical isomer" means that the chiral carbon atom involved in the compound of the present invention can be in the R configuration or S configuration, or a combination thereof.

Pharmaceutical Composition and Method for Administration

Because the compound of the present invention has excellent KCNQ2/3 opening activity, the compound of the present invention and the pharmaceutical composition containing the compound of the present invention as the main active ingredient can be used to treat, prevent and alleviate diseases related to potassium ion channels. According to the prior art, the compounds of the present invention can be used to treat the following diseases (but not limited to): epilepsy, inflammatory pain, neuropathic pain, migraine, insomnia, neurodegenerative diseases, anxiety disorders, stroke, cocaine abuse, nicotine withdrawal, alcohol withdrawal or tinnitus, etc.

The pharmaceutical composition of the present invention contains a safe and effective amount of the compound of the present invention and a pharmacologically acceptable excipient or carrier.

The "safe and effective amount" refers to that the amount of the compound is sufficient to significantly improve the condition without causing serious side effects. Usually, the pharmaceutical composition contains 1-2000 mg of the compound of the present invention/agent, and more preferably, 5-200 mg of the compound of the present invention/agent. Preferably, the "one dosage" is a capsule or a tablet.

The "pharmaceutically acceptable carrier" refers to: one or more compatible solid or liquid fillers or gel substances, which are suitable for human use, and must have sufficient purity and low enough toxicity. The "compatible" herein means that the components in the composition can be blended with the compound of the present invention and between them without significantly reducing the efficacy of the compound. Pharmaceutically acceptable carriers include cellulose and its derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oil (such as soybean oil, sesame oil, peanut oil, olive oil, etc.), polyol (such as propylene glycol, glycerin, mannitol, sorbitol, etc.), emulsifiers (such as Tween®), wetting agents (such as sodium lauryl sulfate), coloring agents, flavoring agents, stabilizers, antioxidants, preservatives, pyrogen-free water, etc.

The administration method of the compound or the pharmaceutical composition of the present invention is not particularly limited. Representative administration methods include (but not limited to): oral, rectal, parenteral (intravenous, intramuscular or subcutaneous) and topical administration.

Solid dosage forms for oral administration include capsules, tablets, pills, powders and granules. In these solid dosage forms, the active compound is mixed with at least one conventional inert excipient (or carrier), such as sodium citrate or dicalcium phosphate, or mixed with the following ingredients: (a) filler or compatibilizers, such as starch, lactose, sucrose, glucose, mannitol and silicic acid; (b) binders, such as hydroxymethylcellulose, alginate, gelatin, polyvinylpyrrolidone, sucrose and arabic gum; (c) humectant, for example, glycerin; (d) disintegrant, for example, agar, calcium carbonate, potato starch or tapioca starch, alginic acid, certain complex silicates, and sodium carbonate; (e) relieving solvent, such as paraffin; (f) absorption accelerator, such as quaternary amine compound; (g) wetting agent, such as cetyl alcohol and glyceryl monostearate; (h) adsorbent, for example, kaolin; and (i) lubricant, for example, talc, calcium stearate, magnesium stearate, solid polyethylene glycol, sodium lauryl sulfate, or mixtures thereof. In capsules, tablets and pills, the dosage forms may also contain buffering agents.

Solid dosage forms such as tablets, dragees, capsules, pills and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances.

In addition to these inert diluents, the compositions may contain adjuvants such as wetting agents, emulsifying and suspending agents, sweetening agents, flavoring agents and spices.

In addition to the active compound, the suspension may contain suspending agent, for example, ethoxylated isooctadecanol, polyoxyethylene sorbitol and dehydrated sorbitan ester, microcrystalline cellulose, aluminum methoxide and agar, or the mixture thereof etc.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof. Dosage forms for the compounds of the invention for topical administration include ointments, powders, patches, propellants and inhalants. The active ingredient is mixed under sterile conditions with a physiologically acceptable carrier and any preservatives, buffers, or propellants which may be required if necessary.

The compounds of the invention may be administered alone or in combination with other pharmaceutically acceptable compounds.

When the pharmaceutical composition is used, a safe and effective amount of the compound of the present invention is applied to a mammal in need of treatment (such as a human), wherein the dosage at the time of administration is the pharmaceutically effective dosage, for people having a body weight of 60 kg, the daily dose is usually 1-2000 mg, preferably 5-500 mg. Of course, specific doses should also consider factors such as the administration route, the health of the patient, etc., which are within the skill of the skilled physician.

The Main Advantages of the Invention Comprise:

The present invention provides a kind of potassium ion channel opener compound with novel structure. The compounds of the invention have excellent potassium ion channel opening activity and also have good safety.

The compounds of the present invention are expected to be used in the treatment and prevention of diseases and disorders affected by the activity of potassium ion channels.

The compounds of the invention have better potassium ion channel opening activity, better pharmacokinetic properties, better cerebral blood ratio and better safety.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless otherwise stated, percentages and parts are percentages by weight and parts by weight.

The experimental materials and reagents used in the following examples can be obtained from commercial sources unless otherwise specified.

Example 1 Preparation of Compound 03026

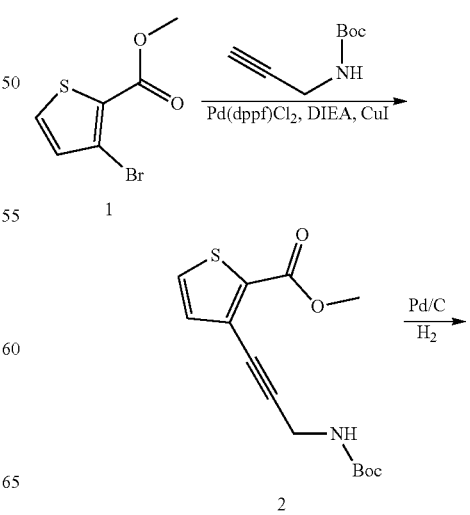

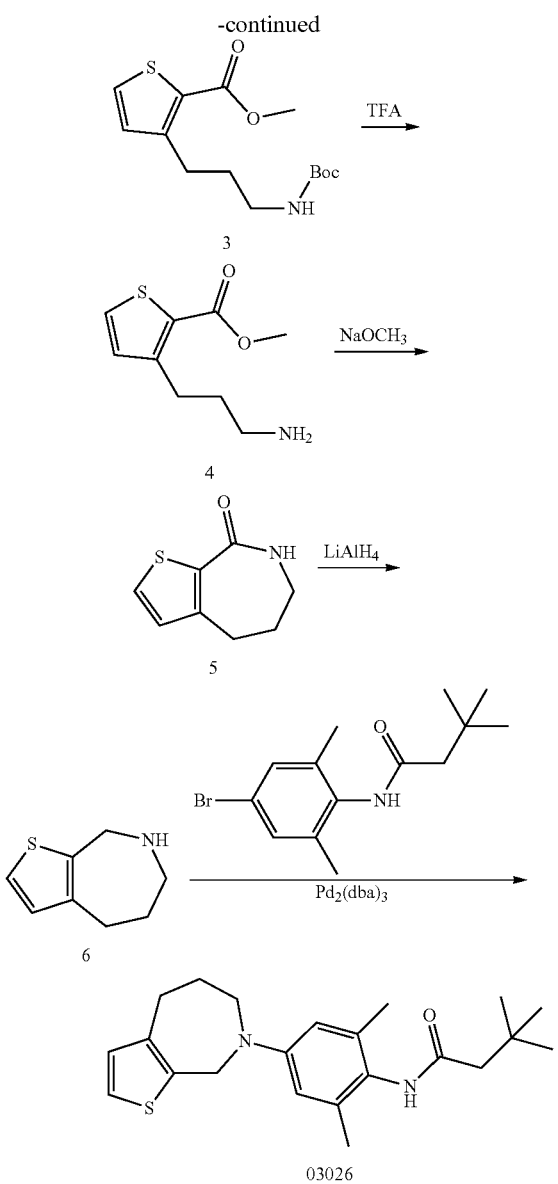

Step One: 3-(3-((tert-butoxycarbonyl) amino)-1-propynyl)-2-methyl thiophenecarboxylate (Compound 2)

(1,1'-bis (diphenylphosphino) ferrocene) palladium dichloride (0.42 g, 0.57 mmol) and cuprous iodide (0.217 g, 1.14 mmol) were added into a solution of 3-bromo-2-thiophene methyl formate (2.5 g, 11.3 mmol), N-tert-butoxycarbonylaminopropyne (2.1 g, 13.6 mmol) and diisopropylethylamine (3 mL) in acetonitrile (30 mL), and the resulting mixture was heated to reflux and stirred overnight under the protection of nitrogen. The reaction solution was cooled to room temperature, filtered with celite, the filtrate was concentrated to remove the solvent, and the residue was purified with a silica gel column to obtain a yellow oily compound 2 (2.0 g, yield: 59.5%).

MS (ESI): Calcd. for $C_{14}H_{17}NO_4S$ 295; Found 318 [M+Na]+.

Step Two: 3-(3-((tert-butoxycarbonyl) amino)-propyl)-2-methyl thiophenecarboxylate (Compound 3)

10% palladium carbon (0.2 g) was added into a solution of 3-(3-((tert-butoxycarbonyl)amino)-1-propynyl)-2-methyl thiophenecarboxylate (2.0 g, 6.8 mmol) in tetrahydrofuran (30 mL), and the reaction mixture was stirred overnight under 4 atm hydrogen, filtered and concentrated to obtain a light yellow oily compound 3 (1.8 g, yield: 90.3%).

MS (ESI): Calcd. for $C_{14}H_{21}NO_4S$ 299; Found 322 [M+Na]+.

Step Three: 3-(3-aminopropyl)-2-thiophene methyl formate (Compound 4)

Trifluoroacetic acid (4.6 g, 40 mmol) was slowly dropped into a solution of 3-(3-((tert-butoxycarbonyl)amino)-propyl)-2-thiophene methyl formate (1.8 g, 6.1 mmol) in dichloromethane (40 mL). The reaction was stirred at room temperature for 3 hours and then directly concentrated to obtain a yellow oily crude compound 4 (1.2 g, yield: 96.5%).

MS (ESI): Calcd. for $C_9H_{13}NO_2S$ 199; Found 200 [M+H]+.

Step Four: 4,5,6,7-tetrahydro-8H-thieno[2,3-c]azepin-8-one (Compound 5)

At room temperature, sodium methoxide (1.1 g) was added into a solution of (3-(3-aminopropyl)-2-methyl thiophenecarboxylate (1.2 g, 6.0 mmol) in methanol (40 mL). The reaction mixture was heated to reflux for 3 hours. The reaction solution was directly concentrated, and the residue was purified with a silica gel column to obtain a yellow oily compound 5 (800 mg, yield: 79.8%).

MS (ESI): Calcd. for $C_8H_9NOS$ 167; Found 168 [M+H]+.

Step Five: 5,6,7,8-tetrahydro-4H-thieno[2,3-c]azepine (Compound 6)

At room temperature, lithium tetrahydroaluminum (410 mg, 10.8 mmol) was slowly added into a solution of 4,5,6,7-tetrahydro-8H-thieno[2,3-c]azepin-8-one (600 mg, 3.6 mmol) in tetrahydrofuran (10 mL). Reaction mixture was heated to reflux for 3 hours. The mixture was quenched with water and methanol, filtered, concentrated, and the residue was purified with a silica gel column to obtain a yellow oily compound 6 (450 mg, yield: 81.7%).

MS (ESI): Calcd. for $C_8H_{11}NS$ 153; Found 154 [M+H]+.

Step Six: N-(2,6-dimethyl-4-(4,5,6,8-tetrahydro-7H-thieno[2,3-c]azepin-7-yl)phenyl)-3,3-dimethylbutanamide (Compound 03026)

The mixed reaction solution of tri(dibenzylideneacetone) dipalladium (20 mg), tricyclohexylphosphorus (0.3 mL 10% solution), 5,6,7,8-tetrahydro-4H-thieno[2,3-c]azepine (100 mg, 0.65 mmol), N-(4-bromo-2,6-dimethylphenyl)-3,3-dimethyl butanamide (386 mg, 1.3 mmol), potassium tert-butoxide (218 mg, 1.95 mmol) and dimethyl sulfoxide (20 mL) was reacted in a microwave reactor at 150° C. for 2 hours. The resulting mixture was diluted with water (25 mL) and extracted with ethyl acetate (30 mL×3). The combined organic phase was dried over anhydrous sodium sulfate, filtered and concentrated. The residue was purified by TLC plate to obtain a white solid compound 03026 (6.35 mg, yield: 2.6%).

HNMR (400 MHz, CD₃OD): δ7.01 (d, J=4.4 Hz, 1H), 6.74 (d, J=4.4 Hz, 1H), 6.63 (s, 2H), 4.65 (s, 2H), 3.94-3.85 (m, 2H), 2.94-2.85 (m, 2H), 2.27 (s, 2H), 2.14 (s, 6H), 1.87-1.78 (m, 2H), 1.13 (s, 9H). MS (ESI): Calcd. for $C_{22}H_{30}N_2OS$ 370; Found 371 [M+H]+. HPLC: 93.3% (214 nm)/94.2% (254 nm).

Example 2 Preparation of Compound 03027

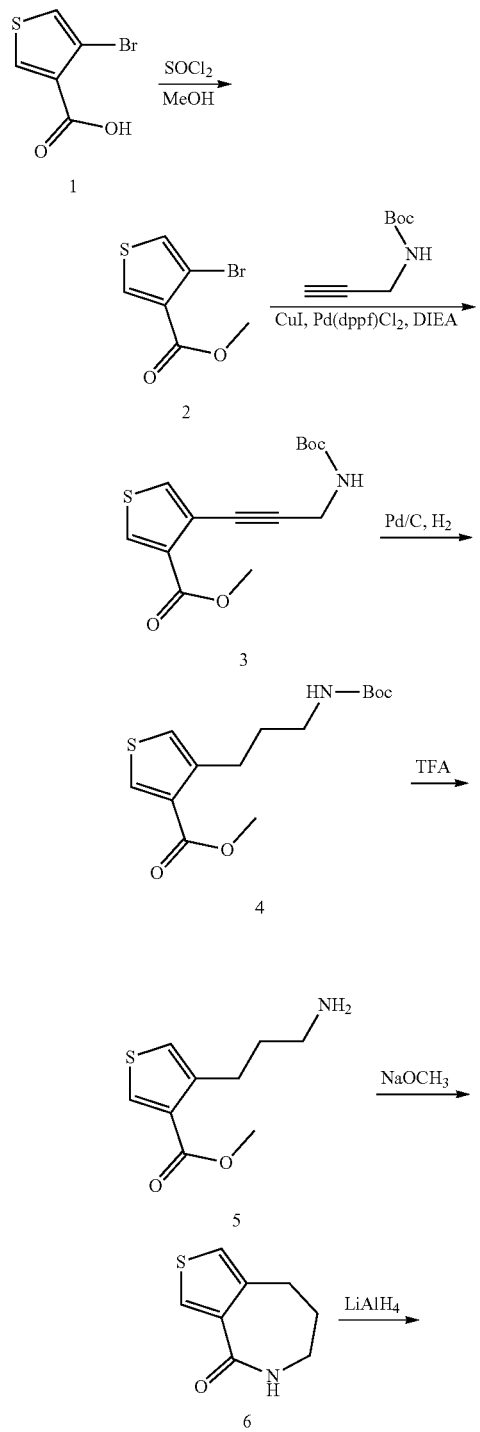

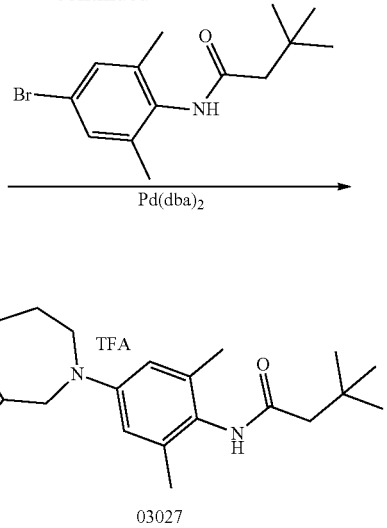

Step One: 4-bromo-3-thiophene methyl formate (Compound 2)

Under ice-cooling, thionyl chloride (2 mL) was slowly added into a solution of 4-bromo-3-thiophene formic acid (2.0 g, 9.7 mmol) in methanol (50 mL), and the reaction mixture was heated to 60 degrees and reacted for 3 hours. The mixture was concentrated in vacuo to give a yellow oily compound 2 (2.2 g, yield: 100%).

MS (ESI): Calcd. for $C_6H_5BrO_2S$ 220; Found 221 [M+H]+.

Step Two: 4-(3-((tert-butoxycarbonyl) amino)-1-propynyl)-3-thiophene methyl formate (Compound 3)

(1,1'-bis (diphenylphosphino) ferrocene) palladium dichloride (0.36 g, 0.5 mmol) and cuprous iodide (0.19 g, 1.0 mmol) were added into a solution of 4-bromo-3-thiophene methyl formate (2.2 g, 10 mmol), N-tert-butoxycarbonylaminopropyne (1.55 g, 10 mmol) and diisopropylethylamine (1.93 g, 15 mmol) in acetonitrile (50 mL), the resulting mixture was heated to reflux and stirred overnight under the protection of nitrogen. The reaction solution was cooled to room temperature, filtered with celite, the filtrate was concentrated to remove the solvent, and the residue was purified with a silica gel column to obtain a yellow oily compound 3 (0.88 g, yield: 29.8%).

MS (ESI): Calcd. for $C_{14}H_{17}NO_4S$ 295; Found 318 [M+Na]+.

Step Three: 4-(3-((tert-butoxycarbonyl) amino)-propyl)-3-thiophene methyl formate (Compound 4)

10% palladium carbon (0.34 g) was added into a solution of 4-(3-((tert-butoxycarbonyl)amino)-1-propynyl)-3-methyl thiophenecarboxylate (0.88 g, 2.95 mmol) in methanol (10 mL), and the reaction mixture was stirred overnight under 4 atm hydrogen, filtered and concentrated to obtain a light yellow oily compound 4 (0.76 g, yield: 86.1%).

MS (ESI): Calcd. for $C_{14}H_{21}NO_4S$ 299; Found 322 [M+Na]+.

Step Four: 4-(3-aminopropyl)-3-thiophene methyl formate (Compound 5)

Trifluoroacetic acid (4.6 g, 40 mmol) was slowly dropped into a solution of 4-(3-((tert-butoxycarbonyl)amino)-propyl)-3-thiophene methyl formate (0.76 g, 2.54 mmol) in dichloromethane (40 mL). The reaction was stirred at room temperature for 3 hours and then directly concentrated to obtain a yellow oily crude compound 5 (0.6 g, yield: 100%).

MS (ESI): Calcd. for $C_9H_{13}NO_2S$ 199; Found 200 [M+H]+.

Step Five: 5,6,7,8-tetrahydro-4H-thieno[3,4-c]azepin-4-one (Compound 6)

At room temperature, sodium methoxide (488 mg) was added into a solution of (4-(3-aminopropyl)-3-methyl thiophenecarboxylate (0.6 g, 3.0 mmol) in methanol (30 mL). The reaction mixture was heated to reflux for 2 hours. The reaction solution was directly concentrated, and the residue was purified with a silica gel column to obtain a yellow oily compound 6 (0.25 g, yield: 49.9%).

MS (ESI): Calcd. for $C_8H_9NOS$ 167; Found 168 [M+H]+.

Step Six: 5,6,7,8-tetrahydro-4H-thieno[3,4-c]azepine (Compound 7)

At room temperature, lithium tetrahydroaluminum (284 mg, 7.5 mmol) was batch added into a solution of 5,6,7,8-tetrahydro-8H-thieno[3,4-c]azepin-4-one (250 mg, 1.5 mmol) in tetrahydrofuran (20 mL). The reaction mixture was heated to reflux for 3 hours. The mixture was quenched with 15% NaOH (1 mL) and filtered with magnesium sulfate. The filtrate was concentrated and purified with a silica gel column to obtain a yellow oily compound 7 (190 mg, yield: 82.8%).

MS (ESI): Calcd. for $C_8H_{11}NS$ 153; Found 154 [M+H]+

Step Seven: N-(2,6-dimethyl-4-(4,6,7,8-tetrahydro-5H-thieno[3,4-c]azepin-5-yl) phenyl)-3,3-dimethylbutanamide (Compound 03027)

The mixed reaction solution of tri(dibenzylideneacetone) dipalladium (5 mgl, 5 μmol), tricyclohexylphosphorus (0.1 mL 10% solution), 5,6,7,8-tetrahydro-4H-thieno[3,4-c] azepine (20 mg, 0.13 mmol), N-(4-bromo-2,6-dimethylphenyl)-3,3-dimethyl butanamide (78 mg, 0.26 mmol), potassium tert-butoxide (44 mg, 0.39 mmol) and dimethyl sulfoxide (2 mL) was reacted in a microwave reactor at 150° C. for 1 hours. The resulting mixture was diluted with water (25 mL) and extracted with ethyl acetate (30 mL×3). The combined organic phase was dried over anhydrous sodium sulfate, filtered and concentrated. The residue was purified with a chromatography plate to obtain a white solid 03027 trifluoroacetate (7.7 mg, yield: 16%).

HNMR (400 MHz, CD3OD): δ7.23 (d, J=2.8 Hz, 1H), 6.88 (d, J=2.8 Hz, 1H), 6.58 (s, 2H), 4.55 (s, 2H), 3.84 (t, J=4.4 Hz, 2H), 2.94-2.88 (m, 2H), 2.27 (s, 2H), 2.14 (s, 6H), 1.82-1.75 (m, 2H), 1.12 (s, 9H). MS (ESI): Calcd. for $C_{22}H_{30}N_2OS$ 370; Found 371 [M+H]+. HPLC: 98.9% (214 nm)/99.6% (254 nm).

Example 3 Preparation of Compound 03028

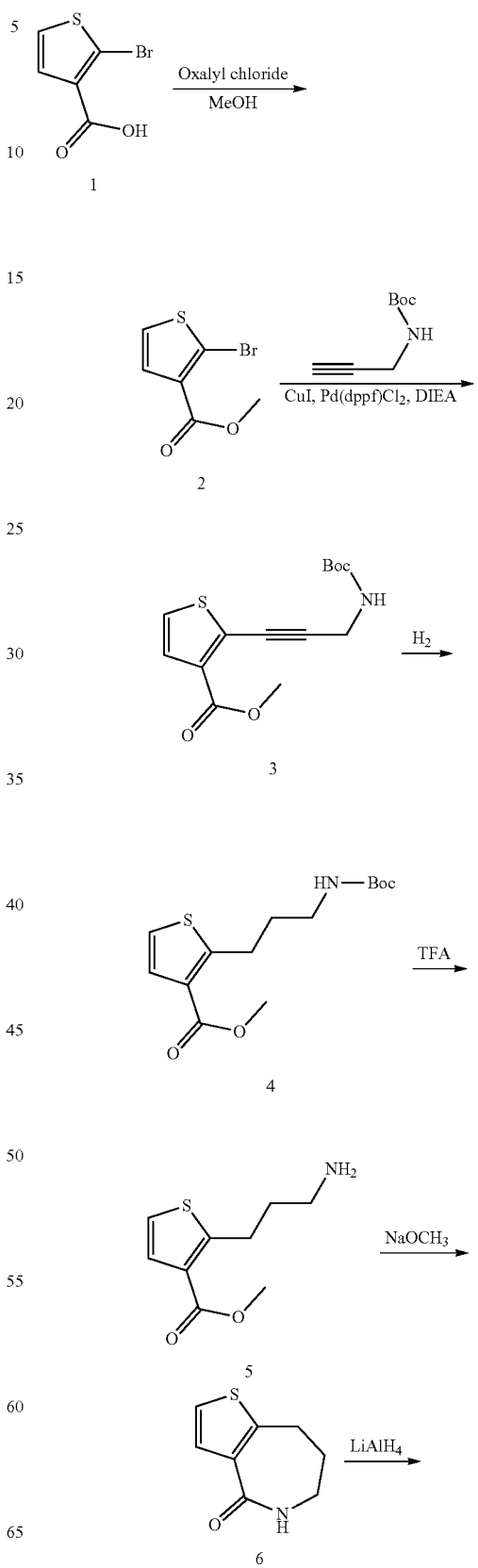

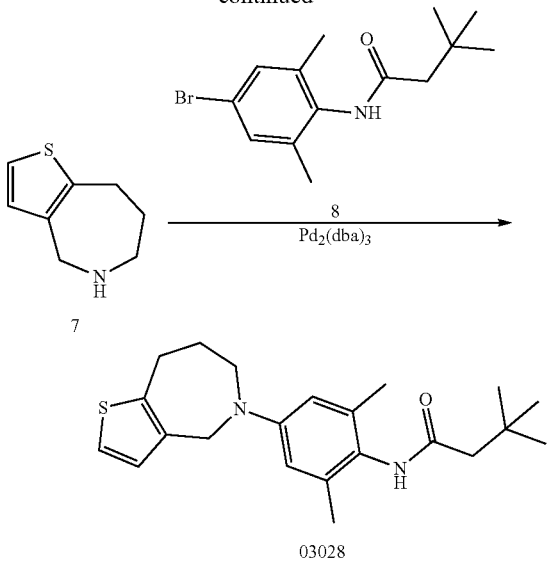

Step One: 2-bromo-3-thiophene methyl formate (Compound 2)

Under ice-cooling, oxalyl chloride (2.5 mL, 29.5 mmol) was slowly added into a solution of 2-bromo-3-thiophene formic acid (5.0 g, 24.1 mmol) in dichloromethane (50 mL), and the reaction mixture was stirred overnight at room temperature. Concentrated to remove the solvent, and the residue was dissolved in methanol (50 mL) and heated to reflux for 4 hours. The mixture was concentrated in vacuo to give a yellow oily compound 2 (5.2 g, yield: 93.6%).

MS (ESI): Calcd. for $C_6H_5BrO_2S$ 220; Found 221 [M+H]+.

Step Two: 2-(3-((tert-butoxycarbonyl) amino)-1-propynyl-3-thiophene methyl formate (Compound 3)

(1,1'-bis (diphenylphosphino) ferrocene) palladium dichloride (0.50 g, 0.67 mmol) and cuprous iodide (0.13 g, 0.67 mmol) were added into a solution of 2-bromo-3-thiophene methyl formate (3.0 g, 13.5 mmol), N-tert-butoxycarbonylaminopropyne (2.5 g, 16.3 mmol) and diisopropylethylamine (5 mL) in acetonitrile (30 mL), the resulting mixture was heated to reflux and stirred overnight under the protection of nitrogen. The reaction solution was cooled to room temperature, filtered with celite, the filtrate was concentrated to remove the solvent, and the residue was purified with a silica gel column to obtain a yellow oily compound 3 (3.4 g, yield: 84.9%).

MS (ESI): Calcd. for $C_{14}H_{17}NO_4S$ 295; Found 296 [M+H]+.

Step Three: 2-(3-((tert-butoxycarbonyl) amino)-propyl)-3-thiophene methyl formate (Compound 4)

10% palladium carbon (0.34 g) was added into a solution of 2-(3-((tert-butoxycarbonyl)amino)-1-propynyl-3-methyl thiophenecarboxylate (3.4 g, 11.5 mmol) in tetrahydrofuran (30 mL), and the reaction mixture was stirred overnight under 4 atm hydrogen, filtered and concentrated to obtain a light yellow oily compound 4 (3.4 g, yield: 98.6%).

MS (ESI): Calcd. for $C_{14}H_{21}NO_4S$ 299; Found 200 [M-99]+.

Step Four: 2-(3-aminopropyl)-3-thiophene methyl formate (Compound 5)

Trifluoroacetic acid (9.1 g, 80 mmol) was slowly dropped into a solution of 2-(3-((tert-butoxycarbonyl)amino)-propyl)-3-thiophene methyl formate (3.4 g, 11.4 mmol) in dichloromethane (40 mL). The reaction was stirred at room temperature for 3 hours and then directly concentrated to obtain a yellow oily crude compound 5 (2.2 g, yield: 96.5%).

MS (ESI): Calcd. For $C_9H_{13}NO_2S$ 199; Found 200 [M+H]+.

Step Five: 5,6,7,8-tetrahydro-4H-thieno[3,2-c]azepin-4-one (Compound 6)

At room temperature, sodium methoxide (2.0 g) was added into a solution of (2-(3-aminopropyl)-3-methyl thiophenecarboxylate (2.2 g, 11.0 mmol) in methanol (40 mL). The reaction mixture was heated to reflux for 3 hours. The reaction solution was directly concentrated, and the residue was purified with a silica gel column to obtain a yellow oily compound 6 (1.4 g, yield: 75.8%).

MS (ESI): Calcd. for $C_8H_9NOS$ 167; Found 168 [M+H]+.

Step Six: 5,6,7,8-tetrahydro-4H-thieno[3,2-c] azepine (Compound 7)

At room temperature, lithium tetrahydroaluminum (956 mg, 25.2 mmol) was batch added into a solution of 5,6,7,8-tetrahydro-4H-thieno[3,2-c]azepin-4-one (1.4 g, 8.4 mmol) in tetrahydrofuran (50 mL). The reaction mixture was heated to reflux for 3 hours. The mixture was quenched with 15% NaOH (1 mL) and filtered with magnesium sulfate. The filtrate was concentrated and purified with a silica gel column to obtain a yellow oily compound 6 (800 mg, yield: 62.5%).

MS (ESI): Calcd. for $C_8H_{11}NS$ 153; Found 154 [M+H]+.

Step Seven: N-(2,6-dimethyl-4-(4,6,7,8-tetrahydro-5H-thieno[3,2-c]azepin-5-yl) phenyl)-3,3-dimethylbutanamide (Compound 03028)

The mixed reaction solution of tri(dibenzylideneacetone) dipalladium (31 mg, 0.034 mmol), tricyclohexylphosphorus (0.1 mL 10% solution), compound 7 (52 mg, 0.34 mmol), N-(4-bromo-2,6-dimethylphenyl)-3,3-dimethyl butanamide (200 mg, 0.68 mmol), potassium tert-butoxide (76 mg, 0.68 mmol) and dimethyl sulfoxide (5 mL) was reacted in a microwave reactor at 150° C. for 2 hours. The resulting mixture was diluted with water (25 mL) and extracted with ethyl acetate (30 mL×3). The combined organic phase was dried over anhydrous sodium sulfate, filtered and concentrated. The residue was purified by chromatography to obtain a white solid compound 03028 trifluoroacetate (12.7 mg, yield: 7.7%).

HNMR (400 MHz, CD3OD): δ7.18 (s, 2H), 7.12 (d, J=5.2 Hz, 1H), 7.00 (d, J=5.2 Hz, 1H), 4.80 (s, 2H), 4.00-3.93 (m, 2H), 3.15-3.11 (m, 2H), 2.31 (s, 2H), 2.25 (s, 6H), 2.16-2.08 (m, 2H), 1.12 (s, 9H). MS (ESI): Calcd. for $C_{22}H_{30}N_2OS$ 370; Found 371 [M+H]+. HPLC: 98.9% (214 nm)/99.3% (254 nm).

Example 4 Preparation of Compound 03029

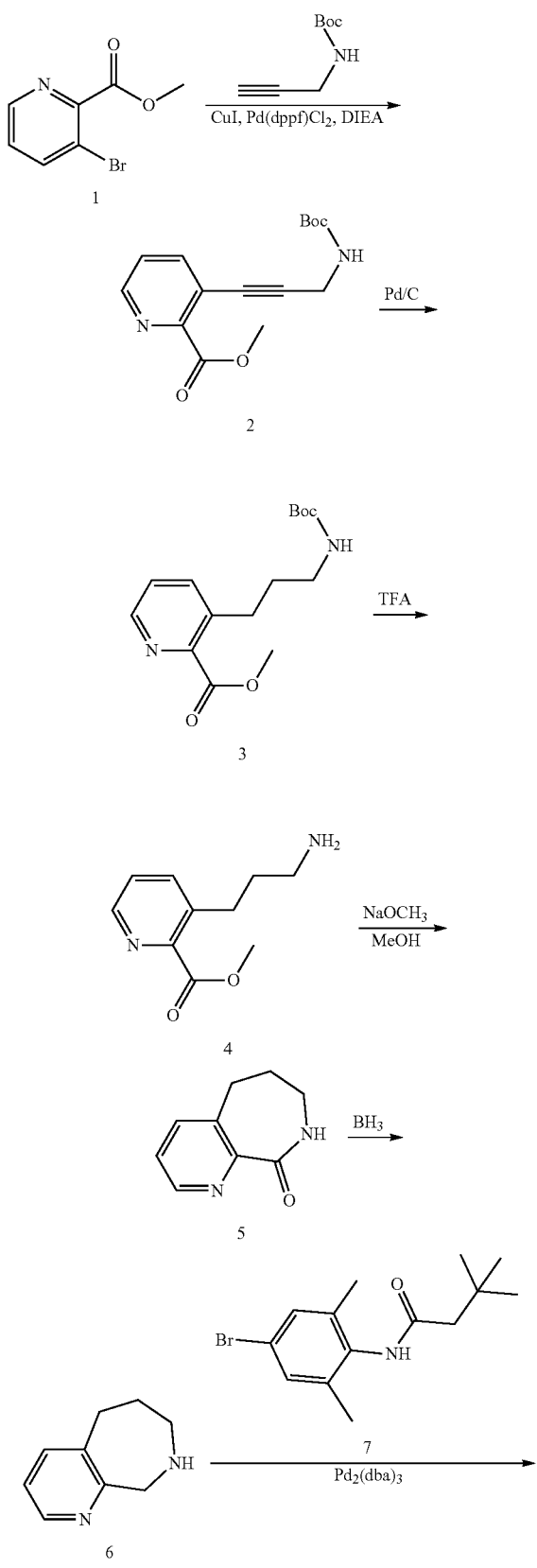

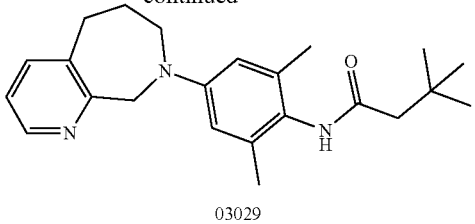

03029

Step One: 3-(3-((tert-butoxycarbonyl) amino)-1-propynyl)-2-pyridine methyl formate (Compound 2)

(1,1'-bis (diphenylphosphino) ferrocene) palladium dichloride (0.90 g, 1.0 mmol) and cuprous iodide (0.2 g, 1.5 mmol) were added into a solution of 3-bromo-2-pyridine methyl formate (2.5 g, 11.6 mmol), N-tert-butoxycarbonylaminopropyne (2.0 g, 12.9 mmol) and diisopropylethylamine (5 mL) in acetonitrile (30 mL), the resulting mixture was heated to reflux for 6 hours under the protection of nitrogen. The reaction solution was cooled to room temperature, filtered with celite, the filtrate was concentrated to remove the solvent, and the residue was purified with a silica gel column to obtain a yellow solid compound 2 (1.4 g, yield: 41.7%).

HNMR (400 MHz, $CDCl_3$): δ8.64 (d, J=3.6 Hz, 1H), 7.88 (d, J=8.0 Hz, 1H), 7.47-7.38 (m, 1H), 4.86 (s, 1H), 4.23 (d, J=2.8 Hz, 2H), 4.01 (s, 3H), 1.48 (s, 9H).

Step Two: 3-(3-((tert-butoxycarbonyl) amino)-propynyl)-2-pyridine methyl formate (Compound 3)

10% palladium carbon (0.14 g) was added into a solution of 3-(3-((tert-butoxycarbonyl)amino)-1-propynyl)-2-pyridine methyl formate (1.4 g, 4.8 mmol) in tetrahydrofuran (30 mL), and the mixture was stirred overnight under 4 atm hydrogen, filtered and concentrated to obtain a light yellow oily compound 3 (1.4 g, yield: 98.6%).

MS (ESI): Calcd. for $C_{15}H_{22}N_2O_4$ 294; Found 295 [M+H]+, 317 [M+Na]+.

Step Three: 3-(3-aminopropyl)-2-pyridine methyl formate (Compound 4)

Trifluoroacetic acid (4.5 g, 40 mmol) was slowly dropped into a solution of 3-(3-((tert-butoxycarbonyl)amino)-propyl)-2-pyridine methyl formate (1.4 g, 4.7 mmol) in dichloromethane (20 mL). The reaction was stirred at room temperature for 3 hours and then directly concentrated to obtain a yellow oily crude compound 4 (1.0 g), which was used in the next step without further purification.

MS (ESI): Calcd. for $C_{10}H_{14}N_2O_2$ 194; Found 195 [M+H]+.

Step Four: 5,6,7,8-tetrahydro-9H-pyrido[2,3-c]azepin-9-one (Compound 5)

At room temperature, sodium methoxide (1.0 g) was added into a solution of (3-(3-aminopropyl)-2-pyrido methyl formate (1.0 g) in methanol (20 mL). The reaction mixture was heated to reflux for 3 hours. The reaction solution was directly concentrated, and the residue was purified with a silica gel column to obtain a yellow oily compound 5 (500 mg, yield: 59.8%).

MS (ESI): Calcd. for $C_9H_{10}N_2O$ 162; Found 163 [M+H]+.

Step Five: 6,7,8,9-tetrahydro-5H-pyrido[2,3-c]azepine (Compound 6)

At room temperature, borane tetrahydrofuran solution (1.0 M, 20 mL) was slowly added into a solution of 5,6,7,8-tetrahydro-9H-pyrido[2,3-c]azepin-9-one (500 mg, 3.1 mmol) in tetrahydrofuran (5 mL). The reaction mixture was heated to reflux for 3 hours. The mixture was diluted with methanol (10 mL) and concentrated. The residue was purified with a silica gel column to obtain a yellow oily compound 6 (100 mg, yield: 21.9%).

MS (ESI): Calcd. for $C_9H_{12}N_2$ 148; Found 149 [M+H]+.

Step Six: N-(2,6-dimethyl-4-(5,6,7,9-tetrahydro-8H-pyrido[2,3-c]azepin-8-yl)phenyl)-3,3-dimethylbutanamide (Compound 03029)

The mixed reaction solution of tri(dibenzylideneacetone) dipalladium (31 mg, 0.034 mmol), tricyclohexylphosphorus (0.1 mL 10% solution), 6,7,8,9-tetrahydro-5H-pyrido[2,3-c]azepine (52 mg, 0.34 mmol), N-(4-bromo-2,6-dimethylphenyl)-3,3-dimethyl butanamide (200 mg, 0.68 mmol), potassium tert-butoxide (76 mg, 0.67 mmol) and dimethyl sulfoxide (5 mL) was reacted in a microwave reactor at 150° C. for 2 hours. The resulting mixture was diluted with water (25 mL) and extracted with ethyl acetate (30 mL×3). The combined organic phase was dried over anhydrous sodium sulfate, filtered and concentrated. The residue was purified by TLC plate to obtain a white solid compound 03029 (6.8 mg, yield: 5.3%).

HNMR (400 MHz, CD$_3$OD): δ8.27 (d, J=5.2 Hz, 1H), 7.61 (d, J=7.2 Hz, 1H), 7.45-7.20 (dd, J=5.2 Hz, J=7.2 Hz, 1H)), 6.63 (s, 2H), 4.78 (s, 2H), 3.90 (t, J=4.8 Hz, 2H), 3.07-3.01 (m, 2H), 2.26 (s, 2H), 2.12 (s, 6H), 1.94-1.87 (m, 2H), 1.11 (s, 9H). MS (ESI): Calcd. for $C_{23}H_{31}N_3O$ 365; Found 366 [M+H]+. HPLC: 97.2% (214 nm)/99.4% (254 nm).

Example 5 Preparation of Compound 03033

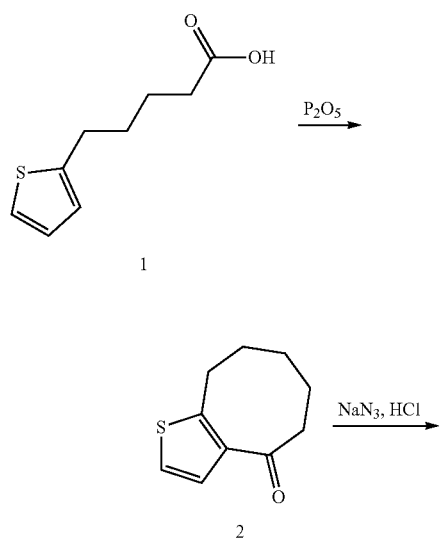

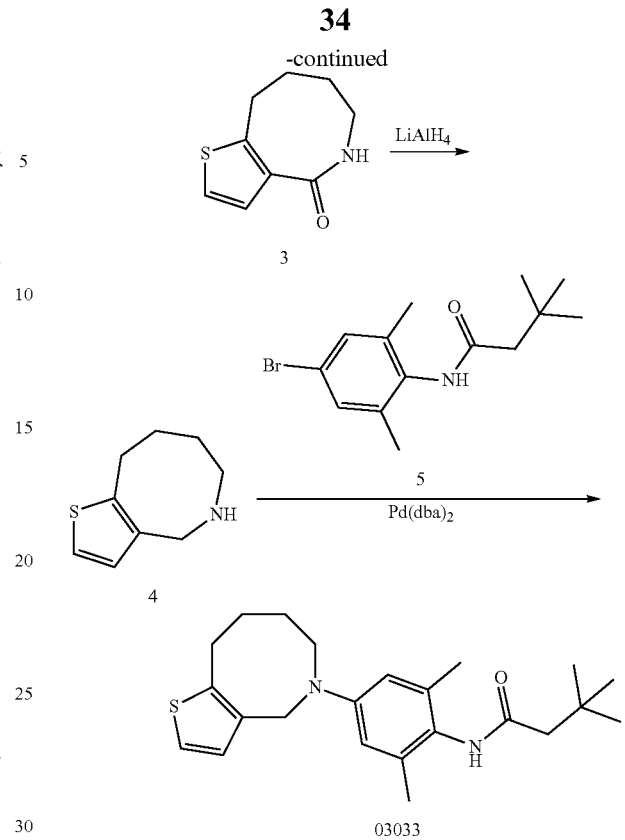

Step One: 5,6,7,8-tetrahydro-4H-cycloheptatrieno[b]thiophen-4-one (Compound 2)

Phosphorus pentoxide(1.5 g, 10.9 mmol) and molecular sieves (2 g) were added into a solution of 5-(thiophen-2-yl)pentanoic acid (1.00 g, 5.40 mmol) in toluene (20 mL). The reaction mixture was heated to 130° C. and reacted for 2 hours under the protection of nitrogen. Cooled to room temperature, filtered, washed with saturated sodium bicarbonate (30 mL), dried, concentrated in vacuo to remove the solvent, and purified by column chromatography to obtain compound 2 (0.42 g, yield: 46.6%) as a yellow oil.

MS (ESI): Calcd. for $C_9H_{10}OS$ 166; Found 167 [M+H]$^+$.

Step Two: 6,7,8,9-tetrahydrothieno[3,2-c]azocin-4(5H)-one (Compound 3)

Sodium azide (501 mg) was added into a solution of compound 2 (0.64 g, 3.86 mmol) in concentrated hydrochloric acid (20 mL). The mixture was stirred at room temperature for 16 hours, poured into ice water, adjusted to pH=7 with potassium carbonate, extracted with ethyl acetate, dried over anhydrous sodium sulfate, the solvent was concentrated in vacuo, and purified by column chromatography to obtain an off-white solid compound 3 (400.0 mg, yield: 57.25%).

MS (ESI): Calcd. for $C_9H_{11}NOS$ 181; Found 182 [M+H]$^+$.

Step Three: 4,5,6,7,8,9-hexahydrothieno[3,2-c]azocin (Compound 4)

Lithium aluminum hydride (420 mg, 11.05 mmol) was added into a solution of compound 3 (400 mg, 2.21 mmol)

in tetrahydrofuran (40 mL). The mixture was heated to 80° C. and stirred for 2 hours. Cooled to room temperature, water (2 mL) and 10% sodium hydroxide (1 mL) were added to quench the reaction, filtered, concentrated the filtrate, and purified the residue by column chromatography to obtain a yellow oily compound 4 (150 mg, yield: 40.90%).

MS (ESI): Calcd. for $C_9H_{13}NS$ 167; Found 168 $[M+H]^+$.

Step Four: N-(2,6-dimethyl-4-(6,7,8,9-tetrahydrothieno[3,2-c]azocin-5(4H)-yl)phenyl)-3,3-dimethylbutanamide (Compound 03033)

Compound 5 (178 mg, 0.60 mmol), $Pd_2(dba)_3$ (10 mg, 0.034 mmol), tri-tert-butylphosphon-hexane solution (1 mol/L, 0.2 mL) and potassium tert-butoxide (100 mg, 0.9 mmol) were added into a solution of compound 4 (50 mg, 0.30 mmol) in DMSO (2 mL). The mixture was microwave reacted at 150° C. for 1 hour. The mixture was cooled to room temperature, quenched with water, extracted with ethyl acetate, dried over anhydrous sodium sulfate, concentrated in vacuo, and the residue was purified by column chromatography to obtain an off-white solid compound 03030 (14.78 mg, yield: 12.8%).

MS (ESI): Calcd. for $C_{23}H_{32}N_2OS$ 384; Found 385 $[M+H]^+$.

HNMR (400 MHz, $CD_3OD$): δ7.10 (d, J=5.2 Hz, 1H), 6.90 (d, J=5.2 Hz, 1H), 6.44 (s, 2H), 4.55 (s, 2H), 3.56-3.48 (m, 2H), 2.82-2.74 (m, 2H), 2.29 (s, 2H), 2.15 (s, 6H), 1.80-1.70 (m, 4H), 1.14 (s, 9H).

Example 6 Preparation of Compound 03034

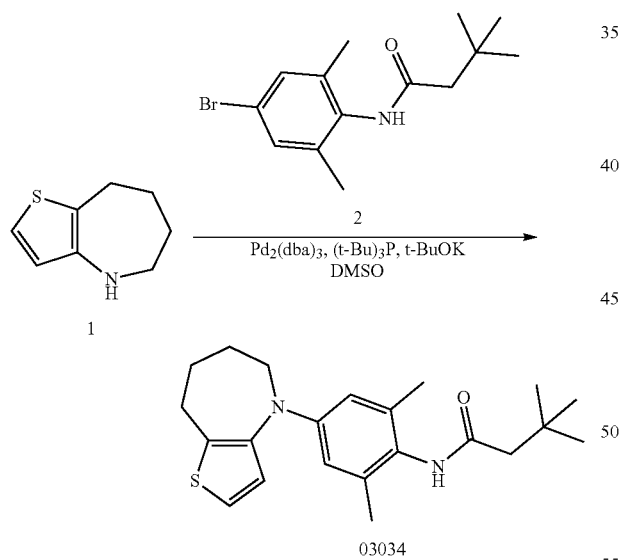

Step One: (N-(2,6-dimethyl-6-(1-tert-butylacetyl) aniline))-(5,6,7,8-tetrahydro-4H)-thieno[3,2]azaanthracene (CB03034)

Compound 2 (484 mg, 1.63 mmol), $Pd_2(dba)_3$ (149 mg, 0.16 mmol), tri-tert-butylphosphon-hexane solution (66 mg, 0.33 mmol) and potassium tert-butoxide (365 mg, 3.26 mmol) were added into a solution of compound 1 (250 mg, 1.63 mmol) in DMSO (5 mL). The mixture was microwave reacted at 150° C. for 0.5 hour. Then the mixture was cooled to room temperature, quenched with water, extracted with ethyl acetate, dried over anhydrous sodium sulfate, concentrated in vacuo, and purified by column chromatography to obtain a white solid compound 03034 (49.12 mg, yield: 8.12%).

MS (ESI): Calcd. for $C_{22}H_{30}N_2OS$ 370; Found 371 $[M+H]^+$.

HNMR (400 MHz, $CDCl_3$): δ6.98 (d, J=4.0 Hz, 1H), 6.84 (d, J=8.0 Hz, 1H), 6.47-6.49 (m, 3H), 3.68 (t, J=4.0 Hz, 2H), 3.77 (t, J=6.0 Hz, 2H), 2.29 (s, 2H), 2.16 (s, 6H), 1.89-1.91 (m, 2H), 1.74-1.68 (m, 2H), 1.16 (s, 9H).

Example 7 Preparation of Compound 03039

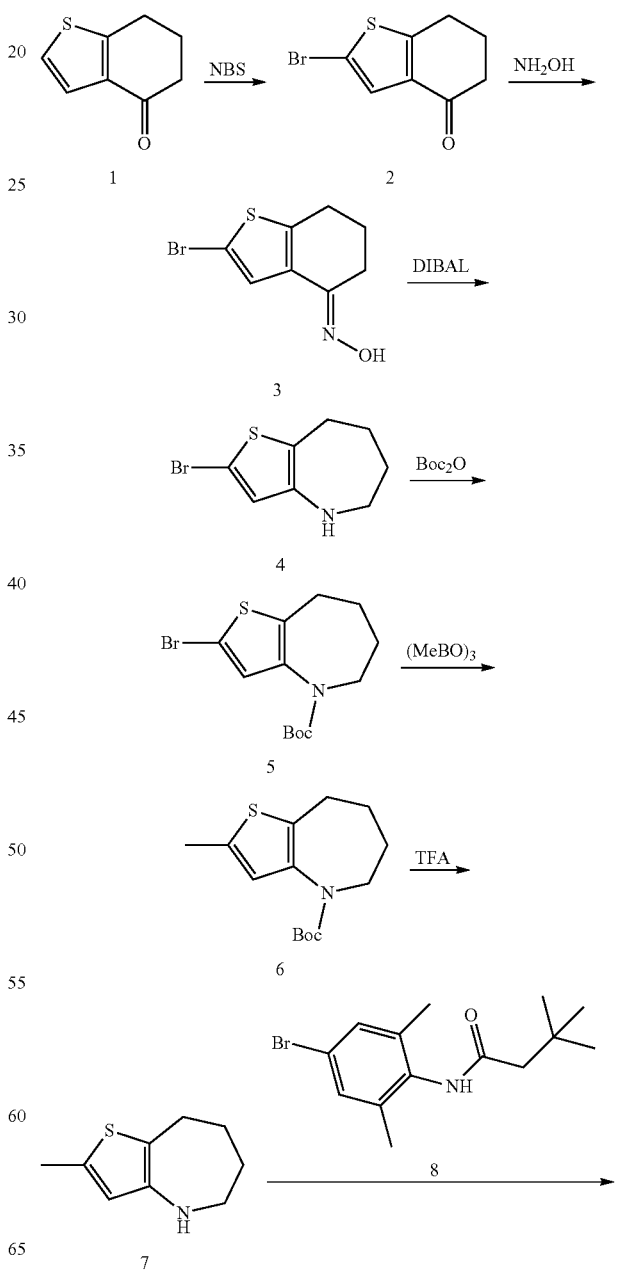

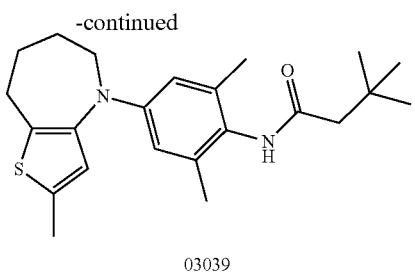

03039

Step One: 2-bromo-6,7-dihydrobenzo[b]thiophene-4(5H)-one (Compound 2)

Under ice-cooling, NBS (266 mg, 1.5 mmol) was added into a solution of 6,7-dihydrobenzo[b]thiophene-4(5H)-one (152 mg, 1 mmol) in DMF (5 mL) in batches, the reaction mixture was reacted at room temperature for 12 hours. The mixture was quenched by adding water (10 mL) at 0° C., extracted with ethyl acetate, dried over anhydrous sodium sulfate, filtered, and concentrated to obtain a colorless oily compound 2 (200 mg, yield: 86.0%).

MS (ESI): Calcd. for $C_8H_7BrOS$ 230; Found 231 $[M+H]^+$.

Step Two: 2-bromo-6,7-dihydrobenzo[b]thiophene-4(5H)-ketoxime (Compound 3)

Sodium acetate (5.10 g, 63 mmol) and hydroxylamine hydrochloride (4.30 g, 63 mmol) were added into a solution of 2-bromo-6,7-dihydrobenzo[b]thiophene-4(5H)-one (4.72 g, 21 mmol) in mixed ethanol (100 mL) and water (20 mL) in batch, and the reaction mixture was reacted at 80° C. for 3 hours, and cooled to room temperature, filtered and concentrated to obtain brown solid compound 3 (3.80 g, yield: 75.0%).

MS (ESI): Calcd. for $C_8H_8BrNOS$ 245; Found 246 $[M+H]^+$.

Step Three: 2-bromo-5,6,7,8-tetrahydro-4H-thieno[3,2-b]azepine (Compound 4)

In an ice water bath, DIBAL-H (62 mg, 0.46 mmol) was added into 2-bromo-6,7-dihydrobenzo[b]thiophen-4(5H)-ketoxime (300 mg, 1.22 mmol) in dichloromethane (10 mL). The reaction mixture was stirred at room temperature for 4 hours, quenched with water, extracted with ethyl acetate, dried over anhydrous sodium sulfate, filtered, concentrated, and separated and purified by silica gel column to obtain a colorless oily compound 4 (100 mg, yield: 35.0%).

MS (ESI): Calcd. for $C_8H_{10}BrNS$ 231; Found 232 $[M+H]^+$.

Step Four: 2-bromo-5,6,7,8-tetrahydro-4H-thieno[3,2-b]azepine-4-carboxylic acid tert-butyl ester (Compound 5)

DMAP (223 mg, 1.7 mmol) and BOC-anhydride (3.77 g, 17 mmol) were added into a solution of compound 4 (2 g, 8.7 mmol) in THF (15 mL). The reaction mixture was heated to reflux for 6 hours. The solvent was spin-dried, diluted with water (10 mL) and ethyl acetate, the organic phase was dried over anhydrous sodium sulfate, filtered, and concentrated to obtain a white solid compound 5 (14 g, yield: 48.9%).

MS (ESI): Calcd. for $C_{13}H_{18}BrNO_2S$ 331 Found 276 $[M-56+H]^+$.

Step Five: 2-methyl-5,6,7,8-tetrahydro-4H-thieno[3,2-b]azepine-4-carboxylic acid tert-butyl ester (Compound 6)

Trimethoxyboron (69 mg, 0.542 mmol), potassium carbonate (125 mg, 0.90 mmol) and tetrakistriphenylphosphine palladium (52 mg, 0.045 mmol) were added into a solution of compound 5 (150 mg, 0.452 mmol) in DMF (5 mL). The reaction mixture was heated to 120° C. and stirred for 3 hours. The reaction mixture was cooled to room temperature, filtered, and concentrated. The residue was separated and purified by a silica gel column to obtain a white solid compound 6 (112 mg, yield: 93.2%).

MS (ESI): Calcd. for $C_{14}H_{21}NO_2S$ 267; Found 212 $[M-56+H]^+$.

Step Six: 2-methyl-5,6,7,8-tetrahydro-4H-thieno[3,2-b]azepine (Compound 7)

Trifluoroacetic acid (2 mL) was added into a solution of compound 6 (112 mg, 0.419 mmol) in DCM (5 mL). The mixture was stirred at room temperature for 3 hours. The solvent was removed, the pH was adjusted to be neutral, extracted with ethyl acetate, concentrated, and the residue was separated and purified by silica gel column to obtain a white solid compound 7 (40 mg, yield: 57.1%).

Step Seven: N-(2,6-dimethyl-4-(2-methyl-5,6,7,8-tetrahydro-4H-thieno[3,2-b]azepin-4-yl)phenyl)-3,3-dimethylbutyramide (Compound 03039)

N-(4-bromo-2,6-dimethylphenyl)-3,3-dimethylbutanamide (250 mg, 0.84 mmol), potassium tert-butoxide (130 mg, 0.84 mmol), tris(dibenzylideneacetone) dipalladium (39 mg, 0.042 mmol), and tri-tert-butylphosphorus (0.3 mL, 0.084 mmol) were added into a solution of compound 7 (70 mg, 0.42 mmol) in DMSO (2 mL). The reaction mixture was heated to 150° C. and reacted in microwave for 2 hours. The reaction mixture was cooled to room temperature, filtered, and concentrated. The residue was separated and purified by a silica gel column to obtain a white solid compound 03039 (10 mg, yield: 6.2%).

MS (ESI): Calcd. for $C_{23}H_{32}N_2OS$ 384; Found 385 $[M+H]^+$.

1H NMR (400 MHz, $CD_3CN$) δ7.44 (s, 1H), 6.53 (s, 1H), 6.47 (s, 2H), 3.70-3.64 (m, 2H), 2.69-2.66 (m, 2H), 2.39 (s, 3H), 2.23 (s, 2H), 2.10 (s, 6H), 1.87-1.81 (m, 2H), 1.68-1.62 (m, 2H), 1.12 (s, 9H).

Example 8 Preparation of Compound 03041

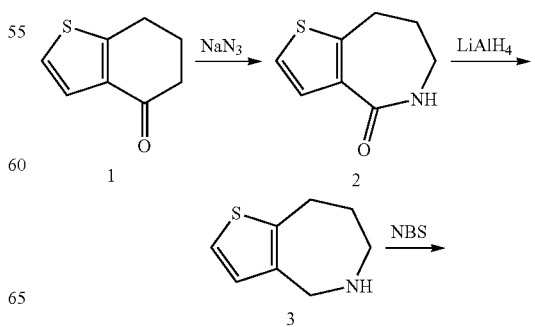

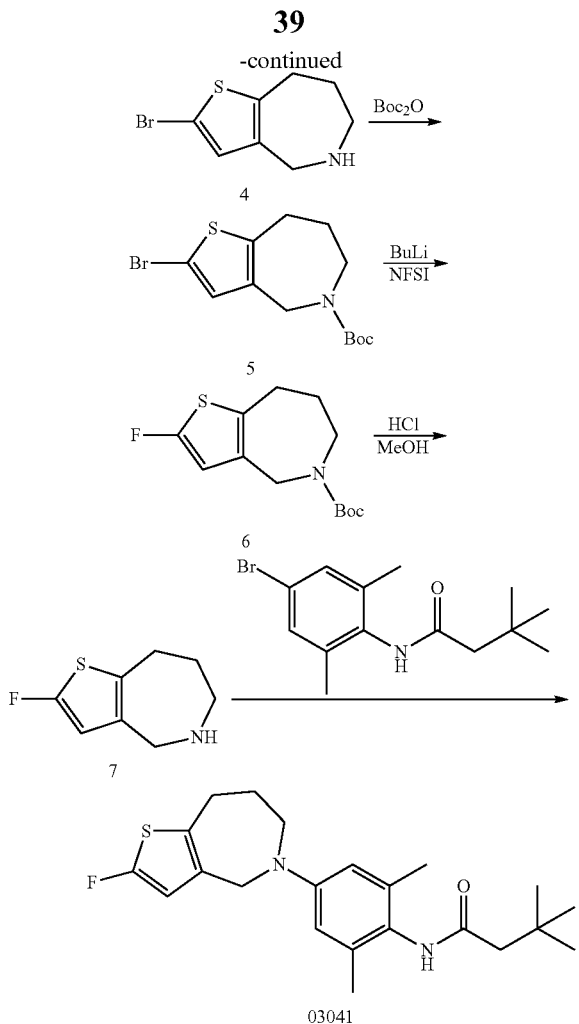

Step One: 5,6,7,8-tetrahydro-4H-thieno[3,2-c]azepin-4-one (Compound 2)

Under ice-cooling, sodium azide (15 g, 250 mmol) was added into a solution of 6,7-dihydrobenzo[b]thiophene-4 (5H)-one (15 g, 98 mmol) in hydrochloric acid (100 mL) in batches, the reaction mixture was reacted overnight at room temperature. Ice cubes were added, and the pH was adjusted to be greater than 7 with saturated potassium carbonate aqueous solution, the mixture was extracted with dichloromethane, dried with anhydrous sodium sulfate, filtered, concentrated to obtain a crude white solid compound 2 (13 g) by column chromatography.

MS (ESI): Calcd. for $C_8H_9NOS$ 167; Found 168 [M+H]$^+$.

Step Two: 5,6,7,8-tetrahydro-4H-thieno[3,2-c] azepine (Compound 3)

Under ice cooling, compound 2 (13 g, 78 mmol) was slowly added into a suspension of lithium aluminum hydride (8.9 g, 230 mmol) in tetrahydrofuran (200 mL), and the mixture was heated to 70° C. and stirred for 1 hour, Then water (9 ml), sodium hydroxide aqueous solution (15%, 9 mL) and water (27 ml) were slowly added, then enough anhydrous magnesium sulfate was added, filtered, concentrated, and the residue was subjected to column chromatography to obtain compound 3 (9.0 g, yield: 75%).

MS (ESI): Calcd. for $C_8H_{11}NS$ 153; Found 154 [M+H]$^+$.

Step Three: 2-bromo-5,6,7,8-tetrahydro-4H-thieno [3,2-c]azepine (Compound 4)

Hydrochloric acid (2.3 g, 62 mmol) was added into a solution of 5,6,7,8-tetrahydro-4H-thieno[3,2-c]azepine (8.0 g, 50 mmol) in tetrahydrofuran (100 mL), the mixture was stirred at room temperature for 30 minutes. After concentration to remove excess hydrochloric acid, acetic acid (10 mL) and N-bromosuccinimide (12.0 g, 68 mmol) were added sequentially. The reaction mixture was stirred at room temperature for 3 hours, a saturated sodium bicarbonate aqueous solution was added to adjust the pH to be greater than 7, and the next step reaction was carried out without purification.

MS (ESI): Calcd. for $C_8H_{10}BrNS$ 231; Found 232 [M+H]$^+$.

Step Four: tert-butyl 2-bromo-4,6,7,8-tetrahydro-5H-thieno[3,2-c]azepine-5-carboxylate (Compound 5)

BOC-anhydride (19 g, 87 mmol) was added into a solution of compound 4 (8 g, 35 mmol) in tetrahydrofuran (200 mL), the mixture was reacted at room temperature for 2 hours, concentrated, and subjected to silica gel column chromatography to obtain a crude white solid compound 5 (15 g).

MS (ESI): Calcd. for $C_{13}H_{18}BrNO_2S$ 331; Found 276 [M-56+1]$^+$.

Step Five: tert-butyl 2-fluoro-4,6,7,8-tetrahydro-5H-thieno[3,2-c]azepine-5-carboxylate (Compound 6)

Under dry ice cooling, n-butyllithium (2.6 mL, 6.24 mmol) was slowly added into a solution of compound 5 (1.0 g, 3.02 mmol) in tetrahydrofuran (20 mL), and the mixture was stirred at −78° C. for 1 hour. Then N-fluorobisbenzenesulfonamide (1.91 g, 6.05 mmol) was slowly added. The reaction mixture was slowly returned to room temperature and stirred overnight. After ice water was added, the mixture was extracted, dried, and concentrated. The residue was subjected to column chromatography to obtain compound 6 crude product (800 mg).

MS (ESI): Calcd. for $C_{13}H_{18}FNO_2S$ 271; Found 216 [M-56+1]$^+$.

Step Six: 2-fluoro-5,6,7,8-tetrahydro-4H-thieno[3,2-c]azepine (Compound 7)

Hydrochloric acid (1.87 mL, 7.49 mmol) was added into a solution of compound 6 (800 mg, 2.95 mmol) in 1,4-dioxane (20 mL), the mixture was stirred at room temperature for 1 hour, concentrated to remove excess hydrochloric acid, and saturated sodium bicarbonate aqueous solution was added to adjust the pH to be greater than 7, the mixture was extracted, dried, and concentrated, the residue was subjected to column chromatography to obtain crude compound 7 (1.0 g).

MS (ESI): Calcd. for $C_8H_{10}FNS$ 171; Found 172 [M+H]$^+$.

Step Seven: N-(4-(2-fluoro-4,6,7,8-tetrahydro-5H-thieno[3,2-c]azepin-5-yl)-2,6-dimethylphenyl)-3,3-dimethylbutanamide (03041)

Intermediate N-(4-bromo-2,6-dimethylphenyl)-3,3-dimethyl butanamide (1.9 g, 6.4 mmol) and sodium tert-butoxide (2.25 g, 20 mmol) were added into a solution of compound 7 (1.0 g, 5.8 mmol) in tert-butanol (100 mL). After nitrogen exchange for three times, methanesulfonic acid (2-dicyclohexylphosphino-2',6'-diisopropoxy-1,1'-biphenyl)(2-amino-1,1'-biphenyl-2-yl)palladium(II) (830 mg, 990 mmol) was added. The reaction mixture was heated to 95° C. under nitrogen and stirred overnight, filtered, concentrated to remove the solvent, the residue was subjected to column chromatography to obtain crude compound 03041, which was further purified by preparative chromatography to obtain compound 03041 (57 mg, yield: 2.5%).

MS (ESI): Calcd. for $C_{22}H_{29}FN_2OS$ 388; Found 389 $[M+H]^+$.

1H NMR (400 MHz, CDCl$_3$): δ6.54 (s, 2H), 6.35 (s, 1H), 4.36 (s, 2H), 3.79-3.74 (m, 2H), 2.84-2.78 (m, 2H), 2.29 (s, 2H), 2.19 (s, 6H), 2.01-1.96 (m, 2H), 1.15 (s, 9H).

Example 9 Preparation of Compound 03042

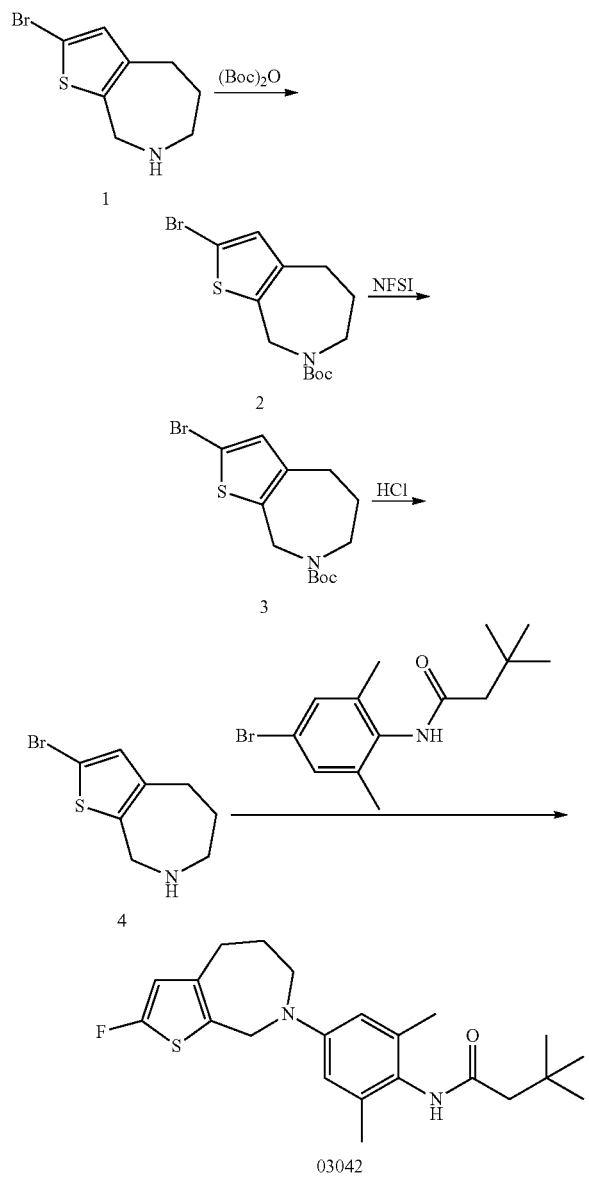

Step One: tert-butyl-2-bromo-4,5,6,8-tetrahydro-7H-thieno[2,3-c]azepine-7-carboxylate (Compound 2)

At room temperature, di-tert-butyl dicarbonate (569 mg, 2.61 mmol) was added into a solution of 2-bromo-5,6,7,8-tetrahydro-4H-thieno[2,3-c]azepine (300 mg, 1.30 mmol) in tetrahydrofuran (10 mL). The reaction mixture was heated to reflux for 16 hours. The reaction mixture was concentrated to remove the solvent, and the residue was purified by column chromatography to obtain compound 2 (230 mg, yield: 53.5%).

MS (ESI): Calcd. for $C_{13}H_{18}BrNO_2S$ 331; Found 276 $[M-56]^+$.

Step Two: tert-butyl-2-fluoro-4,5,6,8-tetrahydro-7H-thieno[2,3-c]azepine-7-carboxylate (Compound 3)

Compound 2 (1.2 g, 3.63 mmol) was dissolved in anhydrous tetrahydrofuran (20 mL), the temperature was lowered to −78° C. under a nitrogen atmosphere, and n-butyllithium (2.4 M, 3.0 mL) was added dropwise. The reaction was kept at −78° C. for half an hour, and then a solution of N-fluorobisbenzenesulfonamide (2.29 g, 7.26 mmol) in tetrahydrofuran was added dropwise into the reaction system. After the addition, the mixture was slowly raised to room temperature and reacted at room temperature for 16 hours. The reaction was quenched with saturated ammonium chloride, extracted with ethyl acetate, dried over anhydrous sodium sulfate, filtered, concentrated to remove the solvent, and the residue was purified by column chromatography to obtain compound 3 (400 mg, yield: 40.7%).

MS (ESI): Calcd. for $C_{13}H_{18}FNO_2S$ 271; Found 216 $[M-56+H]^+$.

Step Three: 2-fluoro-5,6,7,8-tetrahydro-4H-thieno[2,3-c]azepine (Compound 4)

Hydrochloric acid methanol solution (4M, 40 mL) was added to compound 3. The mixture was stirred at room temperature for sixteen hours. After concentration to remove the solvent, sodium bicarbonate was added to adjust the pH to be equal to 8, and the residue was purified by column chromatography to obtain compound 4 (410 mg, yield: 64.9%).

MS (ESI): Calcd. for $C_8H_{10}FNS$ 171; Found 172 $[M+H]^+$.

Step Four: N-(4-(2-fluoro-4,5,6,8-tetrahydro-7H-thieno[2,3-c]azepin-7-yl)-2,6-dimethylphenyl)-3,3-dimethylbutanamide (Compound 03042)

N-(4-bromo-2,6-dimethylphenyl)-3,3-dimethyl butanamide (712 mg, 2.40 mmol), sodium tert-butoxide (921 mg, 9.59 mmol), methanesulfonic acid (2-dicyclohexylphosphino-2',6'-diisopropoxy-1,1'-linked biphenyl)(2-amino-1,1'-biphenyl-2-yl)palladium(II) (201 mg, 0.24 mmol) were added into a solution of compound 4 (410 mg, 2.40 mmol) in tert-butanol (20 mL) under nitrogen atmosphere. The mixture was reacted at 90° C. for sixteen hours. After the mixture was cooled to room temperature, filtered, the filtrate was concentrated in vacuo to remove the solvent, and the residue was purified by column chromatography to obtain the crude product, which was then separated by preparative chromatography to obtain compound 03042 (32.7 mg, yield: 3.5%).

MS (ESI): Calcd. for $C_{22}H_{29}FN_2OS$ 388; Found 389 $[M+H]^+$.

HNMR (400 MHz, CD$_3$OD): δ6.75 (s, 2H), 6.31 (s, 1H), 4.59 (s, 2H), 3.89-3.86 (m, 2H), 2.82-2.79 (m, 2H), 2.29 (s, 2H), 2.19 (s, 6H), 1.91-1.86 (m, 2H), 1.13 (s, 9H).

Example 10 Preparation of Compound 03043

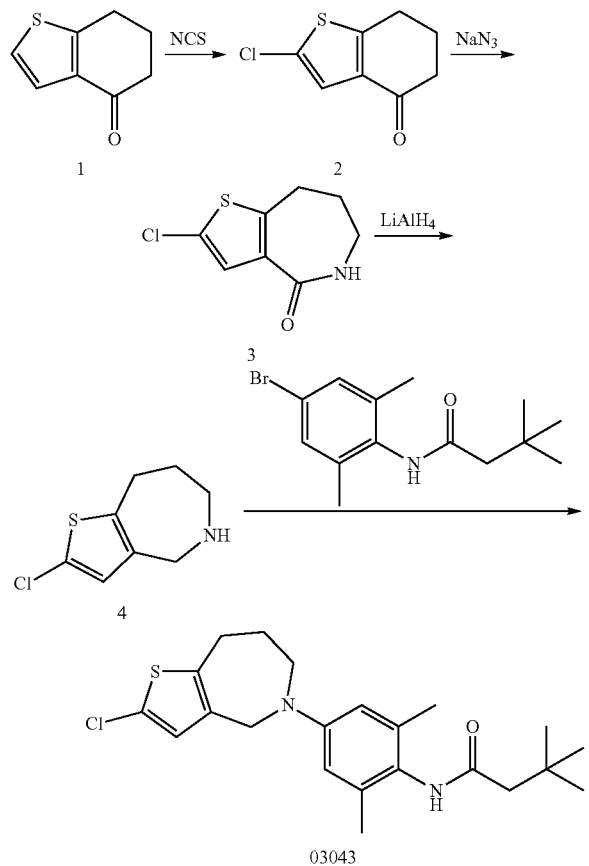

Step One: 2-chloro-6,7-dihydrobenzo[b]thiophene-4 (5H)-one (Compound 2)

N-chlorosuccinimide (32 g, 0.24 mol) was added into a solution of 6,7-dihydrobenzo[b]thiophene-4(5H)-one (25 g, 0.16 mol) in acetic acid (50 mL), the reaction mixture was heated to 50° C. and reacted overnight. The mixture was cooled to room temperature, concentrated, water and ethyl acetate were added for extraction, and the extract was dried over anhydrous sodium sulfate, filtered, and concentrated. The residue was subjected to column chromatography to obtain compound 2 (19 g, yield: 62%).

MS (ESI): Calcd. for C$_8$H$_7$ClOS 186; Found 187 [M+H]$^+$.

Step Two: 2-chloro-5,6,7,8-tetrahydro-4H-thieno[3,2-c]azepin-4-one (Compound 3)

Under ice-cooling, sodium azide (10 g, 0.15 mol) was slowly added to a solution of compound 2 (14 g, 0.07 mol) in hydrochloric acid (100 mL), and the reaction mixture was allowed to react overnight at room temperature. An appropriate amount of ice and a saturated potassium carbonate aqueous solution were added to adjust the pH to be greater than 7, the mixture was extracted, dried, filtered, and concentrated. The residue was subjected to column chromatography to obtain compound 3 (6 g, yield: 40%).

MS (ESI): Calcd. for C$_8$H$_8$ClNOS 201; Found 202 [M+H]$^+$.

Step Three: 2-chloro-5,6,7,8-tetrahydro-4H-thieno [3,2-c]azepine (Compound 4)

Under ice cooling, compound 3 (6 g, 29.8 mmol) was slowly added into a suspension of lithium aluminum hydride (5.6 g, 147 mmol) in tetrahydrofuran (50 mL), and the mixture was stirred at 70° C. for 1 hour, then water (5.6 mL), sodium hydroxide aqueous solution (15%, 5.6 mL) and water (16.8 mL) were slowly added in sequence, then enough anhydrous magnesium sulfate was added, the mixture was filtered, concentrated, and the residue was subjected to column chromatography to obtain Compound 4 (3 g, yield: 53.7%).

MS (ESI): Calcd. for C$_8$H$_{10}$ClNS 187; Found 188 [M+H]$^+$.

Step Four: N-(4-(2-chloro-4,6,7,8-tetrahydro-5H-thieno[3,2-c]azepin-5-yl)-2,6-dimethylphenyl)-3,3-dimethylbutanamide (Compound 03043)

The intermediate N-(4-bromo-2,6-dimethylphenyl)-3,3-dimethyl butanamide (3.6 g, 12 mmol) and sodium tert-butoxide (3.5 g, 36 mmol) were added into a solution of compound 4 (1.7 g, 9 mmol) in tert-butanol (50 mL). After replacing nitrogen for three times, methanesulfonic acid (2-dicyclohexylphosphino-2',6'-diisopropoxy-1,1'-biphenyl) (2-amino-1,1'-biphenyl-2-yl)palladium(II) (1.29 g, 1.53 mmol) was added. The reaction mixture was heated to 85° C. under nitrogen protection and reacted overnight, filtered and concentrated to remove the solvent. The residue was subjected to column chromatography to obtain crude compound 03043, which was further purified by preparative chromatography to obtain compound 03043 (600 mg, yield: 16.7%).

MS (ESI): Calcd. for C$_{22}$H$_{29}$ClN$_2$OS 404; Found 405 [M+H]$^+$.

1H NMR (400 MHz, CD$_3$OD): δ6.92 (s, 1H), 6.55 (s, 2H), 4.46 (s, 2H), 3.88-3.80 (m, 2H), 2.92-2.84 (m, 2H), 2.28 (s, 2H), 2.15 (s, 6H), 1.88 (s, 2H), 1.13 (s, 9H).

Example 11 Preparation of Compound 03044

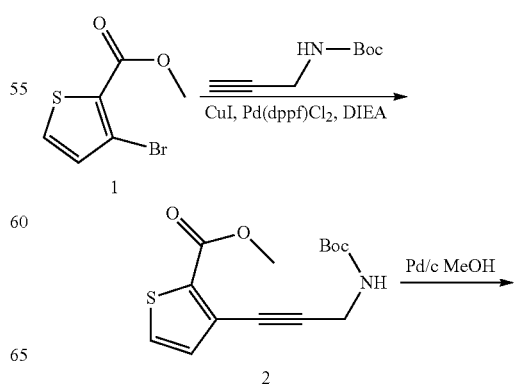

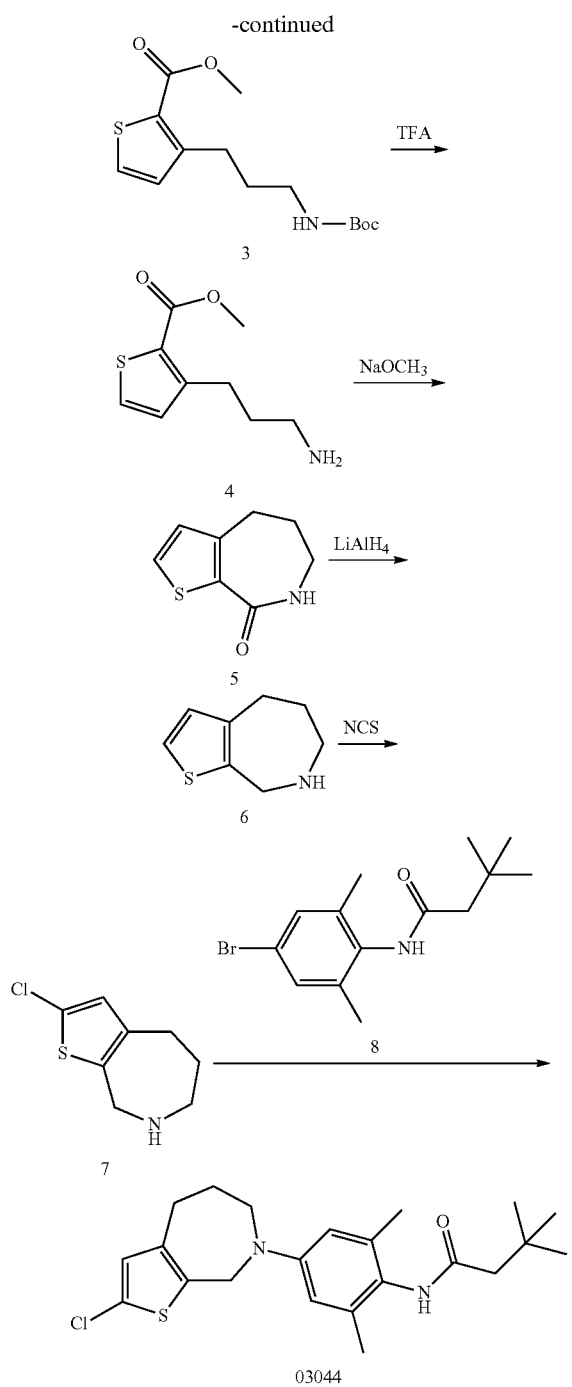

Step One: Methyl 3-(3-((tert-butoxycarbonyl)amino)prop-1-yn-1-yl)thiophene-2-carboxylate (Compound 2)

N-tert-butoxycarbonylaminopropyne (8.4 g, 54 mmol), cuprous iodide (0.86 g, 4.5 mmol), Pd(dppf)Cl$_2$ (1.7 g, 2.3 mmol) and DIEA (8.8 g, 68 mmol) were respectively added into a solution of 3-bromothiophene-2-carboxylic acid methyl ester (10.0 g, 45 mmol) in acetonitrile (100 mL).

The reaction mixture was heated to 80° C. under the protection of nitrogen and reacted for 16 hours. Cooled to room temperature, concentrated in vacuo to remove the solvent, and purified by column chromatography to obtain compound 3 (6.0 g, yield: 45.2%) as a yellow oil.

MS (ESI): Calcd. for C$_{14}$H$_{17}$NO$_4$S 295; Found 318 [M+Na]$^+$.

Step Two: Methyl 3-(3-((tert-butoxycarbonyl)amino)propyl)thiophene-2-carboxylate (Compound 3)

Palladium carbon (600 mg) was added into a solution of compound 2 (6.0 g, 0.02 mol) in methanol (40 mL). The mixture was stirred at room temperature under 0.4 MPa hydrogen atmosphere for 16 hours, filtered with suction, the filtrate was concentrated, and purified by column chromatography to obtain yellow oily compound 3 (6.0 g, yield: 100%).

MS (ESI): Calcd. for C$_{14}$H$_{21}$NO$_4$S 299; Found 322 [M+Na]$^+$.

Step Three: Methyl 3-(3-aminopropyl)thiophene-2-carboxylate (Compound 4)

2M solution of trifluoroacetic acid in dichloromethane (50 mL) was add to compound 3 (6.0 g, 0.02 mol). The mixture was stirred at room temperature for 2 hours. The filtrate was concentrated to obtain yellow oily compound 4 (4.0 g, yield: 100%).

MS (ESI): Calcd. for C$_9$H$_{13}$NO$_2$S 199; Found 200 [M+H]$^+$.

Step Four: 4,5,6,7-tetrahydro-8H-thieno[2,3-c]azepin-8-one (Compound 5)

Sodium methoxide (3.2 g, 0.06 mol) was added to a solution of compound 4 (4.0 g, 0.02 mol) in methanol (50 mL). The mixture was heated to 70° C. and stirred for 5 hours. The mixture was cooled to room temperature, filtered, the filtrate was concentrated and purified by column chromatography to obtain compound 5 as a yellow oil (2.8 g, yield: 83.8%).

MS (ESI): Calcd. for C$_8$H$_9$NOS 167; Found 168 [M+H]$^+$.

Step Five: 5,6,7,8-tetrahydro-4H-thieno[2,3-c]azepine (Compound 6)

Lithium aluminum hydride (1.9 g, 0.05 mol) was add to a solution of compound 5 (2.8 g, 17 mmol) in tetrahydrofuran (50 mL) under ice bath. The mixture was continuously stirred for 0.5 hour, and then heated to 80° C. and reacted for 2 hours. The mixture was cooled to room temperature, quenched, the solvent was concentrated in vacuo, and purified by column chromatography to obtain an off-white solid compound 6 (2.18 g, yield: 83.8%).

MS (ESI): Calcd. for C$_8$H$_{11}$NS 153; Found 154 [M+H]$^+$.

Step Six: 2-chloro-5,6,7,8-tetrahydro-4H-thieno[2,3-c]azepine (Compound 7)

Concentrated hydrochloric acid (1 mL) was added to a solution of compound 6 (2.0 g, 0.013 mol) in tetrahydrofuran (10 mL). The mixture was stirred at room temperature for 10 minutes and concentrated to remove the solvent. The residue was dissolved in tetrahydrofuran (50 mL) and acetic acid (15 mL), and NCS (1.58 g, 0.012 mol) was added in batches. The mixture was reacted at room temperature for 2 hours. The solvent was concentrated in vacuo and purified by column chromatography to obtain an off-white solid compound 7 (2.1 g, yield: 86.4%).

MS (ESI): Calcd. for $C_8H_{10}ClNS$ 187; Found 188 $[M+H]^+$.

Step Seven: N-(4-(2-chloro-4,5,6,8-tetrahydro-7H-thieno[2,3-c]azepin-7-yl)-2,6-dimethylphenyl)-3,3-dimethylbutanamide (Compound 03044)

Ruphos-Pd-G3 (940 mg, 11 mmol), sodium tert-butoxide (4.3 g, 45 mmol) and compound 8 (4.67 g, 15 mmol) were added into a solution of compound 7 (2.1 g, 11 mmol) in tert-butanol (40 mL), the mixture was heated to 90° C. under nitrogen and stirred overnight. The mixture was cooled to room temperature, filtered, washed with ethyl acetate, and concentrated. The residue was purified by Flash to give pale yellow compound 03044 (540 mg, yield: 12.2%).

MS (ESI): Calcd. for $C_{22}H_{29}ClN_2OS$ 404; Found 405 $[M+H]^+$.

HNMR (400 MHz, $CD_3OD$): δ8.75 (s, 1H), 6.81 (s, 1H), 6.53 (s, 2H), 4.57 (s, 2H), 3.84-3.75 (m, 2H), 2.82-2.73 (m, 2H), 2.16 (s, 2H), 2.04 (s, 6H), 1.75-1.65 (m, 2H), 1.04 (s, 9H).

Example 12 Preparation of Compound 03045

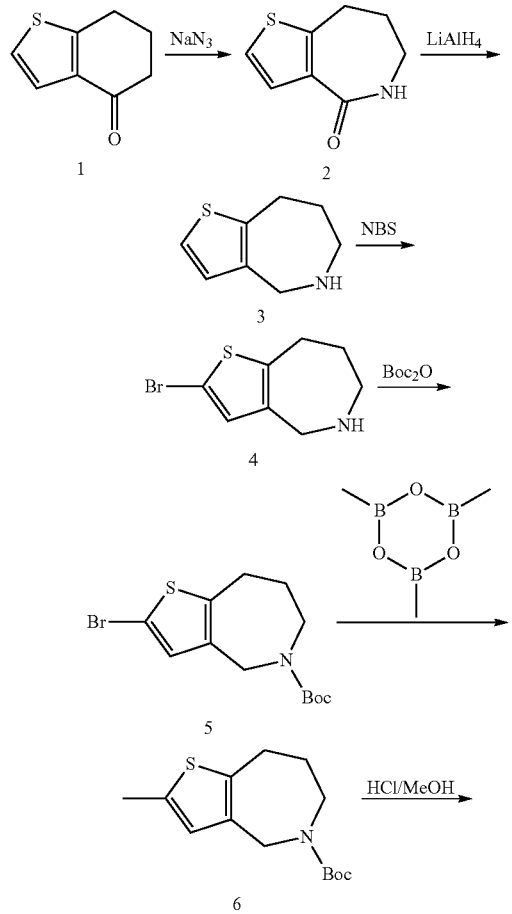

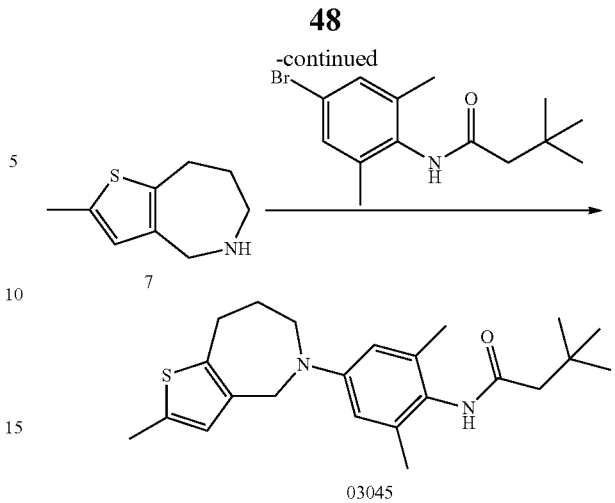

Step One: 5,6,7,8-tetrahydro-4H-thieno[3,2-c]azepin-4-one (Compound 2)

Under ice-cooling, sodium azide (15 g, 250 mmol) was added into a solution of 6,7-dihydrobenzo[b]thiophene-4(5H)-one (15 g, 98 mmol) in hydrochloric acid (100 mL) in batches, the reaction mixture was reacted overnight at room temperature. Ice cubes were added, and the pH was adjusted to be greater than 7 with saturated potassium carbonate aqueous solution, extracted with dichloromethane, dried with anhydrous sodium sulfate, filtered, concentrated, and subjected to silica gel column chromatography to obtain a crude white solid compound 2 (13 g).

MS (ESI): Calcd. for $C_8H_9NOS$ 167; Found 168 $[M+H]^+$.

Step Two: 5,6,7,8-tetrahydro-4H-thieno[3,2-c]azepine (Compound 3)

Under ice cooling, compound 2 (13 g, 78 mmol) was slowly added into a solution of lithium aluminum hydride (8.9 g, 230 mmol) in tetrahydrofuran (200 mL), and the mixture was heated to 70° C. and stirred for 1 hour, then water (9 mL), sodium hydroxide aqueous solution (15%, 9 mL) and water (27 mL) were slowly added in sequence, then enough anhydrous magnesium sulfate was added, filtered, concentrated, and the residue was subjected to column chromatography to obtain Compound 3 (9 g, yield: 75%).

MS (ESI): Calcd. for $C_8H_{11}NS$ 153; Found 154 $[M+H]^+$.

Step Three: 2-bromo-5,6,7,8-tetrahydro-4H-thieno[3,2-c]azepine (Compound 4)

Hydrochloric acid (2.3 g, 62 mmol) was added into a solution of 5,6,7,8-tetrahydro-4H-thieno[3,2-c]azepine (8 g, 50 mmol) in tetrahydrofuran (100 mL), the mixture was stirred at room temperature for 30 minutes. After concentrating to remove excess hydrochloric acid, acetic acid (10 mL) and N-bromosuccinimide (12 g, 68 mmol) were added sequentially. The reaction mixture was stirred at room temperature for 3 hours, a saturated sodium bicarbonate aqueous solution was added to adjust the pH to be greater than 7, and the next step reaction was carried out without purification.

MS (ESI): Calcd. for $C_8H_{10}BrNS$ 230.9; Found 231.9 $[M+H]^+$.

Step Four: tert-butyl 2-bromo-4,6,7,8-tetrahydro-5H-thieno[3,2-c]azepine-5-carboxylate (Compound 5)

BOC-anhydride (19 g, 87 mmol) was added into a solution of compound 4 (8 g, 35 mmol) in tetrahydrofuran (200 mL), the mixture was reacted at room temperature for 2 hours, concentrated, and subjected to column chromatography to obtain a crude white solid compound 5 (15 g).

MS (ESI): Calcd. for $C_{13}H_{18}BrNO_2S$ 331; Found 276 $[M-56+1]^+$.

Step Five: tert-butyl 2-methyl-4,6,7,8-tetrahydro-5H-thieno[3,2-c]azepine-5-carboxylate (Compound 6)

Potassium carbonate (2.5 g, 18 mmol) was added to a solution of compound 5 (2 g, 6 mmol) in 1,4-dioxane (100 mL), replaced nitrogen for three times, and then 2,4,6-trimethyl-1,3,5,2,4,6-trioxatriborinane (3 g, 24 mmol) and tetrakis(triphenylphosphine) palladium (2 g, 1.8 mmol) were added. The reaction mixture was reacted overnight at 120° C., filtered, concentrated to remove the solvent, and the residue was subjected to column chromatography to obtain crude compound 6 (400 mg).

MS (ESI): Calcd. for $C_{14}H_{21}NO_2S$ 267; Found 212 $[M-56+1]^+$.

Step Six: 2-methyl-5,6,7,8-tetrahydro-4H-thieno[3,2-c]azepine (Compound 7)

Hydrochloric acid (1.87 mL, 7.49 mmol) was added into a solution of compound 6 (400 mg, 1.49 mmol) in methanol (20 mL), the mixture was stirred at room temperature for 1 hour, concentrated to remove excess hydrochloric acid, and saturated sodium bicarbonate aqueous solution was added to adjust the pH to be greater than 7, the mixture was extracted, dried, and concentrated, and the residue was subjected to column chromatography to obtain crude compound 7 (270 mg).

MS (ESI): Calcd. for $C_9H_{13}NS$ 167; Found 168 $[M+H]^+$.

Step Seven: N-(2,6-dimethyl-4-(2-methyl-4,6,7,8-tetrahydro-5H-thieno[3,2-c]azepin-5-yl)phenyl)-3,3-dimethylbutanamide (Compound 03045)

The intermediate N-(4-bromo-2,6-dimethylphenyl)-3,3-dimethyl butanamide (528 mg, 1.78 mmol) and sodium tert-butoxide (620 mg, 6.5 mmol) were added into a solution of compound 7 (270 mg, 1.62 mmol) in tert-butanol (30 mL), replaced nitrogen for three times, then methanesulfonic acid (2-dicyclohexylphosphino-2',6'-diisopropoxy-1,1'-biphenyl)(2-amino-1,1'-biphenyl-2-yl)palladium(II) (229 mg, 0.27 mmol) was added, the reaction mixture was heated to 95° C. under nitrogen protection and reacted overnight, filtered and concentrated to remove the solvent. The residue was subjected to column chromatography to obtain crude compound 03045, which was further purified by preparative chromatography to obtain compound 03045 (15 mg, yield: 2.4%).

MS (ESI): Calcd. for $C_{23}H_{32}N_2OS$ 384; Found 385 $[M+H]^+$.

1H NMR (400 MHz, MeOD): δ7.04 (s, 2H), 6.69 (s, 1H), 4.65 (s, 2H), 3.96-3.92 (m, 2H), 3.04-3.00 (m, 2H), 2.39 (s, 3H), 2.33 (s, 2H), 2.25 (s, 6H), 2.07 (s, 2H), 1.15 (s, 9H).

Example 13 Preparation of Compound 03046

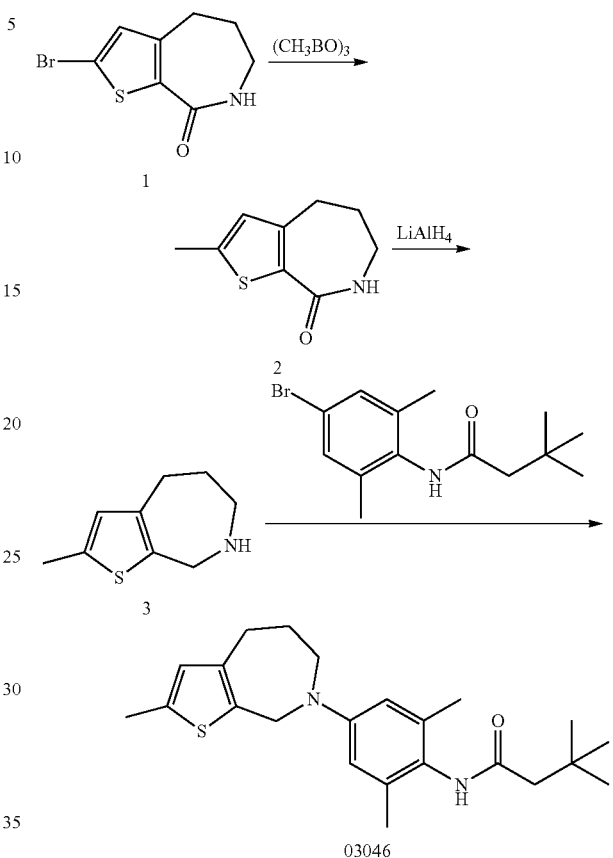

Step One: 2-methyl-4,5,6,7-tetrahydro-8H-thieno[2,3-c]azepin-8-one (Compound 2)

Potassium carbonate (2.5 g, 0.018 mol) was added to a solution of compound 1 (1.5 g, 0.006 mol) in 1,4-dioxane (50 mL), replaced nitrogen for three times, and then tetrakis (triphenylphosphine) Palladium (1.42 g, 0.0012 mol) and 2,4,6-trimethyl-1,3,5,2,4,6-trioxatriborinane (775 mg, 0.006 mol) were added, the reaction mixture was reacted overnight at 100° C., then filtered, extracted, and concentrated. The residue was subjected to column chromatography to obtain crude compound 2 (1.5 g).

MS (ESI): Calcd. for $C_9H_{11}NOS$ 181; Found 182 $[M+H]^+$.

Step Two: 2-methyl-5,6,7,8-tetrahydro-4H-thieno[2,3-c]azepine (Compound 3)

Under ice cooling, compound 2 (1.5 g, 0.008 mol) was slowly added into a suspension of lithium aluminum hydride (0.9 g, 0.024 mol) in tetrahydrofuran (50 mL). The mixture was stirred at 70° C. for 1 hour, and then water (1 mL), sodium hydroxide aqueous solution (15%, 1 mL) and water (3 mL) were slowly added in sequence, and then sufficient anhydrous magnesium sulfate was added, filtrated, concentrated, and the residue was subjected to column chromatography to obtain compound 8 (500 mg, yield: 36.5%).

MS (ESI): Calcd. for $C_9H_{13}NS$ 167; Found 168 $[M+H]^+$.

Step Three: N-(2,6-dimethyl-4-(2-methyl-4,5,6,8-tetrahydro-7H-thieno[2,3-c]azepin-7-yl)phenyl)-3,3-dimethylbutanamide (Compound 03046)

The intermediate N-(4-bromo-2,6-dimethylphenyl)-3,3-dimethyl butanamide (897 mg, 3 mmol) and sodium tert-butoxide (1.05 g, 10.9 mmol) were added into a solution of compound 3 (500 mg, 2.7 mmol) in tert-butanol (50 mL). After replacing nitrogen for three times, methanesulfonic acid (2-dicyclohexylphosphino-2',6'-diisopropoxy-1,1'-biphenyl)(2-amino-1,1'-biphenyl-2-yl)palladium(II) (390 mg, 0.46 mmol) was added. The reaction mixture was reacted overnight at 95° C. under nitrogen protection, filtered and concentrated to remove the solvent. The residue was subjected to column chromatography to obtain crude compound 03046, which was further purified by preparative chromatography to obtain compound 03046 (46 mg, yield: 4.3%).

MS (ESI): Calcd. for $C_{23}H_{32}N_2OS$ 384; Found 385 [M+H]$^+$.

1H NMR (400 MHz, CD$_3$OD): δ6.79-6.74 (m, 2H), 4.68 (s, 2H), 3.93-3.88 (m, 2H), 2.84-2.79 (m, 2H), 2.29 (s, 2H), 2.17 (s, 6H), 2.11 (s, 3H), 1.95-1.87 (m, 2H), 1.13 (s, 9H).

Example 14 Preparation of Compound 03049

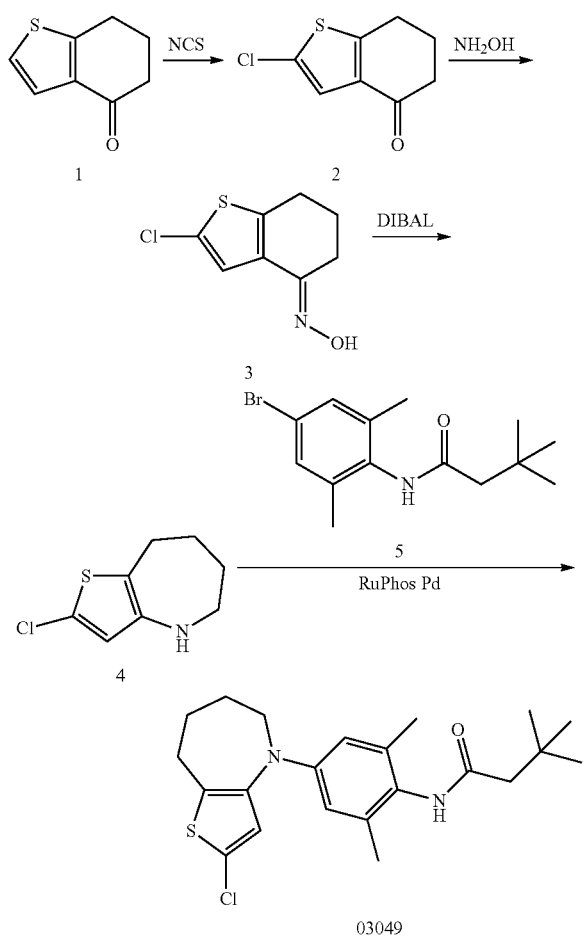

03049

Step One: 2-chloro-6,7-dihydrobenzo[b]thiophene-4(5H)-one (Compound 2)

N-chlorosuccinimide (3.2 g, 23.96 mmol) was added to a solution of 6,7-dihydrobenzo[b]thiophene-4(5H)-one (3.0 g, 19.74 mmol) in acetic acid (30 mL) in batch, the reaction mixture was heated to 50° C. and reacted for 16 hours. The mixture was cooled to room temperature, evaporated to remove most of the solvent, extracted with ethyl acetate, dried with anhydrous sodium sulfate, filtered, concentrated and subjected to column chromatography to obtain compound 2 (3.6 g crude product, yield: 100%).

MS (ESI): Calcd. for $C_8H_7ClOS$ 186; Found 187 [M+H]$^+$.

Step Two: 2-chloro-6,7-dihydrobenzo[b]thiophene-4(5H)-ketoxime (Compound 3)

Hydroxylamine hydrochloride (3.9 g, 56.52 mmol) and sodium acetate (4.6 g, 56.52 mmol) were added into a mixed solution of compound 2 (3.6 g, 19.30 mmol) in ethanol (50 mL) and water (10 mL), and the mixture was heated to reflux for 1 hour. The mixture was cooled to room temperature, concentrated to remove the solvent, and the residue was subjected to column chromatography to obtain compound 3 (3.9 g crude product, yield: 100%).

MS (ESI): Calcd. for $C_8H_8ClNOS$ 201; Found 202 [M+H]$^+$.

Step Three: 2-chloro-5,6,7,8-tetrahydro-4H-thieno[3,2-b]azepine (Compound 4)

In an ice-water bath, a solution of diisobutylaluminum hydride in n-hexane (1 mol/L, 10 mL) was added dropwise into a solution of compound 3 (1.0 g, 4.90 mmol) in dichloromethane (30 mL). The mixture was slowly raised to room temperature under the protection of nitrogen, and stirred at room temperature for 3 hours. When the temperature was lowered to 0° C., water (0.4 mL), sodium hydroxide aqueous solution (15%, 0.4 mL) and water (1.0 mL) were slowly added in sequence, then enough anhydrous magnesium sulfate was added, filtered, concentrated, the residue was subjected to column chromatography to obtain compound 4 (340 mg, yield: 36.6%).

MS (ESI): Calcd. for $C_8H_{10}ClNS$ 187; Found 188 [M+H]$^+$.

Step Four: N-(4-(2-chloro-5,6,7,8-tetrahydro-4H-thieno[3,2-b]azepin-4-yl)-2,6-dimethylphenyl)-3,3-dimethylbutanamide (Compound 03049)

N-(4-bromo-2,6-dimethylphenyl)-3,3-dimethyl butanamide (1.19 g, 4.00 mmol), sodium tert-butoxide (1.03 g, 10.70 mmol), methanesulfonic acid (2-dicyclohexylphosphino-2',6'-diisopropoxy-1,1'-biphenyl)(2-amino-1,1'-biphenyl-2-yl)palladium(II) (224 mg, 0.27 mmol) were added into a solution of compound 5 (500 mg, 2.67 mmol) in tert-butanol (20 mL) under nitrogen atmosphere. The mixture was reacted at 90° C. for sixteen hours. After the mixture was cooled to room temperature, filtered, the filtrate was concentrated in vacuo to remove the solvent, and the residue was purified by column chromatography to obtain the crude product, which was then separated by preparative chromatography to obtain compound 03049 (27.02 mg, yield: 2.5%).

MS (ESI): Calcd. for $C_{22}H_{29}ClN_2OS$ 404; Found 405 [M+H]$^+$.

HNMR (400 MHz, CD$_3$OD): δ6.67 (s, 1H), 6.50 (s, 2H), 3.71-3.68 (m, 2H), 2.71-2.68 (m, 2H), 2.30 (s, 2H), 2.15 (s, 6H), 1.90-1.86 (m, 2H), 1.72-1.71 (m, 2H), 1.15 (s, 9H).

Example 15 Preparation of Compound 03058

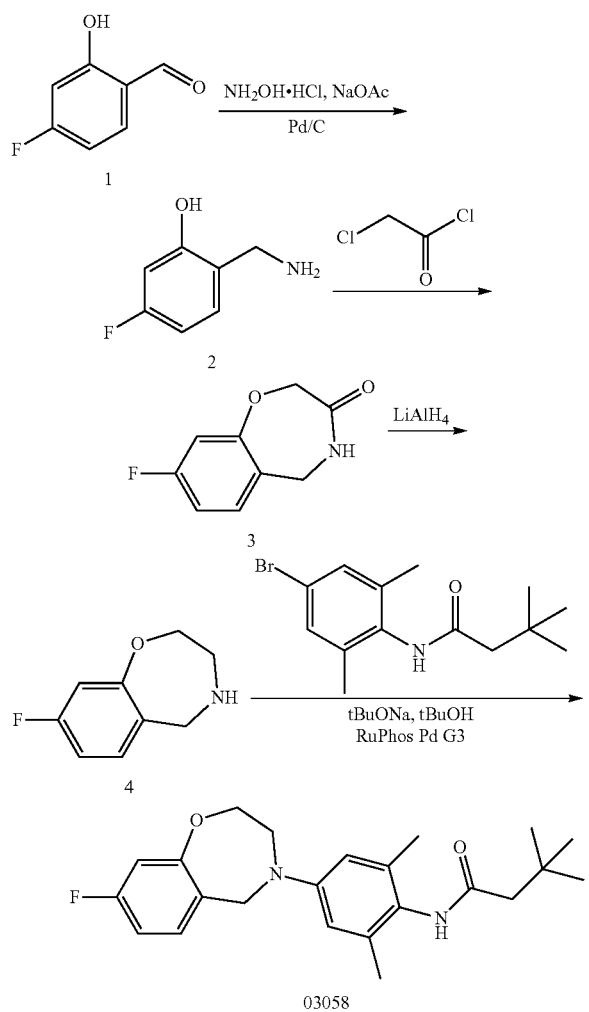

Step One: 2-(aminomethyl)-5-fluorophenol (Compound 2)

Hydroxylamine hydrochloride (1.5 g, 21.59 mmol) and sodium acetate (2.34 g, 28.54 mmol) were added into a solution of 4-fluoro-2-hydroxybenzaldehyde (1.0 g, 7.14 mmol) in ethanol (50 mL), and the mixture was heated to reflux for two hours. The mixture was cooled to room temperature, concentrated to remove the solvent, extracted with ethyl acetate, dried over anhydrous sodium sulfate, filtered, concentrated to remove the solvent to obtain a crude product. The crude product was dissolved in ethanol (50 mL), and concentrated hydrochloric acid (3.5 mL) and 10% palladium on carbon (300 mg) were added. The mixture was stirred at room temperature under 0.4 MPa hydrogen atmosphere for 16 hours, filtered with suction, and the filtrate was adjusted to pH8 with sodium bicarbonate. After concentration, the residue was purified by column chromatography to obtain compound 2 (1.0 g, yield: 100%).

MS (ESI): Calcd. for $C_7H_8FNO$ 141; Found 125 $[M-NH_2]^+$.

Step Two: 8-fluoro-4,5-dihydrobenzo[f][1,4]oxazepin-3(2H)-one (Compound 3)

Chloroacetyl chloride (88 mg, 0.78 mmol), potassium carbonate (294 mg, 2.13 mmol) and tetrabutyl ammonium bromide (23 mg, 0.071 mmol) were added into a solution of compound 2 (100 mg, 0.71 mmol) in acetonitrile (10 mL) consequently. The reaction mixture was heated to 80° C. under the protection of nitrogen and reacted for 16 hours. The mixture was cooled to room temperature, suction filtered, the filtrate was concentrated in vacuo, and purified by column chromatography to obtain compound 3 (80 mg, yield: 62.5%).

MS (ESI): Calcd. for $C_9H_8FNO2$ 181; Found 182 $[M+H]^+$.

Step Three: 8-fluoro-2,3,4,5-tetrahydrobenzo[f][1,4] oxazepine (Compound 4)

Compound 3 (800 mg, 2.99 mmol) was added to a suspension of lithium tetrahydroaluminum (420 mg, 11.05 mmol) in tetrahydrofuran (20 mL). The mixture was stirred at room temperature for 16 hours under a nitrogen atmosphere. The reaction system was quenched with water (0.42 mL), 15% sodium hydroxide in water (0.42 mL) and water (1.26 mL), dried over anhydrous magnesium sulfate, filtered with suction. The filter cake was washed with dichloromethane, the filtrate was concentrated, and purified by column chromatography to obtain compound 4 (583 mg, yield: 79.0%).

MS (ESI): Calcd. for $C_9H_{10}FNO$ 167; Found 168 $[M+H]^+$.

Step Four: N-(4-(8-fluoro-2,3-dihydrobenzo[f][1,4] oxazepin-4(5H)-yl)-2,6-dimethylphenyl)-3,3-dimethylbut anamide (Compound 03058)

N-(4-bromo-2,6-dimethylphenyl)-3,3-dimethyl butanamide (1.04 g, 3.49 mmol), sodium tert-butoxide (1.34 g, 13.97 mmol), methanesulfonic acid (2-dicyclohexylphosphino-2',6'-diisopropoxy-1,1'-biphenyl)(2-amino-1,1'-biphenyl-2-yl)palladium(II) (292 mg, 0.35 mmol) were added into a solution of compound 4 (583 mg, 3.49 mmol) in tert-butanol (20 mL) under nitrogen atmosphere. The mixture was reacted at 90° C. for sixteen hours. After the mixture was cooled to room temperature, filtered, the filtrate was concentrated in vacuo to remove the solvent, and the residue was purified by column chromatography to obtain the crude product, which was then separated by preparative chromatography to obtain compound 03058 (78.91 mg, yield: 5.9%).

MS (ESI): Calcd. for $C_{23}H_{29}FN_2O_2$ 384; Found 385 $[M+H]^+$.

HNMR (400 MHz, $CD_3OD$): δ7.41-7.31 (m, 1H), 6.75-6.61 (m, 4H), 4.61 (s, 2H), 4.16-4.15 (m, 2H), 3.90-3.88 (m, 2H), 2.27 (s, 2H), 2.14 (s, 6H), 1.14 (s, 9H).

Example 16 Preparation of Compound 03059

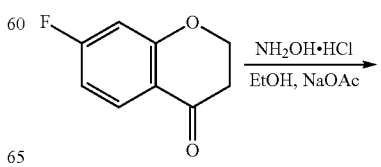

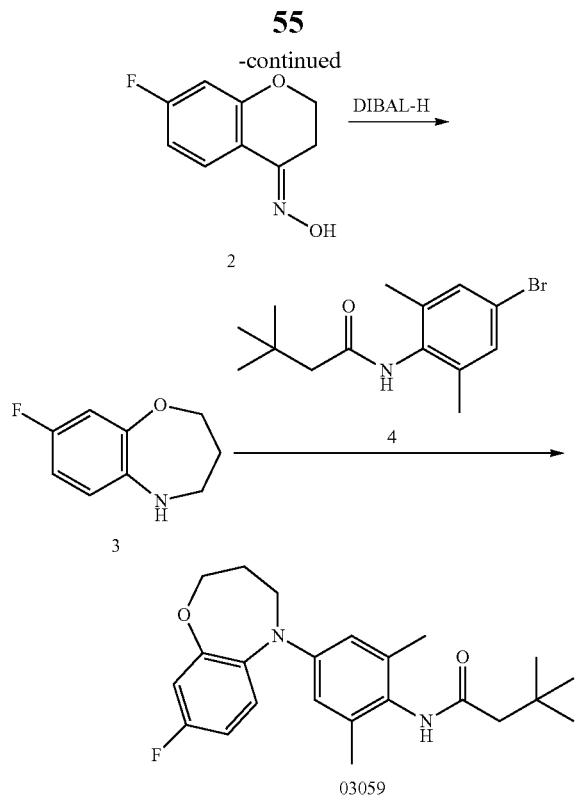

Step One: 7-fluorochroman-4-oxime (Compound 2)

At room temperature, sodium acetate (1.6 g, 19.7 mmol), hydroxylamine hydrochloride (1.3 g, 19.7 mmol) and water (2 mL) were added into a solution of 7-fluorochroman-4-one (1.0 g, 6.5 mmol) in ethanol (10 mL) consequently, the reaction mixture was heated to 90° C. and reacted for 2 hours. The mixture was cooled to room temperature, diluted with water, extracted with ethyl acetate, dried over anhydrous sodium sulfate, filtered, concentrated, and purified by Flash to obtain solid compound 2 (1.10 g, yield: 93.4%).

MS (ESI): Calcd. for $C_9H_8FNO_2$ 181; Found 182 $[M+H]^+$.

Step Two: 8-fluoro-2,3,4,5-tetrahydrobenzo[b][1,4]oxazepine (Compound 3)

In an ice bath, diisobutylaluminum hydride solution (1 N, 30.37 mL) was slowly added to a solution of compound 2 (1.1 g, 6.07 mmol) in dichloromethane (30 mL), and the mixture was stirred at room temperature under nitrogen protection for 5 hours, then water (1.2 mL), 10% sodium hydroxide (1.2 mL) and water (3.6 mL) were added in sequence, stirred at room temperature for 30 minutes, filtered. The filter cake was washed with ethyl acetate, and the filtrate was extracted with ethyl acetate, washed with saturated brine, dried with anhydrous sodium sulfate, concentrated, and purified by Flash to obtain compound 3 (0.9 g, yield: 88.3%).

MS (ESI): Calcd. for $C_9H_{10}FNO$ 167; Found 168 $[M+H]^+$.

Step Three: N-(4-(8-fluoro-3,4-dihydrobenzo[b][1,4]oxazepine-5(2H)-yl)-2,6-dimethylphenyl)-3,3-dimethylbutanamide (Compound 03059)

Ruphos-Pd-G3 (150.5 mg, 0.18 mmol), sodium tert-butoxide (695 mg, 7.16 mmol) and compound 4 (586 mg, 1.79 mmol) were added into a solution of compound 3 (300 mg, 1.79 mmol) in tert-butanol (10 mL). The mixture was stirred overnight at 80° C. under nitrogen. The mixture was cooled to room temperature, filtered, washed with ethyl acetate, and concentrated residue was purified by Flash (ethyl acetate/petroleum ether=1/5) to obtain light yellow compound 03059 (470.08 mg, yield: 78.5%).

MS (ESI): Calcd. for $C_{23}H_{29}FN_2O_2$ 384; Found 385 $[M+H]^+$.

$^1$H NMR (400 MHz, CDCl$_3$) δ7.10-7.02 (m, 1H), 6.75-6.66 (m, 1H), 6.68-6.60 (m, 1H), 6.57 (s, 2H), 6.50 (s, 1H)), 4.12 (t, J=6.0 Hz, 2H), 3.87 (t, J=6.0 Hz, 2H), 2.29 (s, 2H), 2.17 (s, 6H), 2.17-2.07 (m, 2H), 1.16 (s, 9H).

Example 17 Preparation of Compound 03063

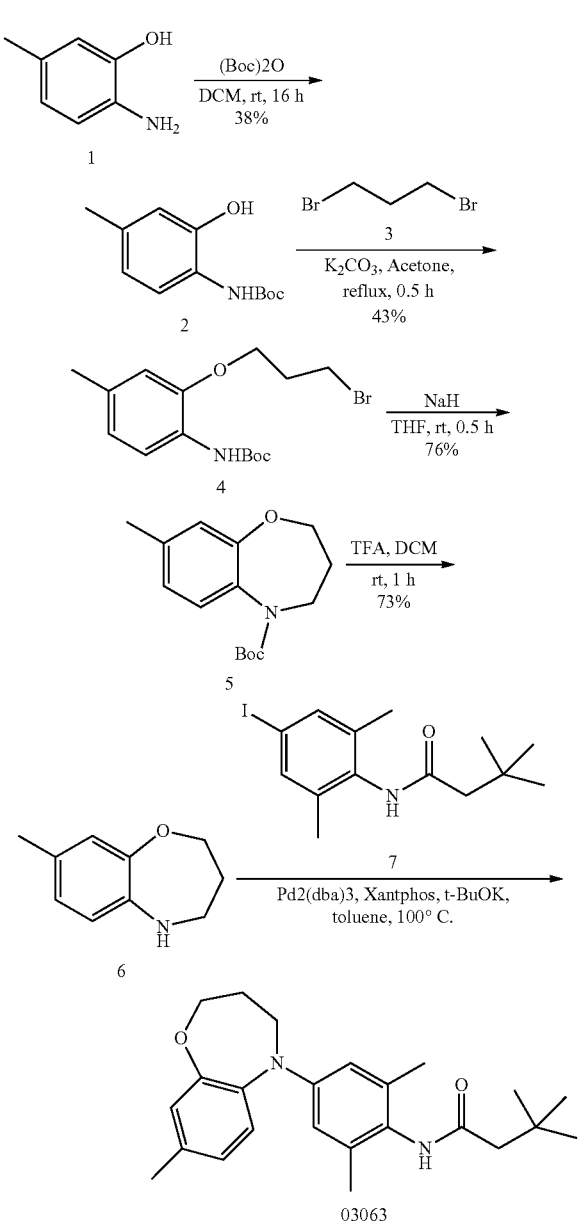

Step One: (2-hydroxy-4-methylphenyl) tert-butyl carbamate (Compound 2)

BOC$_2$O (10.63 g, 48.717 mmol) and triethylamine (14.79 g, 146.151 mmol) were added into a solution of 2-amino-5-methylphenol 1 (6 g, 48.717 mmol) in dichloromethane (60 mL). The mixture was stirred overnight at room temperature. The mixture was washed with water and saturated NaCl solution, dried with Na$_2$SO$_4$, concentrated and purified by column chromatography (n-hexane/ethyl acetate=10:1) to obtain (2-hydroxy-4-methylphenyl) carbamate tert-butyl ester 2 (4.2 g, 38%).

LCMS: [M+Na]$^+$=246.2

Step Two: tert-butyl (2-(3-bromopropoxy)-4-methylphenyl)carbamate (Compound 4)

1,3-dibromopropane (3.1 g, 15.695 mmol) and K$_2$CO$_3$ (4.96 g, 35.874 mmol) were added into a solution of tert-butyl (2-hydroxy-4-methylphenyl) carbamate 2 (1 g, 4.484 mmol) in acetone (30 mL). The mixture was stirred at 75° C. for 0.5 hour. After cooling to room temperature, the mixture was diluted with ethyl acetate and filtered. The filtrate was concentrated and purified by column chromatography (n-hexane/ethyl acetate=15:1) to obtain tert-butyl (2-(3-bromopropoxy)-4-methylphenyl)carbamate 4 (660 mg, 43%), as a colorless oil.

LCMS: [M+Na]$^+$=366.1.

Step Three: 8-methyl-3,4-dihydrobenzo[b][1,4]oxazepine-5(2H)-carboxylic acid tert-butyl ester (Compound 5)

NaH (60%, 307 mg, 7.674 mmol) was added to a solution of tert-butyl (2-(3-bromopropoxy)-4-methylphenyl)carbamate 4 (660 mg, 1.918 mmol) in THF (20 mL), the mixture was stirred at room temperature for 0.5 hours. The mixture was poured into ice water, extracted with ethyl acetate (2×20 mL), washed with water and saturated sodium chloride solution, dried over anhydrous sodium sulfate, concentrated, and purified by column chromatography (n-hexane/ethyl acetate=15:1) to obtain 8-methyl-3,4-dihydrobenzo[b][1,4]oxazepine-5(2H)-carboxylic acid tert-butyl ester 5 (385 mg, 76%) as a white solid.

LCMS: [M+Na]$^+$=286.2

Step Four: 8-methyl-2,3,4,5-tetrahydrobenzo[b][1,4]oxazepine (Compound 6)

4 ml of trifluoroacetic acid was added to a solution of 8-methyl-3,4-dihydrobenzo[b][1,4]oxazepine-5(2H)-carboxylic acid tert-butyl ester 5 (385 mg, 1.464 mmol) in dichloromethane (4 mL), and the mixture was stirred at room temperature for 1 hour. The mixture was concentrated and 30 ml of dichloromethane was added to dissolve the residue. The solution was washed with saturated NaHCO$_3$ solution and saturated sodium chloride solution, dried over anhydrous sodium sulfate, concentrated and purified by column chromatography (n-hexane/ethyl acetate=7:3) to obtain 8-methyl-2,3,4,5-tetrahydrobenzo[b][1,4]oxazepine 6 (175 mg, 73%) as a brown oil.

LCMS: [M+H]$^+$=164.2.

Step Five: N-(2,6-dimethyl-4-(8-methyl-3,4-dihydrobenzo[b][1,4]oxazepine-5(2H)-yl)phenyl)-3,3-dimethylbutanamide (03063)

N-(4-iodine-2,6-dimethylphenyl)-3,3-dimethylbutanamide 7 (1.12 g, 3.25 mmol), Pd$_2$(dba)$_3$ (229 mg, 0.25 mmol), Xantphos (289 mg, 0.50 mmol)) And t-BuOK (842 mg, 7.50 mmol) was added to a solution of 8-methyl-2,3,4,5-tetrahydrobenzo[b][1,4]oxazepin 6 (408 mg, 2.50 mmol) in toluene (25 mL). The mixture was stirred at 100° C. for 16 hours under a nitrogen atmosphere. The mixture was filtered, and the filtrate was concentrated, and purified by column chromatography (dichloromethane/methanol=30:1) to obtain a yellow oil. Purified by preparative HPLC (column: Kromasil-C18 100×21.2 mm, 5 um mobile phase: ACN-H$_2$O (0.05% NH$_3$) gradient: 35-45) to obtain the target compound 03063 (30.4 mg, 0.08 mmol, 3%) as an off-white solid.

LCMS: [M+H]$^+$=381.3.

$^1$H NMR (400 MHz, DMSO) δ8.83 (s, 1H), 7.03-6.74 (m, 3H), 6.48 (s, 2H), 3.98 (s, 2H), 3.78 (s, 2H), 2.31-1.97 (m, 13H), 1.05 (s, 9H).

Example 18 Preparation of Compound 03066

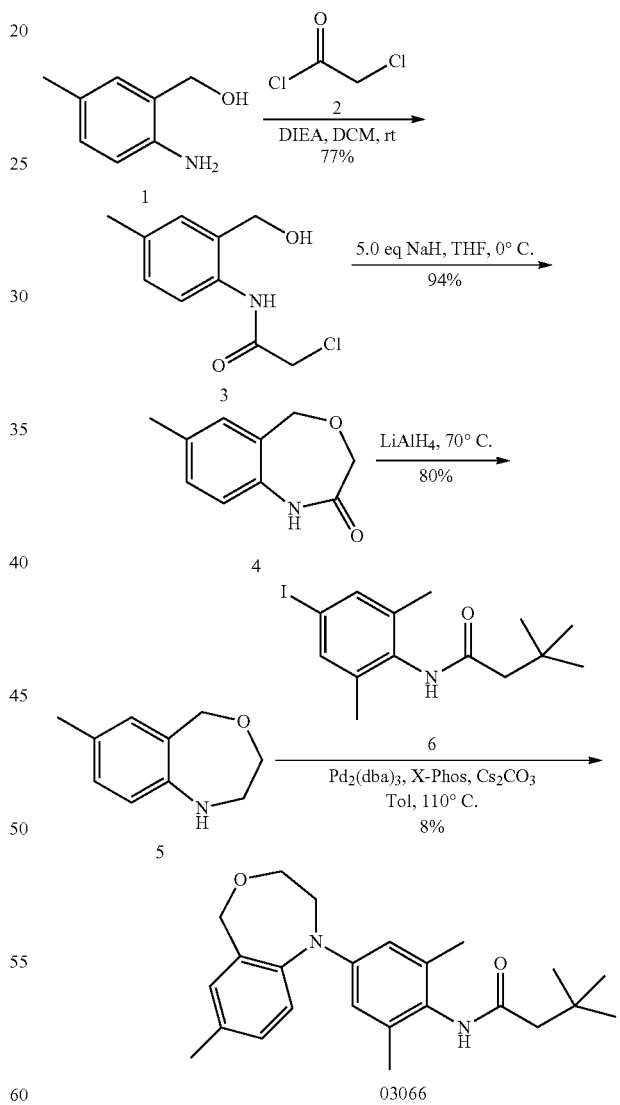

Step One: 2-chloro-N-(2-(hydroxymethyl)-4-methylphenyl)acetamide (Compound 3)

2-amino-5-methylbenzyl alcohol 1 (3.0 g, 21.9 mmol), 2-chloroacetyl chloride (2.7 g, 24 mmol) and DMA (5.66 g, 43.8 mmol) were dissolved in 50 mL of dichloromethane and stirred at room temperature for 2 hours. The reaction solution was quenched with saturated sodium bicarbonate solution, the organic layer was separated and washed with water (2×50 mL) and saturated sodium bicarbonate solution (2×50 mL), dried over anhydrous sodium sulfate, concentrated and purified by column chromatography (n-hexane/ethyl acetate=5/1) to obtain 2-chloro-N-(2-(hydroxymethyl)-4-methylphenyl)acetamide 3 (3.6 g, 77%) as a yellow solid.

LCMS: [M+H]$^+$=196.1

Step Two: 7-methyl-1,5-dihydrobenzo[e][1,4]oxazepine-2(3H)-one (Compound 4)

At 0° C., NaH (600 mg, 25 mmol) was added to a solution of 2-chloro-N-(2-(hydroxymethyl)-4-methylphenyl)acetamide 3 (2.6 g, 12.5 mmol) in tetrahydrofuran (60 mL), the mixture was stirred at 0° C. for 1 hour, then slowly quenched by adding water, and then ethyl acetate (2×50 mL) was added. The organic layer was washed with water (2×50 mL) and saturated sodium bicarbonate solution (2×50 mL), dried over anhydrous sodium sulfate, concentrated and purified by column chromatography (n-hexane/ethyl acetate=3/1) to obtain 7-methyl-1,5-dihydrobenzo[e][1,4]oxazepine-2(3H)-one 4 (2.1 g, 94%) as a yellow solid.

LCMS: [M+H]$^+$=178.1

Step Three: 7-methyl-1,2,3,5-tetrahydrobenzo[E][1,4]oxazepine (Compound 5)

LiAlH$_4$ (350 mg, 9.15 mmol) was slowly added into a solution of 7-methyl-1,5-dihydrobenzo[e][1,4]oxazepine-2(3H)-one 4 (810 mg, 4.57 mmol) in tetrahydrofuran at 0° C., the reaction was refluxed for 1 hour. The solution was cooled to 0° C., and tetrahydrofuran and Na$_2$SO$_4$ solution were slowly added. The mixture was stirred for 10 minutes and then Na$_2$SO$_4$ solution was added. The mixture was filtered, the organic layer was concentrated, and purified by column chromatography (n-hexane/ethyl acetate=5/1) to obtain 7-methyl-1,2,3,5-tetrahydrobenzo[e][1,4]oxazepine 5 (600 mg, 80%) as a yellow solid.

LCMS: [M+H]$^+$=164.1

Step Four: N-(2,6-dimethyl-4-(7-methyl-2,3-dihydrobenzo[e][1,4]oxazepine-1(5H)-yl)phenyl-3,3-dimethylbutanamide (Compound 03066)

A solution of compound 5 (300 mg, 1.84 mmol), compound 6 (762 mg, 2.2 mmol), Pd$_2$(dba)$_3$ (165 mg, 0.18 mmol), X-Phos (213 mg, 0.37 mmol) and Cs$_2$CO$_3$ (1.2 g, 3.68 mmol) in toluene (15 mL) was stirred at 110° C. for 16 hours. After the reaction solution was cooled to room temperature, 10 mL of ethyl acetate was added to the mixture, and the resultant mixture was washed with saturated sodium chloride solution (2×20 mL), and dried with anhydrous sodium sulfate. The solution was concentrated and purified by preparative HPLC (0.1% FA) to obtain compound 03066 (55 mg, 8%) as a white solid.

LCMS: [M+H]$^+$=381.2

$^1$H NMR (400 MHz, DMSO) δ8.82 (br s, 1H), 7.20 (s, 1H), 7.11 (dd, J=8.4, 2.0 Hz, 1H), 7.01 (d, J=8.0 Hz, 1H), 6.40 (s, 2H), 4.42 (s, 2H), 3.74-3.70 (m, 4H), 2.30 (s, 3H), 2.16 (s, 2H), 2.01 (s, 6H), 1.04 (s, 9H).

Example 19 Preparation of Compound 03060

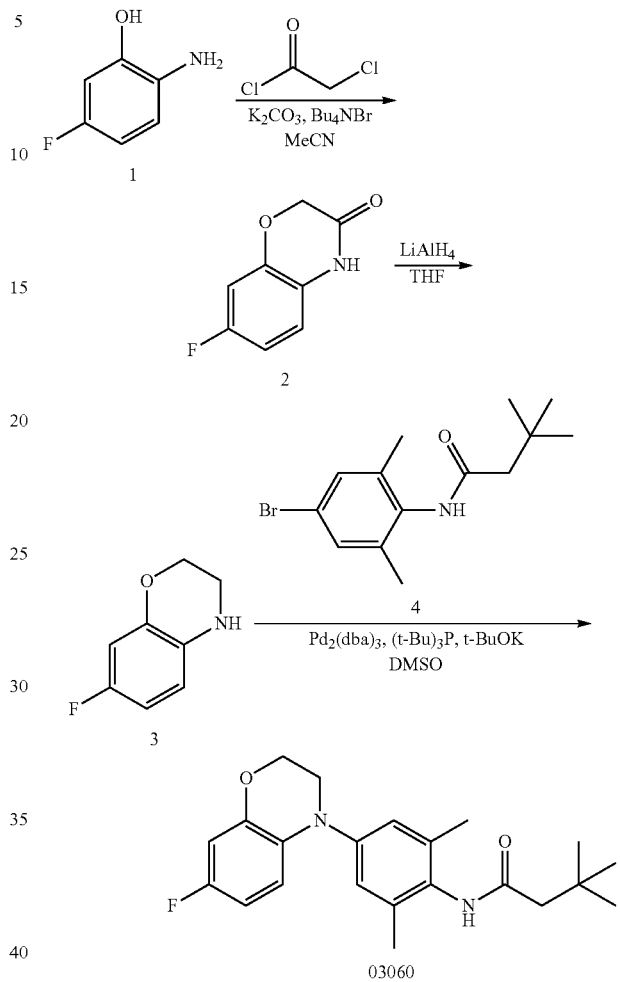

Step One: 7-fluoro-2H-benzo[1,4]oxazine-3(4H)-one (Compound 2)

Chloroacetyl chloride (490 mg, 4.33 mmol), potassium carbonate (1.63 g, 11.82 mmol) and tetrabutyl ammonium bromide (126 mg, 0.39 mmol) were added to a solution of 2-amino-5-fluorophenol (500 mg, 3.94 mmol) in acetonitrile (5 mL) consequently. The reaction mixture was heated to 65° C. under the protection of nitrogen and reacted for 15 hours. The mixture was cooled to room temperature, filtered with suction, the filtrate was concentrated in vacuo, and purified by column chromatography to obtain a yellow oily compound (500 mg, yield: 76.05%).

MS (ESI): Calcd. for $C_8H_6FNO_2$ 167; Found 168 [M+H]$^+$.

Step Two: 7-fluoro-3,4-dihydro-2H-benzo[1,4]oxazine (Compound 3)

Compound 2 (500 mg, 2.99 mmol) was added to a suspension of lithium tetrahydroaluminum (284 mg, 7.48 mmol) in tetrahydrofuran (5 mL). The mixture was stirred at room temperature for 16 hours under a nitrogen atmosphere.

The reaction system was quenched with water and 15% sodium hydroxide aqueous solution, filtered with suction, and the filtrate was extracted with ethyl acetate, concentrated, and purified by column chromatography to obtain compound 3 as a yellow oil (252 mg, yield: 55.01%).

MS (ESI): Calcd. for $C_8H_8FNO$ 153; Found 154 $[M+H]^+$.

Step Three: N-(2,6-dimethyl-6-(1-tert-butylacetyl) aniline)) 4-(7-fluoro-2,3-dihydro-4H-benzo[1,4] oxazine (Compound 03060)

Compound 4 (532 mg, 1.79 mmol), $Pd_2(dba)_3$ (126.6 mg, 0.16 mmol), and sodium tert-butoxide (632.4 mg, 6.52 mmol) were added to a solution of compound 3 (250 mg, 1.63 mmol) in tert-butanol (5 mL). The mixture was reacted at 85° C. for 15 hours. The reaction mixture was cooled to room temperature, filtered, and the filtrate was concentrated in vacuo. The residue was purified by preparative high performance liquid chromatography to obtain a white solid compound 03060 (46.40 mg, yield: 7.67%).

MS (ESI): Calcd. for $C_{22}H_{27}FN_2O_2$ 370; Found 371 $[M+H]^+$.

HNMR (400 MHz, $CD_3Cl_3$): δ6.87-6.90 (m, 3H), 6.66-6.48 (m 3H), 4.25 (t, J=4.0 Hz, 2H), 3.67 (s, 2H), 2.33 (s, 2H), 2.23 (s, 6H), 1.18 (s, 9H).

Example 20 Preparation of Compound 03037

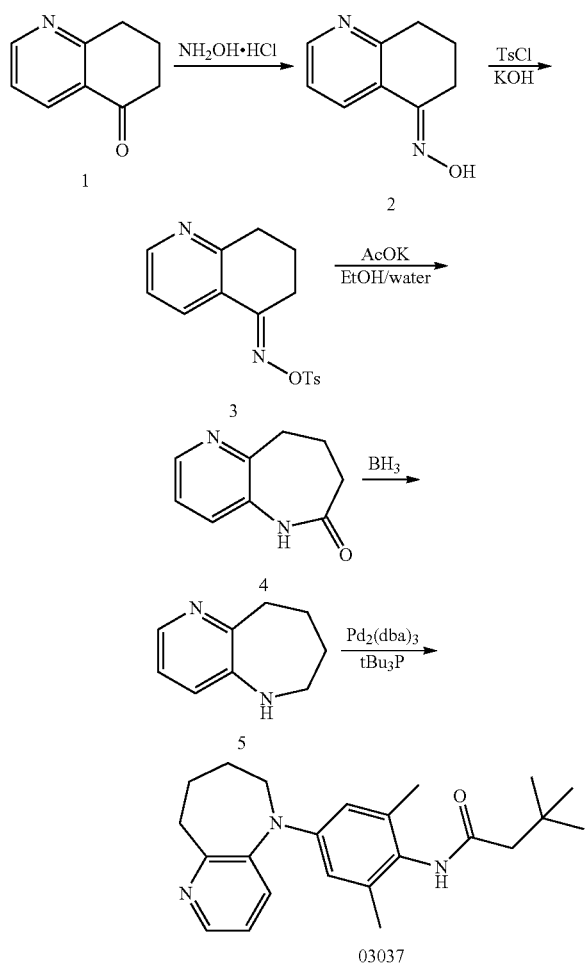

Step One: (E)-7,8-dihydroquinoline-5(6H)-one oxime (Compound 2)

Hydroxylamine hydrochloride (1.13 g, 16.29 mmol) and sodium acetate (1.34 g, 16.29 mmol) were added to a mixed solution of 7,8-dihydroquinoline-5(6H)-one (1.0 g, 6.79 mmol) in methanol/water (40 mL/6 mL), and the mixture was heated to reflux for two hours. The mixture was cooled to room temperature, concentrated to remove the solvent, water was added, filtered, and the filter cake was dried to obtain compound 2 (1.1 g crude product, yield: 100%).

MS (ESI): Calcd. for $C_9H_{10}N_2O$ 162; Found 163 $[M+H]^+$.

Step Two: (E)-7,8-dihydroquinoline-5(6H)-one-p-toluenesulfonyl oxime (Compound 3)

Potassium hydroxide (381 mg, 6.79 mmol) and water (10 mL) were added to a solution of compound 2 (1.10 g, 6.79 mmol) in acetone (25 mL), and then p-toluenesulfonyl chloride (1.94 g, 10.18 mmol) was added. The mixture was heated to reflux for 1 hour. The mixture was cooled to room temperature, concentrated to remove the solvent, water was added, filtered, and the filter cake was dried to obtain compound 3 (2.1 g crude product, yield: 100%).

MS (ESI): Calcd. for $C_{16}H_{16}N_2O_3S$ 316; Found 317 $[M+H]^+$.

Step Three: 5,7,8,9-tetrahydro-6H-pyrido[3,2-b] azepin-6-one (Compound 4)

Potassium acetate (1.5 g, 15.28 mmol) was added to a mixed solution of compound 3 (2.1 g, 6.65 mmol) in ethanol/water (20 mL/40 mL). The mixture was heated to reflux for sixteen hours. The mixture was cooled to room temperature, concentrated to remove the solvent, water was added, and PH was adjusted to be 10 with 5N sodium hydroxide. The reaction mixture was extracted with dichloromethane, dried with anhydrous sodium sulfate, filtered, concentrated to remove the solvent, and the crude product was column chromatography to obtain compound 4 (750 mg, yield: 75.0%).

MS (ESI): Calcd. for $C_9H_{10}N_2O$ 162; Found 163 $[M+H]^+$.

Step Four: 6,7,8,9-tetrahydro-5H-pyrido[3,2-b] azepine (Compound 5)

A solution of borane in tetrahydrofuran (1 mol/L, 14 mL) was added dropwise to a solution of compound 4 (750 mg, 4.63 mmol) in tetrahydrofuran (30 mL). The mixture was continuously stirred for 0.5 hour, and then heated to 60° C. and reacted for 2 hours. The mixture was cooled to room temperature, quenched with methanol, concentrated in vacuo to remove the solvent, and the residue was purified by column chromatography to obtain compound 5 (400 mg, yield: 58.0%).

MS (ESI): Calcd. for $C_9H_{12}N_2$ 148; Found 149 $[M+H]^+$.

Step Five: N-(2,6-Dimethyl-4-(6,7,8,9-tetrahydro-5H-pyrido[3,2-b]azepin-5-yl)phenyl)-3,3-dimethylbutanamide (Compound 03037)

Under nitrogen atmosphere, N-(4-bromo-2,6-dimethylphenyl)-3,3-dimethylbutanamide (160 mg, 0.54 mmol), $Pd_2(dba)_3$ (25 mg, 0.034 mmol), tri-tert-butylphosphorus n-hexane solution (0.1 mL) and potassium tert-butoxide (61 mg, 0.54 mmol) were added to a solution of compound 5 (40 mg, 0.27 mmol) in DMSO (2 mL). The mixture was reacted in microwave at 150° C. for one hour. After the mixture was cooled to room temperature, the reaction mixture was quenched with water, extracted with ethyl acetate, dried over anhydrous sodium sulfate, concentrated in vacuo to remove the solvent, and the residue was purified by column chromatography to obtain the crude product, which was further purified by preparative chromatography to obtain compound 03030 (13.59 mg, yield: 11.0%).

MS (ESI): Calcd. for $C_{23}H_{31}N_3O$ 365; Found 366 $[M+H]^+$.

HNMR (400 MHz, $CD_3OD$): δ8.29 (s, 1H), 7.97-7.93 (m, 1H), 7.66-7.64 (m, 1H), 6.85 (s, 2H), 3.90-3.88 (m, 2H)), 3.33-3.25 (m, 2H), 2.34 (s, 2H), 2.21 (s, 6H), 1.99-195 (m, 4H), 1.16 (s, 9H).

Activity Test of Potassium Ion Channel Opener (FDSS/μCELL Detection)

1. Experimental Method

1.1 Experimental Process

Cell preparation: CHO-KCNQ2 cells were cultured in a 175 $cm^2$ culture flask, and when the cells was grown to a density of 60~80%, the culture medium was removed, washed with 7 mL PBS (Phosphate Buffered Saline) once, then 3 mL 0.25% Trypsin was added to digest. After the digestion was completed, 7 mL culture medium (90% DMEM/F12+10% FBS+500 μg/mL G418) was added to neutralize, centrifugated for 3 minutes at 800 rpm. The supernatant was aspirated, then 5 mL culture medium was added to resuspend, and then the cells were counted.

Cell plating: The density to $3×10^4$/well was adjusted according to the results of cell counting. After standing at room temperature for 30 minutes, the cells were placed in a 37° C. $CO_2$ incubator and incubated overnight for 16-18 hours. The cell density reached about 80%.

Fluorescent dye incubation: The cell culture medium was discarded, 80 μL/well loading buffer was added, and the cells were incubated in dark at room temperature for 60 minutes.

Compound incubation: the loading buffer was discarded, 80 μL/well prepared compound solution was added, incubated at room temperature and in dark for 20 minutes.

Fluorescence data collection: FDSS/μCELL instrument for real-time fluorescence is used for signal recording, wherein excitation wavelength was 480 nm, emission wavelength was 540 nm, and signals were recorded 1 times per second, after baseline was recorded for 10 seconds, the addition of 20 μL/well stimulation buffer was started, and then the signal was continuously record until the end of 180 seconds.

1.2 Solution Preparation loading buffer:10 mL/plate, the preparation method was as follows:

| component | volume |
|---|---|
| PowerLoad ™ Concentrate, 100× (ingredient C) | 100 μL |
| FluxOR ™ reagent, rebuild in DMSO (step 1.2) | 10 μL |
| Deionized water | 8.8 mL |
| FluxOR ™ Test Buffer, 10× (ingredient B) | 1 mL |
| Probenecid, reconstituted in deionized water (step 1.1) | 100 μL |
| Total volume | 10 mL |

Test buffer sample:100 mL/plate, the preparation method was as follows:

| component | volume |
|---|---|
| Deionized water | 8.9 mL |
| FluxOR ™ Test Buffer, 10× (ingredient B) | 1 mL |
| Probenecid, reconstituted in deionized water (step 1.1) | 100 μL |
| Total volume | 10 mL |

Stimulation buffer:5 mL/plate, the preparation method was as follows:

| component | volume + $K^+$ | volume − $K^+$ |
|---|---|---|
| Deionized water | 2.5 mL | 3.5 mL |
| FluxOR ™ Chlorine-free buffer, 5× (ingredient E) | 1 mL | 1 mL |
| $K_2SO_4$ concentrate (125 mM $K_2SO_4$ concentrated solution, ingredient F) | 1 mL | / |
| $Tl_2SO_4$ concentrate (50 mM $Tl_2SO_4$ concentrated solution, ingredient G) | 0.5 mL | 0.5 mL |
| Total volume | 5 mL | 5 mL |

The above buffer was from a commercially available kit, the kit name was FluxOR potassium ion channel assay, the manufacturer's brand was Invitrogen, the article number was F10017, the lot number was 913728.

1.3 Compound Preparation 20 mM DMSO compound mother liquor was prepared, 10 μL of 20 mM compound mother liquor was took and added into 20 μL DMSO solution, serially diluted 3 times to 8 intermediate concentrations; then the middle concentration of the compound was took to the test buffer, 200 times dilution to get the final concentration to be tested. 80 μL was took and added to the test plate.

The highest test concentration was 100 μM, followed by 100, 33.33, 11.11, 3.70, 1.23, 0.41, 0.137, 0.045 μM, total 8 concentrations. Each concentration 3 replicate holes.

The content of DMSO in the final test concentration did not exceed 0.5%. This concentration of DMSO had no effect on the KCNQ2 potassium channel.

1.4 Data Analysis

Experimental data was analyzed by Excel 2007 and GraphPad Prism 5.0 software, and the ratio of 180 seconds was calculated to calculate the excitement effect. The excitement effect of the compound is calculated by the following formula:

Percentage of excitement =

$$\frac{\text{Fluorescence signal ratio with compound} - \text{Fluorescence signal ratio without compound}}{\text{Fluorescence signal ratio without compound}} \times 100\%$$

1.5 Quality Control

Environment: Temperature about 25° C.
Reagent: FluxOR™ Detection Kit (Invitrogen, Cat #F0017)
The experimental data in the report might meet the following criteria: Z' Factor>0.5

2. Determination Results: see Table 1 for details, where the smaller $EC_{50}$ was, the higher the activity of the corresponding compound was.

TABLE 1

Test results of some compounds of the present invention

| Compound number | Compound structure | $EC_{50}$ (uM) |
|---|---|---|
| ZTZ240 (positive control) | 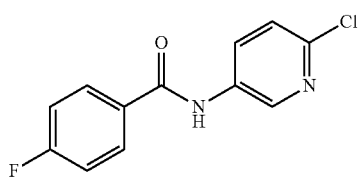 [SMILES: O=C(Nc1ccc(Cl)nc1)c1ccc(F)cc1] | 8.23 |
| Compound 03026 | 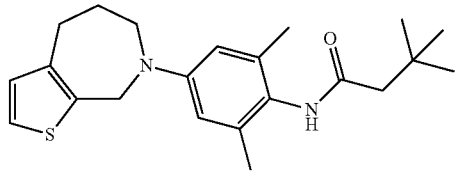 [SMILES: Cc1cc(N2CCCc3ccsc3C2)cc(C)c1NC(=O)CC(C)(C)C] | 0.088 |
| Compound 03027 | 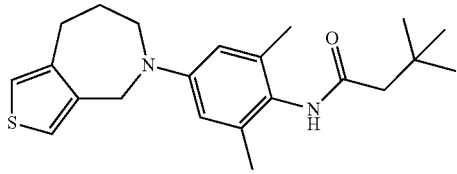 [SMILES: Cc1cc(N2CCCc3cscc3C2)cc(C)c1NC(=O)CC(C)(C)C] | 0.147 |
| Compound 03028 | 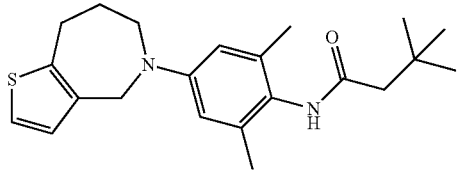 [SMILES: Cc1cc(N2CCCc3sccc3C2)cc(C)c1NC(=O)CC(C)(C)C] | 0.272 |
| Compound 03029 | 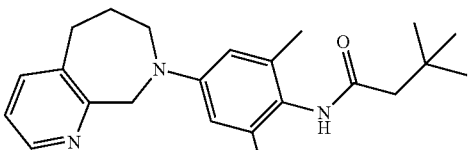 | 14.72 |
| Compound 03034 | 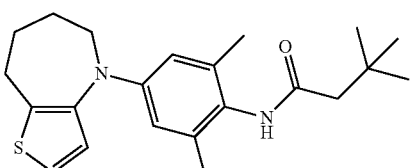 | 0.071 |

TABLE 1-continued

Test results of some compounds of the present invention

| Compound number | Compound structure | EC$_{50}$ (uM) |
|---|---|---|
| Compound 03039 | 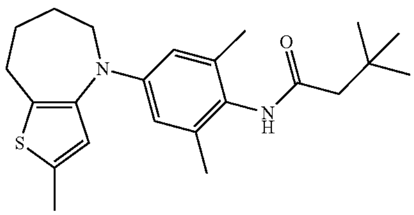 [SMILES: Cc1cc2c(s1)CCCCN2c1cc(C)c(NC(=O)CC(C)(C)C)c(C)c1] | 0.409 |
| Compound 03043 | 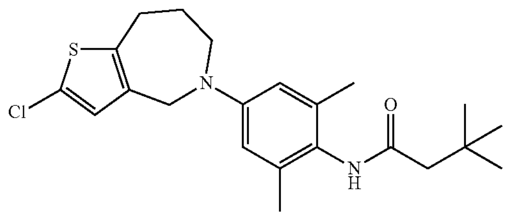 [SMILES: Cc1cc(N2CCCc3sc(Cl)cc3C2)cc(C)c1NC(=O)CC(C)(C)C] | 0.023 |
| Compound 03044 | 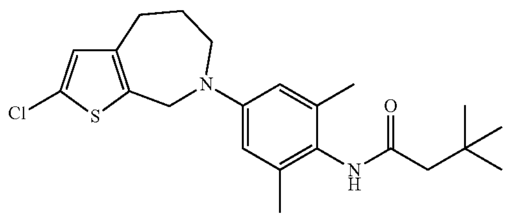 [SMILES: Cc1cc(N2CCCc3cc(Cl)sc3C2)cc(C)c1NC(=O)CC(C)(C)C] | 0.057 |
| Compound 03049 | 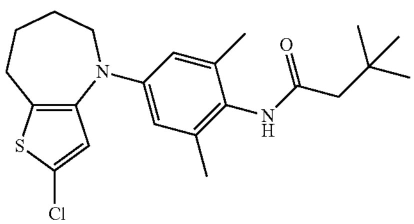 [SMILES: Cc1cc(N2CCCCc3sc(Cl)cc32)cc(C)c1NC(=O)CC(C)(C)C] | 0.260 |
| Compound 03058 | 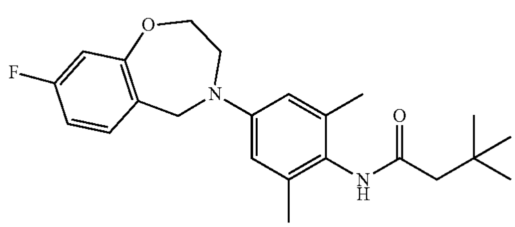 [SMILES: Cc1cc(N2CCOc3cc(F)ccc3C2)cc(C)c1NC(=O)CC(C)(C)C] | 0.008 |
| Compound 03059 | 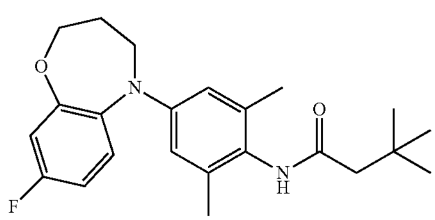 [SMILES: Cc1cc(N2CCCOc3cc(F)ccc32)cc(C)c1NC(=O)CC(C)(C)C] | 0.86 |
| Compound 03066 | 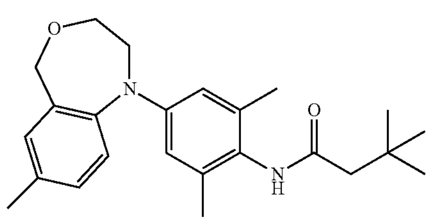 [SMILES: Cc1ccc2c(c1)COCCN2c1cc(C)c(NC(=O)CC(C)(C)C)c(C)c1] | 0.049 |

TABLE 1-continued

Test results of some compounds of the present invention

| Compound number | Compound structure | EC$_{50}$ (uM) |
|---|---|---|
| Compound 03060 | 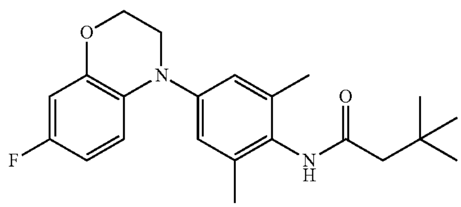 [SMILES: Cc1cc(N2CCOc3cc(F)ccc32)cc(C)c1NC(=O)CC(C)(C)C] | >100 |
| Compound 03037 | 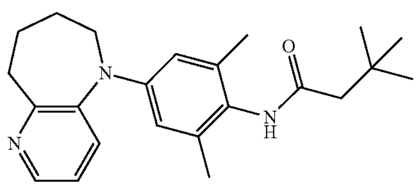 [SMILES: Cc1cc(N2CCCCc3ncccc32)cc(C)c1NC(=O)CC(C)(C)C] | 6.48 |
| Compound A (WO2014/048165 A1) | 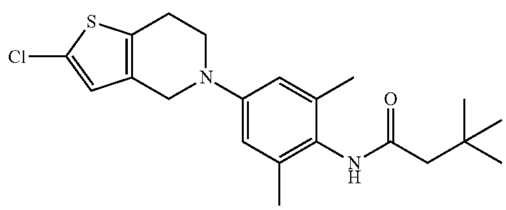 [SMILES: Cc1cc(N2CCc3sc(Cl)cc3C2)cc(C)c1NC(=O)CC(C)(C)C] | 0.065 |
| Compound B (WO2008/024398 A2) | 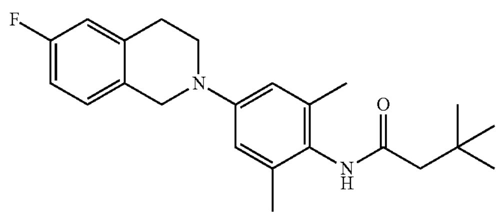 [SMILES: Cc1cc(N2CCc3cc(F)ccc3C2)cc(C)c1NC(=O)CC(C)(C)C] | 0.098 |

REFERENCES FOR THE ABOVE TEST METHODS (1) Zhaobing Gao et al. Journal of Biological Chemistry. 2010, 285(36): 28322-28332.

(2) Jinfeng Yue et al. Acta Pharmacologica Sinica. 2016, 37:105-110.

It can be known from above Table 1:

1) Comparing compound A (structural formula:

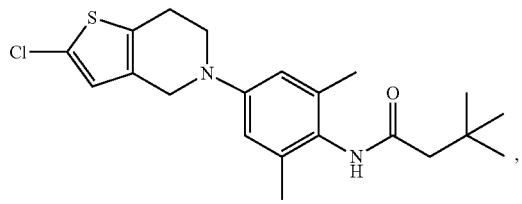 [SMILES: Cc1cc(N2CCc3sc(Cl)cc3C2)cc(C)c1NC(=O)CC(C)(C)C]

EC$_{50}$=0.065 uM) and compound 03043 (structural formula:

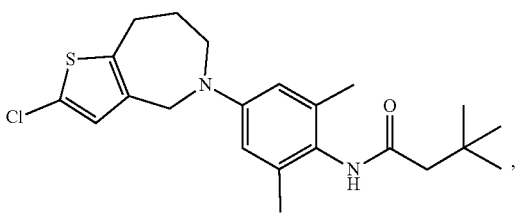 [SMILES: Cc1cc(N2CCCc3sc(Cl)cc3C2)cc(C)c1NC(=O)CC(C)(C)C]

EC$_{50}$=0.023 uM), it can be seen that after adjusting the N-containing 6-membered ring in the compound into a 7-membered ring, the activity of the obtained compound is significantly increased by about 2.83 times (=0.065/0.023);

2) Comparing compound B (structural formula:

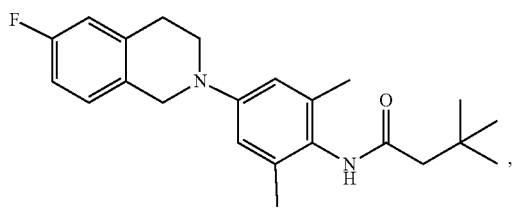 [SMILES: Cc1cc(N2CCc3cc(F)ccc3C2)cc(C)c1NC(=O)CC(C)(C)C]

$EC_{50}$=0.098 uM) and compound 03058 (structural formula:

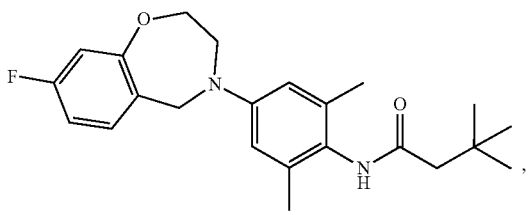 [SMILES: Cc1cc(N2CCOc3cc(F)ccc3C2)cc(C)c1NC(=O)CC(C)(C)C]

$EC_{50}$=0.008 uM), it can be seen that after adjusting the N-containing 6-membered heterocycle in the compound into a 7-membered heterocycle containing one N and one O, the activity of the obtained compound is increased significantly by 12.25 times (=0.098/0.008);

3) Comparing compound 03060 (structural formula:

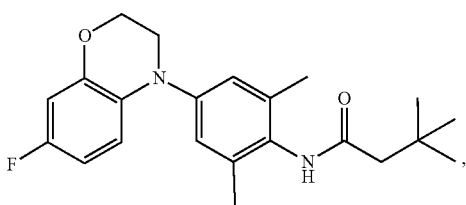 [SMILES: Cc1cc(N2CCOc3cc(F)ccc32)cc(C)c1NC(=O)CC(C)(C)C]

$EC_{50}$>100 uM) and compound 03059 (structural formula:

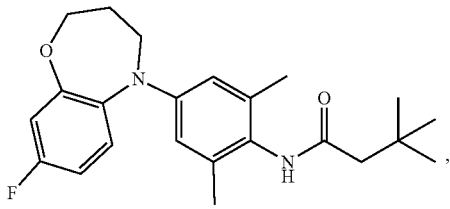 [SMILES: Cc1cc(N2CCCOc3cc(F)ccc32)cc(C)c1NC(=O)CC(C)(C)C]

$EC_{50}$=0.86 uM), it can be seen that when the 6-membered heterocycle containing one N and one O in the compound is adjusted into a 7-membered heterocycle containing one N and one O, the activity of the obtained compound is significantly increased.

Pharmacokinetic Study of Compound 03058
1) Research purpose: To obtain the pharmacokinetic characteristics of compound 03058 in male ICR mice
2) Experimental content 6 healthy male ICR mice (body weight range of 18-22 grams) were taken, divide them into 2 groups (3 mice/group, and 3 mice/time point), fasted for more than 12 hours (only oral administration group), and administered intravenously (0.05 mg/kg), orally (1 mg/kg), at time points of 0.083 (intravenous administration only), 0.25, 0.5, 1, 2, 4, 6 (only oral administration). After 8 and 24 h, blood were collected by cardiac puncture. At least 0.3 mL of whole blood was transferred to the EDTA-K2 anticoagulation tube, and within half an hour, the plasma was collected by centrifugation (6000 rpm, 8 minutes, 4° C.), and frozen at −20° C. for use. (Compound configuration: 5% DMAC+10% Solutol HS 15+85% Saline was used to prepare a solution having a concentration of iv 0.01 mg/mL and po 0.1 mg/mL).

Experimental results: According to the blood drug concentration data obtained, the non-compartmental model of WinNonlin® 7.0 software (Pharsight, USA) was used to calculate the pharmacokinetic parameters after administration.

TABLE 2

Pharmacokinetic parameters of a single dose of 03058 in male ICR mice

| parameter | unit | Intravenous 0.05 mg/kg plasma | Gavage 1 mg/kg plasma |
|---|---|---|---|
| $T_{1/2}$ | (h) | 0.73 | 1.05 |
| $T_{max}$ | (h) | / | 0.5 |
| $C_{max}$ | ng/mL | 15.1 | 17.0 |
| $AUC_{last}$ | hr*ng/mL | 7.2 | 43.6 |
| $AUC_{Inf}$ | hr*ng/mL | 7.2 | 43.6 |
| F | % | / | 30.47 |

It can be seen from the results in Table 2 that compound 03058 has good pharmacokinetic properties.

Study on the Pharmacokinetics of Compounds 03043 and 03044
1) Research purpose: To obtain the pharmacokinetic characteristics of compounds 03043 and 03044 in male SD rats and their blood-brain barrier (BBB) penetration
2) Experimental content 15 healthy male SD rats (weight range of 200-250 g) were taken and divided into 3 groups. 3 rats were used for intravenous administration in group 1, 3 rats were used for oral administration in group 2, and 9 rats were used for the determination of cerebral blood ratio after oral administration in group 3 (3 rats/time point). Group 2 and group 3 were fasted for more than 12 hours. Intravenous: 1 mg/kg, oral 5 mg/kg, at time point 0.083 (only group 1), 0.25 (only groups 1 and 2), 0.5 (only groups 1 and 2), 1, 2 (only groups 1 and 2). After 4, 8 and 24 h (only group 1 and group 2), blood was collected by jugular vein or cardiac puncture, and at least 0.3 mL of whole blood was collected into an EDTA-K2 anticoagulant tube. Within half an hour, the plasma was collected by centrifugation (6000 revolutions, 8 minutes, 4° C.), frozen at −20° C. for later use. At the same time, brain tissues were collected from group 3 (time points were 1, 4, and 8 h respectively), washed with normal saline, blotted dry with absorbent paper, weighed, and frozen at −20° C. for use. (Compound preparation: 5% DMAC+10% Solutol HS 15+85% Saline was used to prepare a solution having a concentration of iv 0.2 mg/mL and po 0.3 mg/mL).

Experimental results: According to the blood drug concentration data obtained, the non-compartmental model of WinNonlin® 7.0 software (Pharsight, USA) was used to calculate the pharmacokinetic parameters after administration.

TABLE 3

Pharmacokinetic parameters of a single dose of male SD rats

| | | Compound 03043 | | Compound 03044 | |
|---|---|---|---|---|---|
| parameter | unit | Intravenous 1 mg/kg plasma | Gavage 5 mg/kg plasma | Intravenous 1 mg/kg plasma | Gavage 5 mg/kg plasma |
| $T_{1/2}$ | (h) | 1.42 | 12.35 | 1.8 | 7.08 |
| $T_{max}$ | (h) | / | 0.25 | / | 0.67 |
| $C_{max}$ | ng/mL | 2044.6 | 128.7 | 1736.2 | 117.6 |
| $AUC_{last}$ | hr*ng/mL | 957.4 | 612.1 | 1039.3 | 722.9 |
| $AUC_{Inf}$ | hr*ng/mL | 963.7 | 1110.6 | 1058.3 | 889.0 |
| F | % | / | 12.79 | / | 13.9 |

TABLE 4

Plasma (ng/mL) and brain concentration (ng/g) in male SD rats after a single oral administration of compounds

| Compound | Time point (h) | Plasma (ng/mL) | Brain (ng/g) | Cerebral blood ratio |
|---|---|---|---|---|
| 03043 | 1 | 32.2 | 67.1 | 2.4 |
|  | 4 | 47.9 | 65.7 | 1.5 |
|  | 8 | 20.8 | 20.0 | 1.0 |
| 03044 | 1 | 112.1 | 250.8 | 2.2 |
|  | 4 | 50.2 | 102.5 | 2.1 |
|  | 8 | 41.3 | 67.6 | 1.7 |

It can be seen from the results in Table 3 that compounds 03043 and 03044 have good pharmacokinetic properties.

It can be seen from the results in Table 4 that after oral administration of compounds 03043 and 03044 to male SD rats, they have a good cerebral blood ratio (1.0-2.4) at each time point. In previous studies, we found that the cerebral blood ratio of compound A (WO2014/048165 A1) was about 0.5 (the cerebral blood ratio at 2 h was 0.56; the cerebral blood ratio at 4 h was 0.46). The above results suggest that, compared with the six-membered ring compound A, the seven-membered ring compounds 03043 and 03044 have a more excellent cerebral blood ratio.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for treating of disorder or condition in response to abnormal ion flow in potassium channel, comprising administering a compound of formula A or a pharmaceutically acceptable salt thereof into a subject in need thereof;

formula A

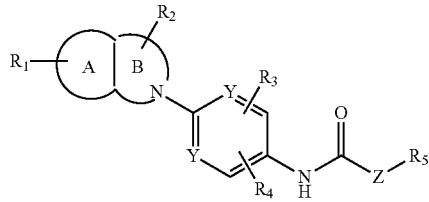

wherein:
ring B is

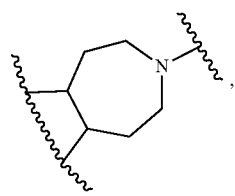

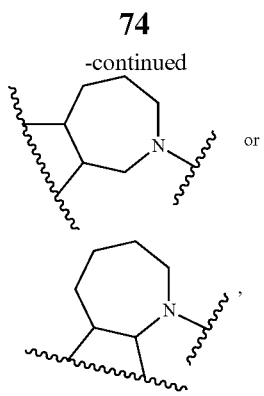

ring A is a thiophene ring; or
ring B is

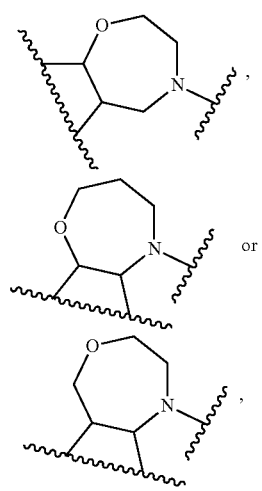

ring A is a benzene ring;
$R_1$ is a substituent on ring A;
$R_2$ is a substituent on ring B;
$R_3$ and $R_4$ are substituents on six-membered ring;
$R_1$ and $R_2$ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkylamino;
$R_3$ and $R_4$ are each independently $C_{1-6}$ alkyl;
Y is CH;
Z is $(CH_2)_n$, n is 1;
$R_5$ is $C_{1-6}$ alkyl;
the disorder or condition is selected from the group consisting of seizure symptoms;
inflammatory pain, and
amyotrophic lateral sclerosis.

2. The method of claim 1, wherein ring B is

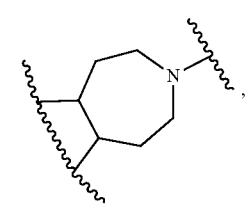

-continued

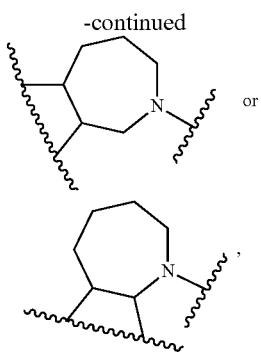

ring A is thiophene ring;
R₁ is a substituent on ring A;
R₂ is a substituent on ring B;
R₃ and R₄ are substituents on six-membered ring;
R₁ and R₂ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkylamino;
R₃ and R₄ are each independently $C_{1-6}$ alkyl;
Y is CH;
Z is $(CH_2)_n$, n is 1;
R₅ is $C_{1-6}$ alkyl.

3. The method of claim 1, wherein ring B is

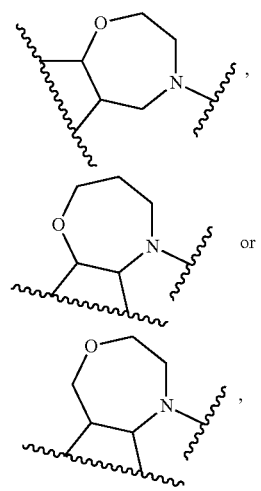

ring A is a benzene ring;
R₁ is a substituent on ring A;
R₂ is a substituent on ring B;
R₃ and R₄ are substituents on six-membered ring;
R₁ and R₂ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkylamino;
R₃ and R₄ are each independently $C_{1-6}$ alkyl;
Y is CH;
Z is $(CH_2)_n$, n is 1;
R₅ is $C_{1-6}$ alkyl.

4. The method of claim 1, wherein:
ring B is

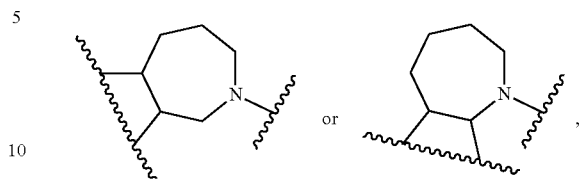

ring A is a thiophene ring;
R₁ is a substituent on ring A;
R₂ is a substituent on ring B;
R₃ and R₄ are substituents on six-membered ring;
R₁ and R₂ are each independently hydrogen, halogen, nitro, cyano, $C_{1-6}$ alkyl, $C_{1-6}$ alkoxy, halogenated $C_{1-6}$ alkyl, halogenated $C_{1-6}$ alkoxy, $C_{3-6}$ cycloalkyl, $C_{1-6}$ alkylamino;
R₃ and R₄ are each independently $C_{1-6}$ alkyl;
Y is CH;
Z is $CH_2$;
R₅ is $C_{1-6}$ alkyl.

5. The method of claim 1, wherein the compound is selected from the group consisting of:

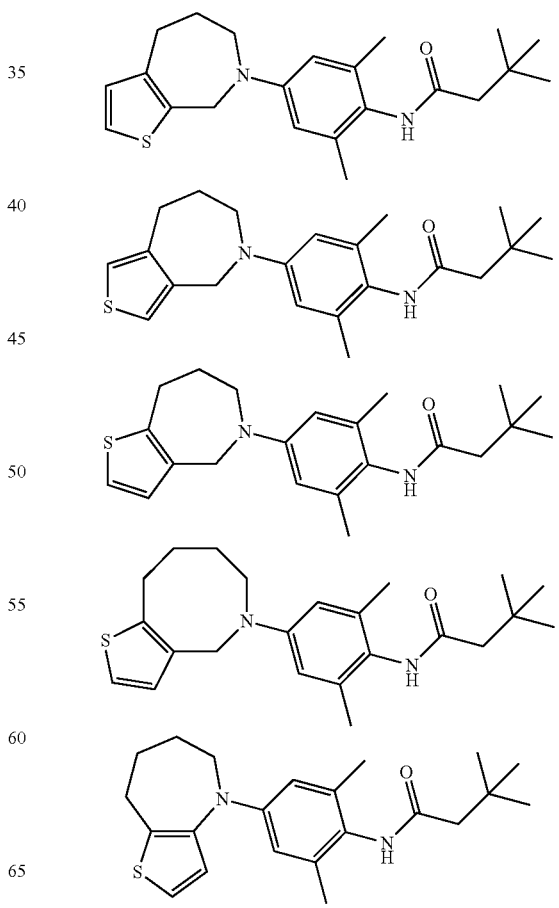

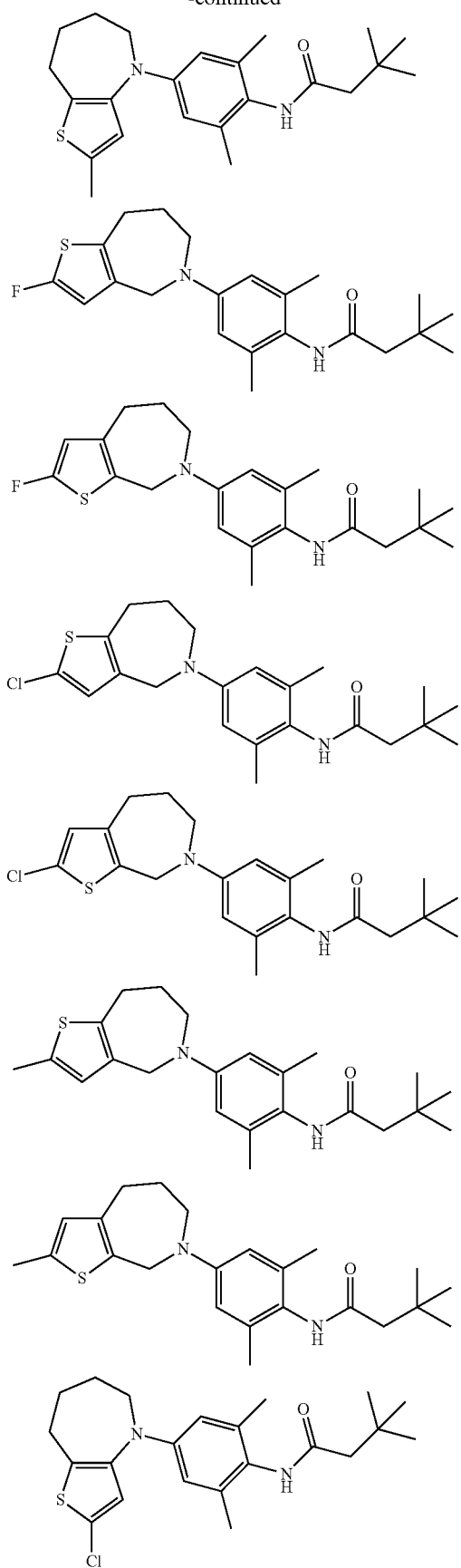
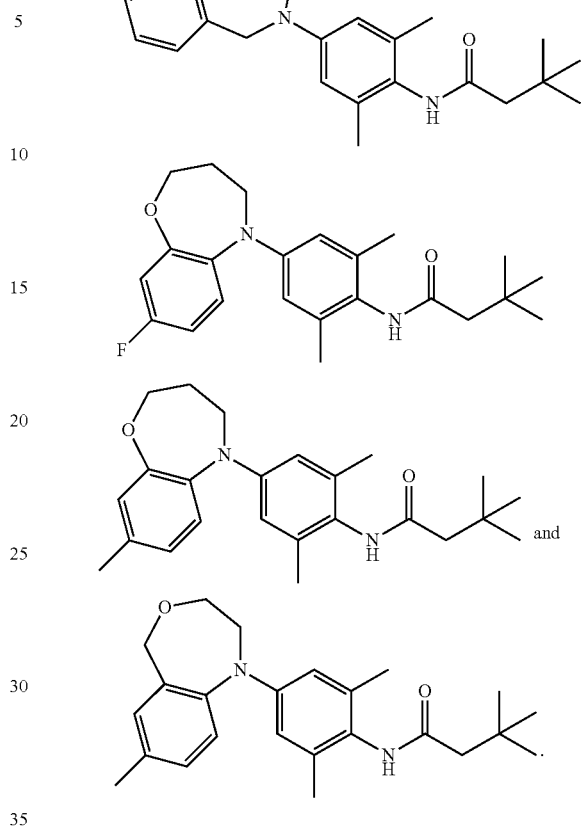
6. The method of claim 1, wherein:
the disorder or condition is amyotrophic lateral sclerosis.
7. The method of claim 1, wherein:
the seizure symptoms include convulsions, epilepsy and status epilepticus.
8. The method of claim 1, wherein:
the disorder or condition is inflammatory pain.
9. The method of claim 1, wherein the compound is selected from the group consisting of:
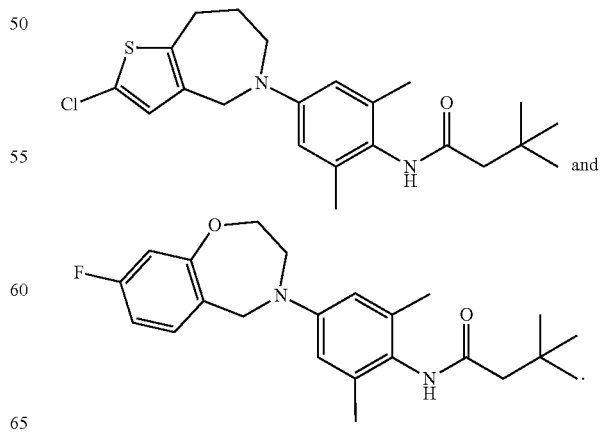

10. The method of claim 1, wherein the compound is
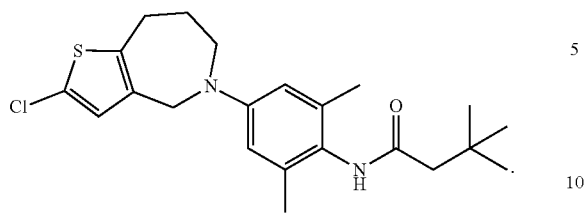
11. The method of claim 1, wherein the compound is
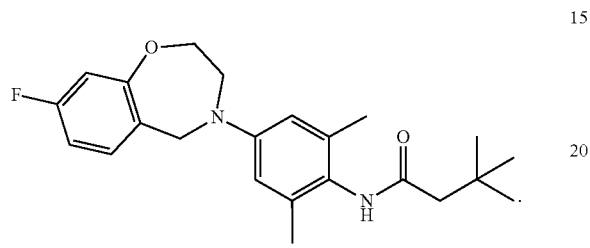
* * * * *